United States Patent
Brugger et al.

(10) Patent No.: US 11,400,194 B2
(45) Date of Patent: Aug. 2, 2022

(54) FLUID MANAGEMENT AND MEASUREMENT SYSTEMS, DEVICES, AND METHODS

(71) Applicant: NxStage Medical, Inc., Lawrence, MA (US)

(72) Inventors: James M. Brugger, Newburyport, MA (US); Jeffrey H. Burbank, Manchester, MA (US); Goetz Friederichs, Beverly, MA (US); Scott W. Newell, Ipswich, MA (US); William J. Schnell, Libertyville, IL (US); Orlando Soto, Amesbury, MA (US)

(73) Assignee: NxStage Medical, Inc., Lawrence, MA (US)

(*) Notice: Subject to any disclaimer, the term of this patent is extended or adjusted under 35 U.S.C. 154(b) by 289 days.

(21) Appl. No.: 16/621,827

(22) PCT Filed: Jun. 24, 2018

(86) PCT No.: PCT/US2018/039191
§ 371 (c)(1),
(2) Date: Dec. 12, 2019

(87) PCT Pub. No.: WO2018/237376
PCT Pub. Date: Dec. 27, 2018

(65) Prior Publication Data
US 2020/0171230 A1   Jun. 4, 2020

Related U.S. Application Data

(60) Provisional application No. 62/524,498, filed on Jun. 24, 2017, provisional application No. 62/524,490, (Continued)

(51) Int. Cl.
*G01R 27/08* (2006.01)
*A61M 1/16* (2006.01)
(Continued)

(52) U.S. Cl.
CPC ........ *A61M 1/1658* (2013.01); *A61M 1/1601* (2014.02); *A61M 1/1672* (2014.02);
(Continued)

(58) Field of Classification Search
CPC ...... G01N 27/025; G01N 27/08; G01N 27/07; G01N 27/06; G01N 27/02; G01N 27/023;
(Continued)

(56) References Cited

U.S. PATENT DOCUMENTS

2004/0012395 A1* 1/2004 Salamitou .............. G01N 27/07
324/444
2009/0012452 A1  1/2009 Slepicka et al.
(Continued)

FOREIGN PATENT DOCUMENTS

CN     103163384 A    6/2013
WO    2012082970 A1   6/2012
(Continued)

OTHER PUBLICATIONS

International Preliminary Report on Patentability dated Jan. 2, 2020 issued in International Application No. PCT/US2018/039191.
(Continued)

*Primary Examiner* — Thang X Le
(74) *Attorney, Agent, or Firm* — Potomac Law Group, PLLC; George Dolina

(57) ABSTRACT

A medicament preparation system includes a disposable cartridge with a flow path. Various sensors may be placed on the cartridge to measure qualities of the fluid flowing through the flow path. The sensors are placed in precise locations using various approaches that make manufacturing of the cartridge efficient and repeatable. A drain line that is susceptible to fouling may be preattached and various approaches are used to remove or reduce the fouling. An elastomeric contact can also be present in the medical
(Continued)

preparation system and used in a conductivity measurement subsystem.

18 Claims, 25 Drawing Sheets

Related U.S. Application Data filed on Jun. 24, 2017, provisional application No. 62/524,495, filed on Jun. 24, 2017, provisional application No. 62/524,513, filed on Jun. 24, 2017.

(51) Int. Cl.
*G01N 27/06* (2006.01)
*G01N 27/08* (2006.01)
*G01R 27/22* (2006.01)

(52) U.S. Cl.
CPC .............. *G01N 27/06* (2013.01); *G01N 27/08* (2013.01); *G01R 27/22* (2013.01); *A61M 2205/3317* (2013.01); *A61M 2205/3368* (2013.01)

(58) Field of Classification Search
CPC ...... G01N 27/026; G01R 27/22; G01R 27/28; G01R 27/3272; G01R 27/3273
See application file for complete search history.

(56) References Cited

U.S. PATENT DOCUMENTS

| | | | |
|---|---|---|---|
| 2009/0233330 A1* | 9/2009 | Sachs | ................ G01N 15/1031 |
| | | | 435/39 |
| 2012/0068723 A1 | 3/2012 | Sullivan | |
| 2015/0093486 A1 | 4/2015 | Rijn et al. | |
| 2017/0119970 A1 | 5/2017 | Bammer et al. | |
| 2017/0241929 A1* | 8/2017 | Qui | ...................... G05D 7/0617 |
| 2017/0307580 A1* | 10/2017 | Kim | ................... G01N 33/1893 |
| 2018/0052133 A1* | 2/2018 | Godfrey | ............... G01N 27/226 |
| 2019/0001492 A1* | 1/2019 | Rose | ......................... G01L 1/16 |

FOREIGN PATENT DOCUMENTS

| | | |
|---|---|---|
| WO | 2014018798 A2 | 1/2014 |
| WO | 2016049542 A2 | 3/2016 |

OTHER PUBLICATIONS

Extended European Search Report dated Jun. 14, 2021 for European Patent Application No. 18820748.4.
International Search Report and Written Opinion dated Oct. 17, 2018 issued in International Patent Application No. PCT/US2018/039191.
Office Action (First) dated Dec. 2, 2021 for Chinese Patent Application No. 201880054851.0.

* cited by examiner

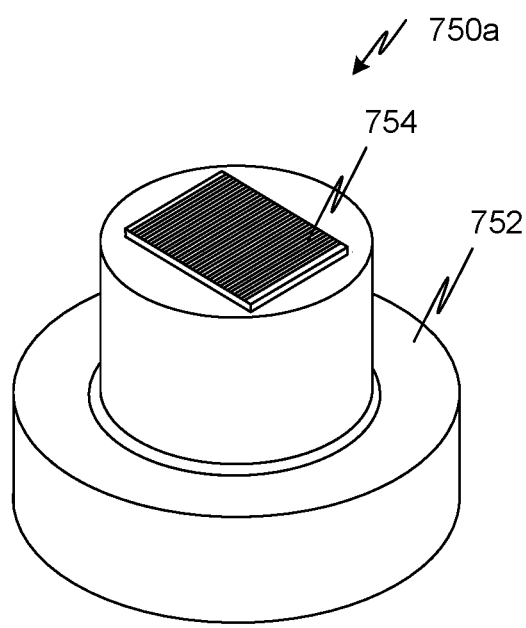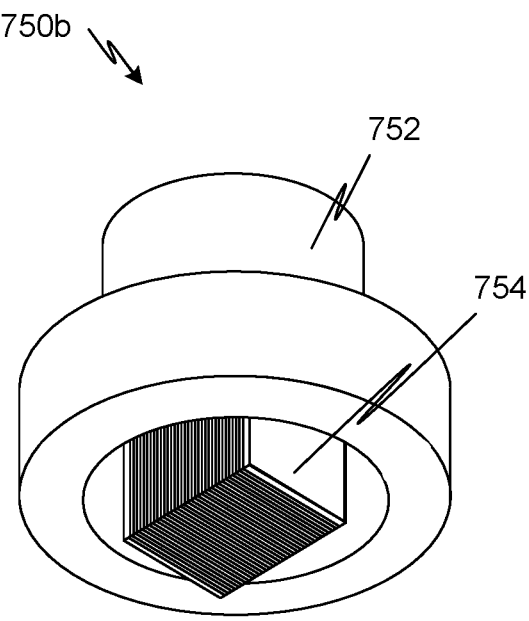
Fig. 13A	Fig. 13B
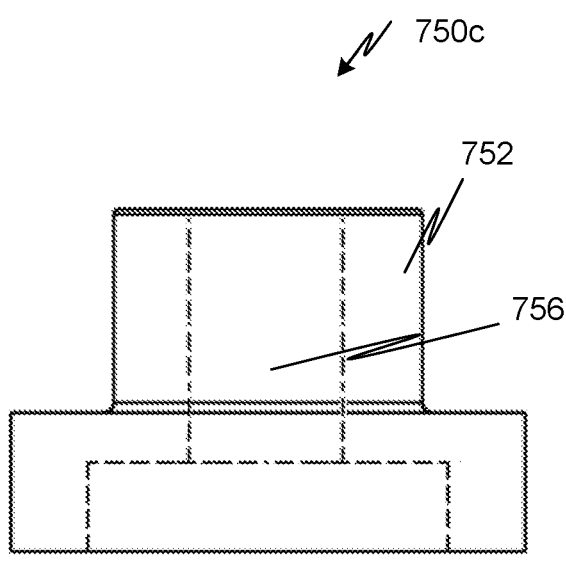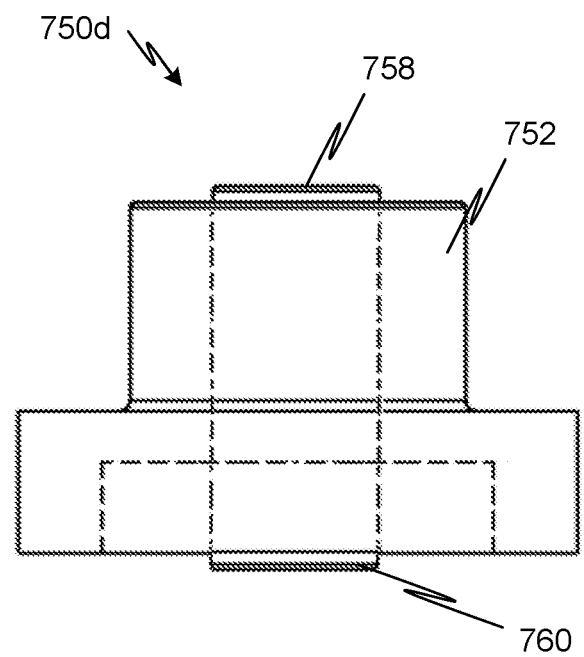
Fig. 13C	Fig. 13D

FLUID MANAGEMENT AND MEASUREMENT SYSTEMS, DEVICES, AND METHODS

CROSS-REFERENCE TO RELATED APPLICATIONS

This application is a U.S. national stage filing under 35 U.S.C. 0 371 of International Application No. PCT/US2018/039191, filed Jun. 24,2018, which claims the benefit of priority to U.S. provisional application No. 62/524,498, filed Jun. 24, 2017; U.S. provisional application No. 62/524,490, filed Jun. 24, 2017; U.S. provisional application No. 62/524,495 filed Jun. 24, 2017; and U.S. provisional application No. 62/524,513 filed Jun. 24, 2017, all of which are hereby incorporated by reference in their entireties.

BACKGROUND

There are many types of blood processing and fluid exchange procedures, each providing different therapeutic effects and demanding different processing criteria. Some procedures entail the removal of blood or another fluid from an individual and the return of blood or another fluid to the individual in a controlled fashion. Other types use natural body tissues to exchange blood components with a medicament. Examples of such procedures include hemofiltration (HF), hemodialysis (HD), hemodiafiltration (HDF), and peritoneal dialysis (PD). A common requirement of such procedures is the provision of large quantities of medicament such as dialysate that has a precise mixture of solute components and is free of contaminants and pyrogenic materials.

Some known systems for preparing medicaments such as dialysate are continuous proportioning systems and batch mixing systems. Carrying out treatment procedures using medicaments may employ special-purpose machinery. In the dialysis treatments listed above, devices called cyclers are often used. These pump fluid and may also pump blood, depending on the treatment. In the process of pumping, they precisely proportion the net amounts of fluid supplied and discharged and ensure safety by various means including monitoring of pressure, temperature, leaks, and other treatment conditions. In principle, these treatments are relatively simple, but because of the need for patient safety and health outcomes, treatment procedures and treatment systems are complex.

Home delivery of these treatments raises concerns about safety and treatment efficacy. One of the drawbacks of home treatment is the need for a supply of purified water. In clinics, large reverse osmosis plants provide a continuous supply of purified water. In the home, such large systems may not be practical because they require high volume of water and drainage. Installing and using relevant components can be a difficult and expensive task and may require modifications to a patient's home. In addition, the systems for the production of properly mixed medicaments in pure form require a high level of precision and safeguards as well as training and maintenance. To provide effective and safe systems for home delivery of blood treatments, there is an on-going need for innovations in these areas and others. For example, PCT publication number WO2016049542, which is incorporated herein by reference in its entirety, discloses a medicament preparation system that includes a water purification module and a medicament proportioning module, where the system is configured to allow convenient and safe use in a home environment or a critical care environment as well as others affording safety, reliability, and a compact form factor.

Some medical devices combine two or more substances to produce a medicament. One example is the preparation of dialysate for dialysis, where different fluids are mixed, such as a concentrated dialysate and a diluent such as water. It is desirable to control precisely the amount of the dialysate concentrate, or other fluids, as they are combined with the diluent. In certain situations, uncontrolled or accidental mixing may take place due to gravimetric action or due to pressure or vacuum created downstream in the fluid channel.

Many medical devices have portions that are replaced regularly and other portions that replaced less frequently or are permanent. The latter may be used repeatedly, depending on the application, for preparation of treatment fluids or treatment with treatment fluids as well as other applications.

In some treatment systems or fluid preparation systems (generically identified herein as fluid management systems) a common component is a portion of the fluid circuit that directs waste fluid to a drain. Such components can become fouled due to the repeated use. Examples of such systems include treatment devices, fluid preparation such as admixing devices, and water purification systems.

A disposable medical device may benefit from the ability to accurately measure conductivity or resistivity of a liquid. To this end, a conductivity sensor can be formed from two electrodes positioned at two locations in a fluid chamber. A current is generated between the electrodes with a current source as the voltage between the electrodes is measured. With knowledge of the size and shape of the volume between the electrodes and the contact areas of the electrodes (sensor dimensions) a "cell constant" can be calculated and used to calculate the conductivity of the fluid. The cell constant can be measured for a representative sensor such that the sensor dimensions need not be known explicitly by calibrating using a fluid having known conductivity. The driving current and detected voltage are typically alternating to avoid signal drift due to various known chemical and physical drivers.

The accuracy of the conductivity sensor is influenced by assurance of consistent sensor dimensional parameters. The latter include the physical relationship between the two electrodes and their relationship to the fluid volume defining the conduction path. Therefore, it is advantageous to control the placement of the electrodes within the housing of the conductivity sensor during the manufacturing process. The conductivity sensor may be a part of a disposable medical component such as a portion of a fluid circuit, where the manufacturing process may constrain the achievable manufacturing tolerances. These issues, and others, are addressed by embodiments of the present disclosure. Summary An elastomeric electrical contact is formed by a parallel array of wires supported on an elastomeric block. The wires may span a relief formed in a side surface of the block. The wires may wrap over three sides of the elastomeric block and make contact with contacts in a silicone housing. The contacts in the housing may be, for example, on the side or on the bottom side opposite the top surface of the elastomeric block. The elastomeric contact may be used in a replaceable component of a medicament preparation system to establish a reliable electrical connection with a sensor in a permanent component of the medicament preparation system. The medicament preparation system may include a water purification module and a medicament proportioning module, and may be configured to allow convenient and safe use in a home environment or a critical care environment as well as others, thus affording safety, reliability, and a compact form factor. The sensor may be a conductivity cell in which current and voltage measurement contacts are reliably connected, by way of the elastomeric contact disclosed herein, to wetted electrodes in a replaceable component, so that the conductivity of a fluid is measured accurately.

Generally, a compliant multiconductor element is positioned between multiple terminal contacts that, whose function requires these multiple terminal contacts to make electrical contact by being forced against a single electrode to contact it at different positions on the electrode surface. The electrode element may be positioned at variable distances from the multiple terminal contacts due to manufacturing variability or uncertain engagement by a user, creating a potential for a high resistance connection between the electrode and the multiple terminal contacts. This may arise, in part, where the multiple terminal contacts a minor fraction of the size of the electrode such that a member carrying both elements would have to be perfectly aligned with the surface of the electrode in order for all of the multiple terminal contacts to make sure electrical contact with the electrode. This is because one of the contacts may begin to resist the forcing against before another of the multiple terminal contacts makes full electrical contact with the electrode. That is, one of the multiple terminal contacts, or a substrate carrying them, may "block" the another of the multiple terminal contacts from making full electrical contact with the electrode. For example, but not limited to this example, one of the multiple terminal contacts is connected to a current source and the other one of the multiple terminal contacts is connected to a voltage measurement device. According to the disclosed subject matter, a resilient element with many flexible conductors running from one surface of the element to the opposite surface is positioned between the multiple terminal contacts forming a connection between each of the multiple terminal contacts and the single electrode. The number of the flexible conductors may be sufficient for there to be redundant connections between each of the multiple terminal contacts and the single electrode. In that case, the redundancy can help ensure that if some conductors make incomplete contact with the electrode and a respective one of the multiple terminal contacts, the other may still do so. In the above arrangement, an electrode that is tilted relative to the surface of the compliant multiconductor element or relative to the path of closure between the multiple terminal contacts and the electrode, the compliance of the compliant multiconductor element will prevent the blocking effect described above.

In the disclosed embodiments, the compliant multiconductor element is mated to a disposable device containing the electrode. A housing forms a sealed connector that holds the compliant multiconductor element in place adjacent the electrode. In embodiments, a conductivity cell with two electrodes are each provided with a housing and compliant multiconductor element. A permanent excitation component (a device with a current source and a voltage measurement device to which a disposable device carrying the electrodes is attached) with multiple terminal contacts to be electrically connected to each of the electrodes is engaged with the device carrying the electrodes by forcing them together. The housing holds the compliant multiconductor element on the electrode. The compliant multiconductor element is thus used only for duration of the use of the disposable device and is advantageously carried by it. In alternative embodiments, the compliant multiconductor element is attached to the permanent excitation component.

The general form of the compliant multiconductor element may be like that of so-called zebra connectors. The zebra connectors are used to connect a component with multiple contacts one-to-one to multiple contacts. They are in the general category of electronic interconnect devices. Designers employ them where a large number of very small contacts, for example a row of contact pads, each a fraction of a millimeter across, must be contacted with each other, the rows being parallel and facing each other. Then the zebra connector can be placed between them rows and pressed together to cause the contacts to make electrical contact through the zebra connector conductors. A common application example is connecting LCD panels. In the present embodiments, the same type of zebra connector may be used in a device having larger contacts, for example, ones that are more than a millimeter in size. The zebra connector may be used to connect a pair of contacts with a single electrode rather than corresponding contacts in one-to-one fashion. Also, the zebra connector is used in applications where the contact strips are thin and known to be flexible requiring a compliant mechanism to form a sandwich to make the electrical contacts. In the present application of a single electrode connecting to a small number of contacts, other solutions such as pogo pins or leaf spring contacts would generally be used.

Embodiments of the present disclosure provide conductivity sensor with a housing that can be manufactured by various processes such as injection molding, casting, or extrusion, optionally combined with thermal or mechanical machining. The disclosed embodiments provide resistance to variation in critical sensor dimensions due to manufacturing variability such as applied forces, quantities of cement, offsets in assembly of components, etc. In particular, the critical sensor dimension of the electrode fluid contact area, position, and shape are precisely controlled with effective and reliable sealing of the electrodes to a housing. It may be appreciated that while embodiments below are focused on a conductivity sensor that includes an insertable electrode in an opening of a housing, the disclosure is also applicable to a multitude of other applications where it is necessary to press, push, insert, or force an object into an opening and obtain a repeatable and predictable fit within that opening.

It is desirable to precisely and repeatedly position an electrode within openings of a housing according to embodiments of the disclosure. The housing may define a flow channel for continuous monitoring of conductivity of a flowing fluid. The housing may also be a vessel where fluid is stored. Each electrode is positioned in an opening whose axial profile ("axial" referring to a central axis of the opening connecting the interior of the housing with the exterior along the most direct line). The opening may have a stepped profile so that moving from outside to inside the housing, the area of the opening diminishes. That is, an outside portion of the opening has a larger diameter than an inside portion of the opening. The outside portion may include one or more spacers that project radially inward but which do not extend across the circumference of the opening inside portion. The inside portion may have a rim that extends axially toward the outside of the housing. The rim defines a trough. When an electrode is pressed into the outer portion it is over-constrained by the spacers which are the only parts in contact with the inserted electrode until the electrode lands against the rim to seal the opening fully. The placement of the spacers provides precise centering of the inserted electrode within the opening, and minimizes deformation of the inserted electrode and the housing. Further, the spacers may have a shape that allows the electrode to be pressed in with force that is low, consistent, and uniform along a length of the traversal while confining the position of the electrode as it is pressed home. When the electrode reaches home, the resistance force is no longer frictional (or due to scraping of the spacers) but rather generated by interference caused by seating on the rim. An assembly line robotic press can exploit the sudden rise in resistance force exerted to determine that the electrode has been fully inserted when the assembly line machine exerts a predetermined maximum force on the electrode.

As the electrode is pressed into the opening of the housing, the spacers are physically deformed since the space for the electrode may be made slightly smaller than the electrode. It is possible that a part or parts of the spacers may be scraped or shaved off to produce one or more shaving or burrs. These may remain attached or break off when each electrode is pressed into an opening of the housing. To prevent any shaving or burr from interfering with consistent placement of the electrode, such shavings or burrs are received in a trough so that they cannot become trapped between the electrode and a final seating surface defined by the rim. Thus, any burrs or shavings can bend away or fall away into the trough thereby leaving an arrest surface (e.g., the top of the rim) free of obstructions whereby the electrode is fully pressed into its intended position, providing for highly precise positioning of the electrode within the housing.

Various embodiments of the present disclosure provide a medicament preparation system that includes a fluid circuit having fluid channels with at least one junction, the junction joining a common flow channel that leads from a water inlet to a medicament outlet. The junction may be joined to a pumping tube segment connected to a source of medicament concentrate by a concentrate channel. The fluid circuit may be oriented in a predefined way relative to the force of gravity. The concentrate channel has a chicane that curves sharply up and sharply down before the concentrate channel meets the common flow channel.

In embodiments, the chicane's length may be no greater than ten internal diameters of the concentrate channel local to the chicane.

In embodiments, the chicane is immediately adjacent a point where the common flow channel and the concentrate channel meet.

In embodiments, the internal cross-sectional flow area of the chicane is smaller than that of the remainder of the concentrate channel.

In embodiments, the chicane is operable as a trap when fluid of a first density remains in the concentrate channel while fluid of a second density remains in the common flow channel at the junction, where the first density is higher than the second density, whereby gravity siphoning is prevented.

In embodiments, the fluid circuit may be formed in a rigid structure and/or in a rigid cartridge.

In embodiments, an overhang may be present to reduce or prevent the diluent from entering the concentrate channel.

In embodiment, a flap that is biased in the closed position may be present in addition to, or instead of, the chicane. The flap bias force is sufficient to prevent flow of the concentrate due to gravimetric action, but the bias force is overcome when the concentrate is pumped along the concentrate channel to allow mixing with the diluent.

In embodiments, a gravity trap in a fluid path or fluid circuit reduces the occurrence, or prevents, unintended mixing of fluids of different densities caused by gravimetric action. In an exemplary embodiment, the gravity trap can be included in an online dialysis proportioning system that prepares dialysate from a concentrate. In this example, the fluids that are admixed may be a dialysate concentrate and purified water, but other concentrates and diluents are envisioned. In an embodiment, one of the fluids is a mixture of purified water and bicarbonate, while the other fluid is an acid.

Objects and advantages of embodiments of the disclosed subject matter will become apparent from the following description when considered in conjunction with the accompanying drawings.

BRIEF DESCRIPTION OF DRAWINGS

Embodiments will hereinafter be described in detail below with reference to the accompanying drawings, wherein like reference-numerals represent like elements. The accompanying drawings have not necessarily been drawn to scale. Where applicable, some features may not be illustrated to assist in the description of underlying features.

FIGS. 13A-13D show various views of embodiments of a housing that supports an elastomeric contact insert in an elastomeric contact that may be used with a conductivity measurement component in any of the embodiments disclosed or claimed.

DETAILED DESCRIPTION

Figure 1A:
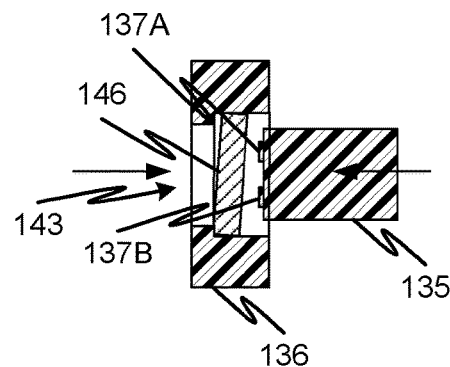
FIGS. 1A and 1B show a contact issue that arises in connection with multiple point electrode contacts for an article of manufacture containing an electrode which interfaces with a permanent multi-point contact element.
Figure 1B:
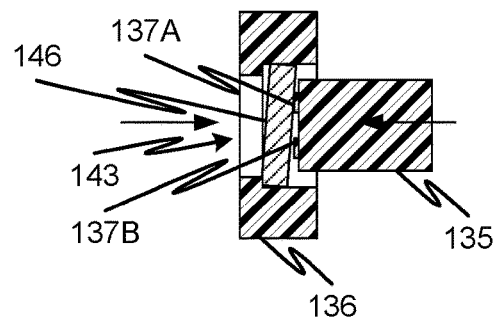

FIG. 1A shows an interface element 135 having contacts 137A and 137B which are positioned to engage an electrode 146, or other conductive element, at two points thereon. The electrode 146 is supported by a member 136 which has an opening 143 covered and sealed by the electrode 146. The member 136 may be a portion of a wall of a conductivity measurement device such as described with reference to FIGS. 7A-7E. The interface element 135 and member 136 are moved toward each other so that the contacts 137A and 137B are moved toward the electrode 146 as shown by the arrows. FIG. 1B shows the interface element 135 and member 136 have stopped moving due to interference engagement with contact 137A. This leaves contact 137B spaced apart from the electrode 146. This is due to the angles position of the electrode 146 relative to the contacts 137A and 137B. The angled position of the electrode 146 circumstance is exaggerated in the figures and the contact failure may not be as clear cut in a real-world circumstance due variability due to imperfect manufacturing of the member 136 and electrode 146.

Figure 1C:
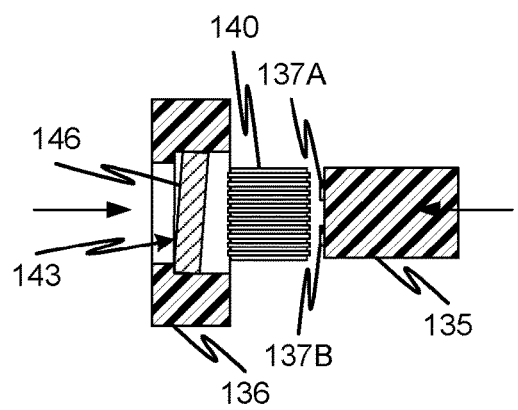
FIGS. 1C and 1D illustrate a mechanism for overcoming a contact issue that arises in connection with multiple point electrode contacts for an article of manufacture containing an electrode which interfaces with a permanent multi-point contact element according to embodiments of the disclosed subject matter.
Figure 1D:
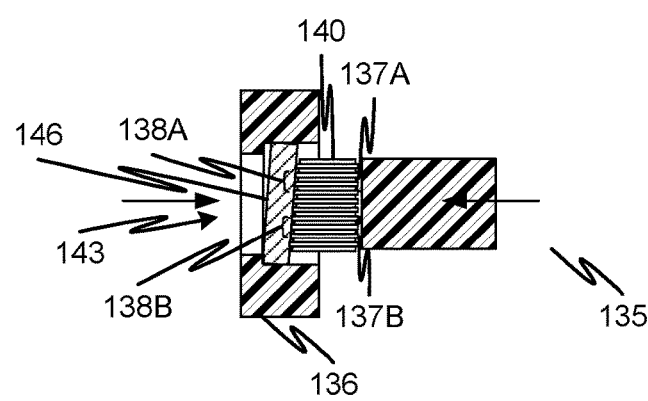
Figure 1E:
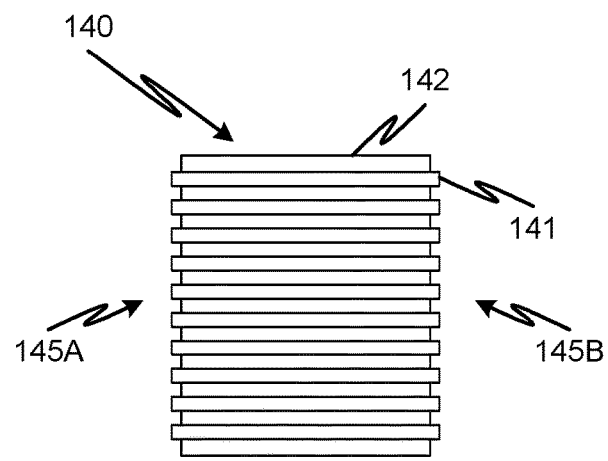
FIG. 1E shows a compliant multiconductor element according to embodiments of the disclosed subject matter.

FIGS. 1C and 1D show how the interposition of a compliant multiconductor element 140 may allow complete contact between the electrode and both of the contacts 137A and 137B. Referring briefly to FIG. 1E the compliant multiconductor element 140 has an elastomeric block 142, which may have additional features cut out of it to make it more compliant as discussed below. Flexible conductors 141 (only one of many parallel conductors is indicated by the reference numeral) are attached on opposite faces 145A and 145B of the elastomeric block 142 which, as illustrated, are perpendicular to the plane of the drawing page, of the elastomeric block 142. The flexible conductors 141 may be thin wires or metallic tape or conductive traces deposited on the elastomeric block 142. The flexible conductors 141 wrap around the opposing faces 145A and 145B and bridge across (in the direction parallel to the plane of the drawing page) so that when interposed between interface element 135 and the member 136, this creates an electrical continuity between a region 138A of the electrode 146 and contact 137A and between region 138B of the electrode 146 and contact 137A. The electrical continuity contact may be formed by multiple conductors 141. It can be observed that the compliant multiconductor element 140 deformation when the interface element 135 and the member 136 are forced together allows continuity to be made between the electrode 146 and the contacts 137A and 137B. The scales of the elements shown are not necessarily representative of a real-world embodiment and the sizes and numbers of elements are modified to for description purposes.

The compliant multiconductor element 140 may conform to the so-called Zebra elastomeric connector used commonly for making one-to-one electrical contact between a row of contacts of a liquid crystal display panel and corresponding contacts pads of a graphics processing unit. Note that instead of conductors 141, the compliant multiconductor element 140 may be a many-layered sandwich of conductive and insulating materials. The conductive layers may be, for example, carbon-filled elastomeric material. In typical applications, known elastomeric connectors are used for extremely high pitch contact spacing applications in which the contact size and spacing is no more than a millimeter or two and commonly a minor fraction of a millimeter. The present system may employ contacts that are several millimeters wide. Another difference from conventional uses of Zebra connectors is the number of contacts. Zebra connectors are generally used to map many contact pads, in the tens, hundreds, or thousands rather than two as in the present embodiments. Yet another difference is that the multiple contacts, for example, 137A and 137B are electrically connected by the compliant multiconductor element 140 to a single electrode 146 at multiple positions, rather than respective contacts. Still another difference is that the disclosed compliant multiconductor element 140 has an aspect ratio of about unity so that it can maximally fill the area of a round electrode. As discussed below, the compliant multiconductor element 140 may be captured and held to the electrode by a housing to form a part of a consumable component of a medical treatment device. Other differences in the application will be revealed in the following embodiments.

Figure 2:
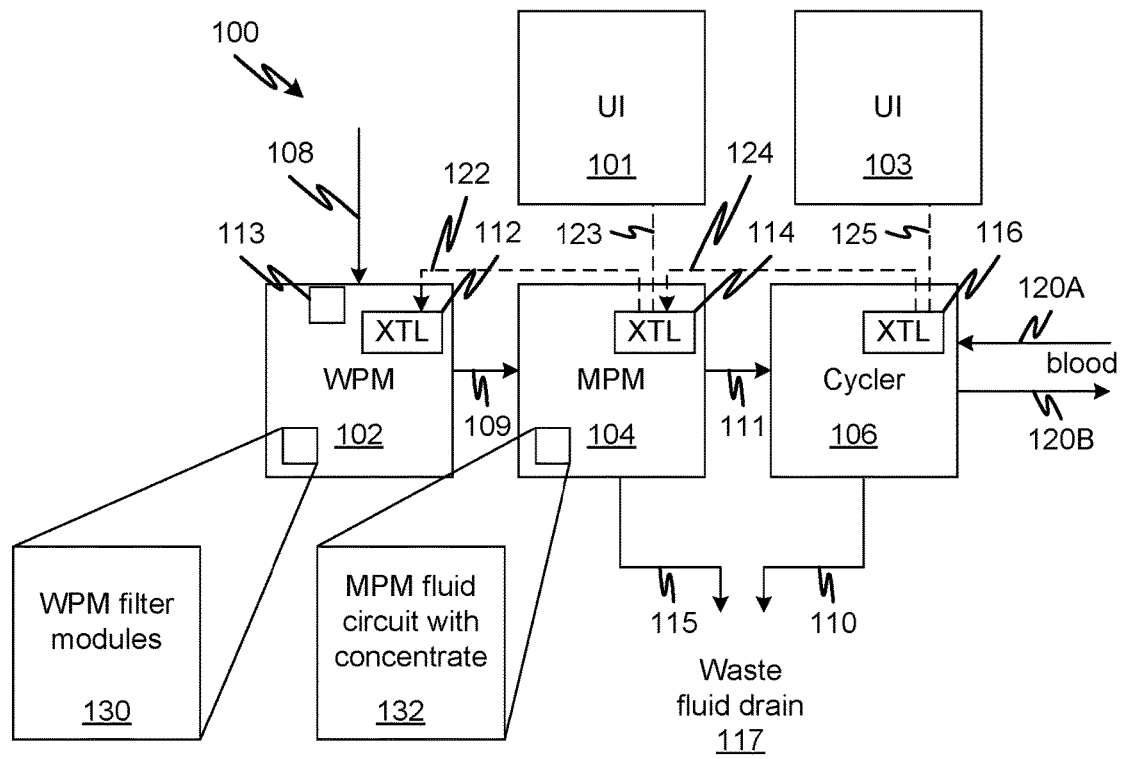
FIG. 2 shows an overview of an online system that includes a water purification module, proportioning medicament proportioning module, and a cycler forming an online treatment system, according to embodiments of the disclosed subject matter.

FIG. 2 shows an overview of an online water purification, proportioning medicament generation, and treatment system 100, according to embodiments of the disclosed subject matter. A water purification module 102 receives tap water 108 from a municipal water supply. The water purification module 102 purifies the water and checks its purity, under control of a controller 112 and using a water quality sensor (219 in FIG. 2). The water quality sensor 219, in embodiments, includes a conductivity sensor. The water purification module 102 utilizes one or more filter modules 130 which are replaced at intervals to help maintain the ability to generate product water that is sterile and ultra-pure. Product water 109 from the water purification module 102 is conveyed to a medicament proportioning module 104 which mixes one or more concentrates and the product water 109 in a replaceable fluid circuit 132 to generate a medicament 111. The medicament concentrates are diluted in a predefined proportion to generate product medicament 111. One or more concentrates may be utilized and combined in the product medicament 111. The water purification and medicament generation are performed in in-line fashion and on-demand, which means water is purified and mixed with medicament concentrate as a continuous process, at a rate of consumption and as demanded by a final consumer, in this case, a cycler 106. Waste produced by the medicament proportioning module 104 is conveyed as indicated at 115 to a drain 117. Waste 110, for example spent medicament, is conveyed to the same or other drain 117.

Each of the water purification module 102, the medicament proportioning module 104, and the cycler 106 may include a respective controller 112, 114, and 116. All of the controllers 112, 114, and 116 may be in communication as indicated by lines 122 and 124. In alternative embodiments, a smaller or larger number of controllers may be used and they may be associated with each module 102, 104, and cycler 106 or shared among the modules 102, 104, and cycler 106. One or more user interfaces, figuratively indicated at 101 and 103, may be connected to one, two, or the entire water purification module 102, medicament proportioning module 104, and/or cycler 106. Connections between the user interfaces 101, 103, indicated at 123 and 125, may be wired or wireless. In embodiments, control may be provided through a single user interface 103, and each module may transmit commands responsive to commands from the user interface 103 to the respective controllers 112 and 114 of the water purification and medicament proportioning modules 102 and 104, in parallel or serially. In embodiments, the cycler 106 receives and returns blood in arterial and venous lines 120A and 120B, respectively. In other embodiments, medicament is conveyed to and from a patient, for example in a peritoneal dialysis treatment.

Figure 3:
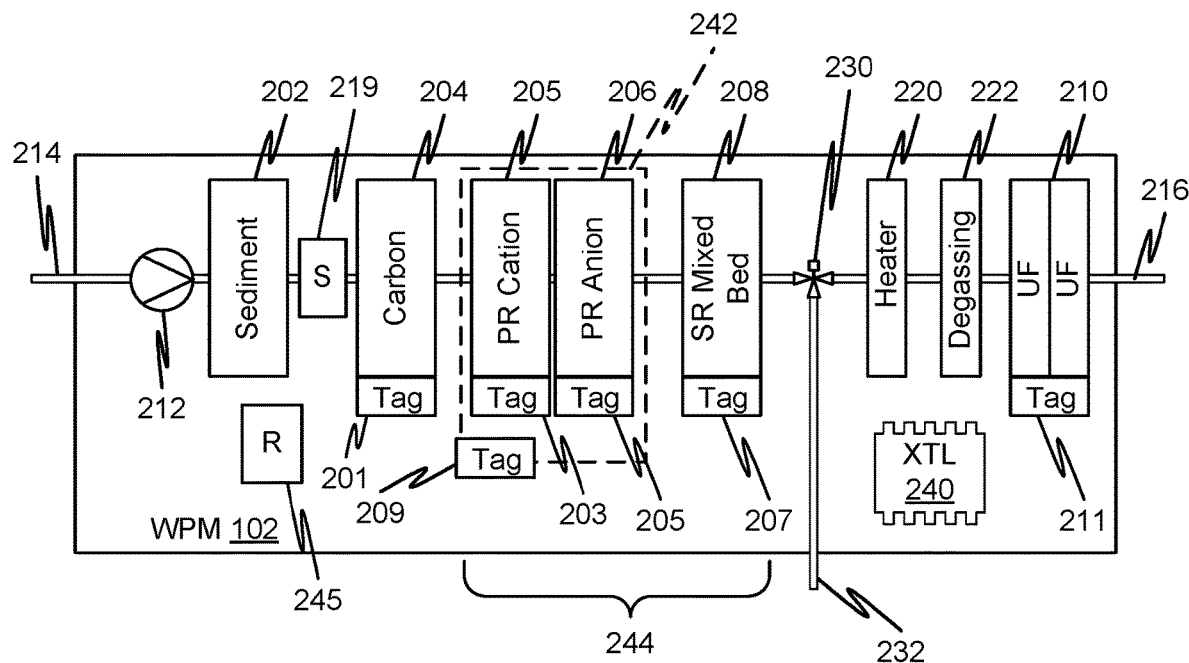
FIG. 3 shows details of the water purification module of the embodiment of FIG. 1, according to embodiments of the disclosure subject matter.

FIG. 3 shows details of the water purification module 102 of the embodiment of FIG. 2. Referring now to FIG. 3, a water purification module 102 receives tap water from an inlet 214, the tap water being pumped by a pump 212 and passed through a sediment filter 202, a water quality sensor station 219, and an activated carbon filter 204. Water from the activated carbon filter 204 is received by a two-stage deionization filtration element 244 that includes a primary resin cation stage 205, a primary resin anion stage 206, and a secondary mixed resin bed 208. The primary resin cation stage 205 and the primary resin anion stage 206 may be combined in a single replaceable unit 242 or may be separately replaceable. The primary resin cation stage 205, the primary resin anion stage 206, and the secondary mixed resin bed 208 may also be combined in a single replaceable unit in alternative embodiments. Deionized water from the two-stage deionization filtration element 244 passes through a diverter valve 230 which is controlled by a controller 240. The diverter valve 230 may selectively direct a flow of deionized water to a drain outlet 232. Deionized water passing through the diverter valve 230 for the generation of product water is directed to a heater 220, a degassing filter 222, and two or more sterile filters connected in series to form sterile filter stage 210 from which product water may be drawn through a product water outlet 216. A vacuum pump (not shown) may be provided on an air side of the degassing filter 222. The degassing filter 222 may have a hydrophobic membrane to allow gas to be removed from water flowing through it. The water purification module 102 may contain a replaceable unit 113 that includes a conductivity sensor according to any of the disclosed embodiments for detecting initial water quality.

The water quality sensor station 219 may output a signal indicating water quality, for example, a signal indicating conductivity of the water, which may be numerically cumulated by the controller 112 to generate, for any point in time, a remaining life of any of the filters provided herein. The water quality sensor station 219 may include a particle counter, a conductivity sensor, an optical opacity sensor, a pH sensor, a lab-on-a-chip chemical assay sensor, and/or another type of water quality sensor. The user interface 101 and/or 102 may allow the entry of other data regarding water quality. For example, a worst-case upper bound, or data related thereto, of raw water constituents may be provided.

An algorithm that predicts the rate of the various components, based on a measured indicator, may then be used to predict the rate of all contaminant constituents. In an example embodiment, the algorithm may predict that all contaminants are in the same proportion as a predefined value such that an indication of conductivity by the water quality sensor station 219 may thereby indicate the concentrations of the various contaminants. In embodiments, the controller 112 may output an indication of the remaining life of the various components or an indication that a component is at or near expiration. In a particular embodiment, the useful life of the deionization resin beds may be estimated based on conductivity indicated by water quality sensor station 219. The estimation of the remaining life may be based on the data carried by the data carrier of the replaceable tagged component indicating characteristics such as the capacity or type of decontaminating media employed thereby. The water quality sensor station 219 may be positioned at any suitable point downstream of the inlet 214, even though shown downstream of the sediment filter 202.

The pump 212 and sediment filter 202 may form permanent or infrequently-replaced components that are ordinarily not replaced by the user. The entire water purification module 102 is adapted for use by a home-bound patient and/or a helper although its features of compact size and low water volume requirement make it attractive for use in critical care environments. The tap water inlet 214 may be fitted with an adapter suitable for connection to an accessible permanent or temporary connection so that, for example in critical care environments, the water purification module 102 may be wheeled to a point of use and connected to a nearby water tap with such a connection fitting. In embodiments, the water purification module 102 is combined with the medicament proportioning module 104 in a single housing so that it can be wheeled to a point of use and/or compactly housed for use in a home.

Each of the replaceable components (activated carbon filter 204, primary resin cation stage 205, primary resin anion stage 206, replaceable unit 242, or sterile filter stage 210) may be fitted with a respective data carrier 201, 203, 209, 207, 211 such as a bar-code or radio-frequency identification (RFID) tag that carries a unique identifier respective to the attached component (again, attached component may be any of the activated carbon filter 204, primary resin cation stage 205, primary resin anion stage 206, replaceable unit 242, or sterile filter stage 210 and will generally be referred to as replaceable tagged component). Product water may be drawn through the product water outlet 216.

A reader 245 may be attached to the purification module 102 and may be positioned so as to actively or passively read the data carrier 201, 203, 209, 207, 211 of the replaceable tagged component. Reader 245 may be a scanner for an RFID, a bar-code scanner, a smart-chip reader, or any other type of data carrier reader, and may connect optically, electromagnetically, electrically through conductive contacts, or by any other suitable means. The information stored on data carriers may allow the controller 240 to verify that the correct type of replaceable tagged component is installed. The controller 240 may detect the removal or disconnection of a replaceable tagged component as well. In an embodiment, the controller 240 may generate a refuse signal and take corrective action (such as preventing use of the water purification module 102 or blocking installation of the replaceable tagged component or some other action).

Figure 4:
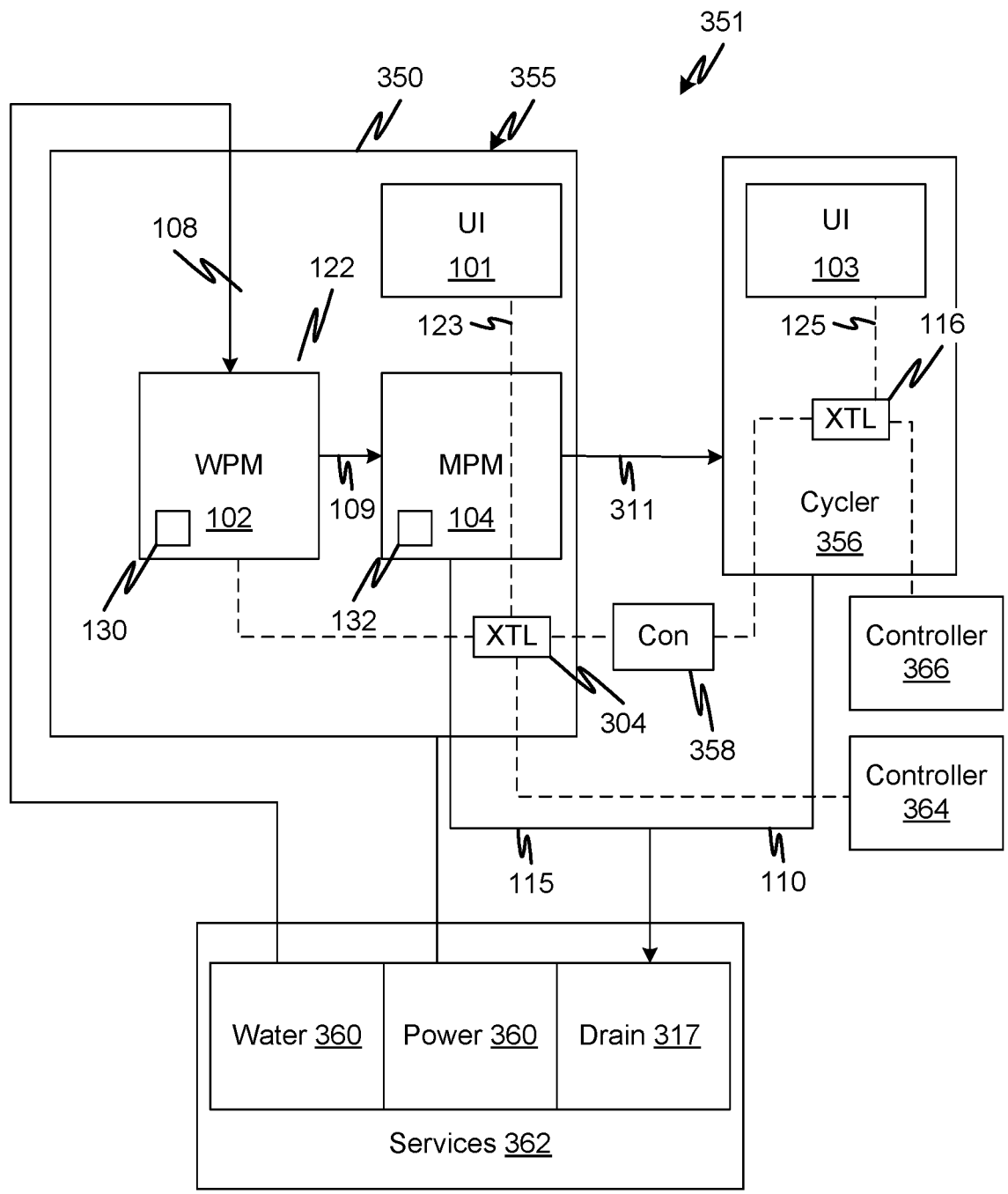
FIG. 4 shows an overview of an online water purification, proportioning medicament generation, and treatment system, according to embodiments of the disclosed subject matter.

FIG. 4 shows an overview of an online water purification, proportioning medicament generation, and treatment system 351. The water purification module 102 and medicament proportioning module 104 form a medicament generation system 355 and are commonly housed in a housing 350 with a user interface 101. The cycler 356 (or generally, a medical treatment device that consumes medicament generated by the medicament generation system 355) may form a separately housed device that is signally and fluid connected to the medicament generation system 355. Communications module 358 interconnects the controllers 304 and 116 of the medicament generation system 355 and cycler 356 respectively.

By combining the medicament generation system 355 with a cycler, a system suitable for use in a home, critical care, or clinic may be provided without a need for specialized services such as high capacity municipal water supply, power, or drainage. For example, high volume water supply is typically required in reverse osmosis-based water purification system. In the present embodiments, municipal water 360 is deionized using consumable deionization filter beds, allowing normal rates of water flow and drainage 317 in a services supply 362 that is typical of a home or the room services of a hospital. With power requirements at residential or typical hospital-room voltages and currents, available services allow the proportioning medicament generation, and treatment system 351 to be used for home and critical care, as well as in clinics. For clinics, the rapid set-up of a new installation can be facilitated as well because expensive capital infrastructure of an online medicament generation system can be avoided.

As in the embodiment of FIG. 2, the water purification module 102 receives tap water 108 from a municipal water supply. The water purification module 102 purifies the water and checks its purity under control of controller 304. The water purification module 102 utilizes one or more filter modules 130 which are replaced to help maintain its ability to generate product water that is sterile and ultra-pure. Product water 109 from the water purification module 102 is conveyed to a medicament proportioning module 104 which mixes concentrates provided in a replaceable fluid circuit 132 in a predefined proportion to generate a medicament 311. The water purification and medicament generation are performed in on-line fashion and on-demand, which means water is purified and mixed with medicament concentrate as a continuous process, at a rate of consumption and as demanded by a final consumer, in this case, a cycler 356. Waste produced by the medicament proportioning module 104 is conveyed as indicated at 115 to a drain 317. Waste 110, for example spent medicament, is conveyed to the same drain or another drain 317. The cycler 356 may be of any type including hemodialysis and peritoneal dialysis as well as other types of treatment systems.

The communication module may allow the controller 116 to send specific command signals to the medicament generation system 355, for example, to start and stop medicament generation. In a system in which the cycler 356 is not adapted to send specific commands, a status vector can be translated by the communications module 358 to convert it to one or more suitable commands. A status vector may include information such as whether a blood pump of the cycler 356 is running.

Controller 364 and 366 may communicate, respectively, with the medicament generation system 355 and cycler 356. The controllers 304 and 116 may generate operation or treatment logs and/or maintenance information which they may send the controller 366 for further distillation, synthesis, storage, or communication to other facilities and/or remote professional care management or maintenance personnel.

Figure 5:
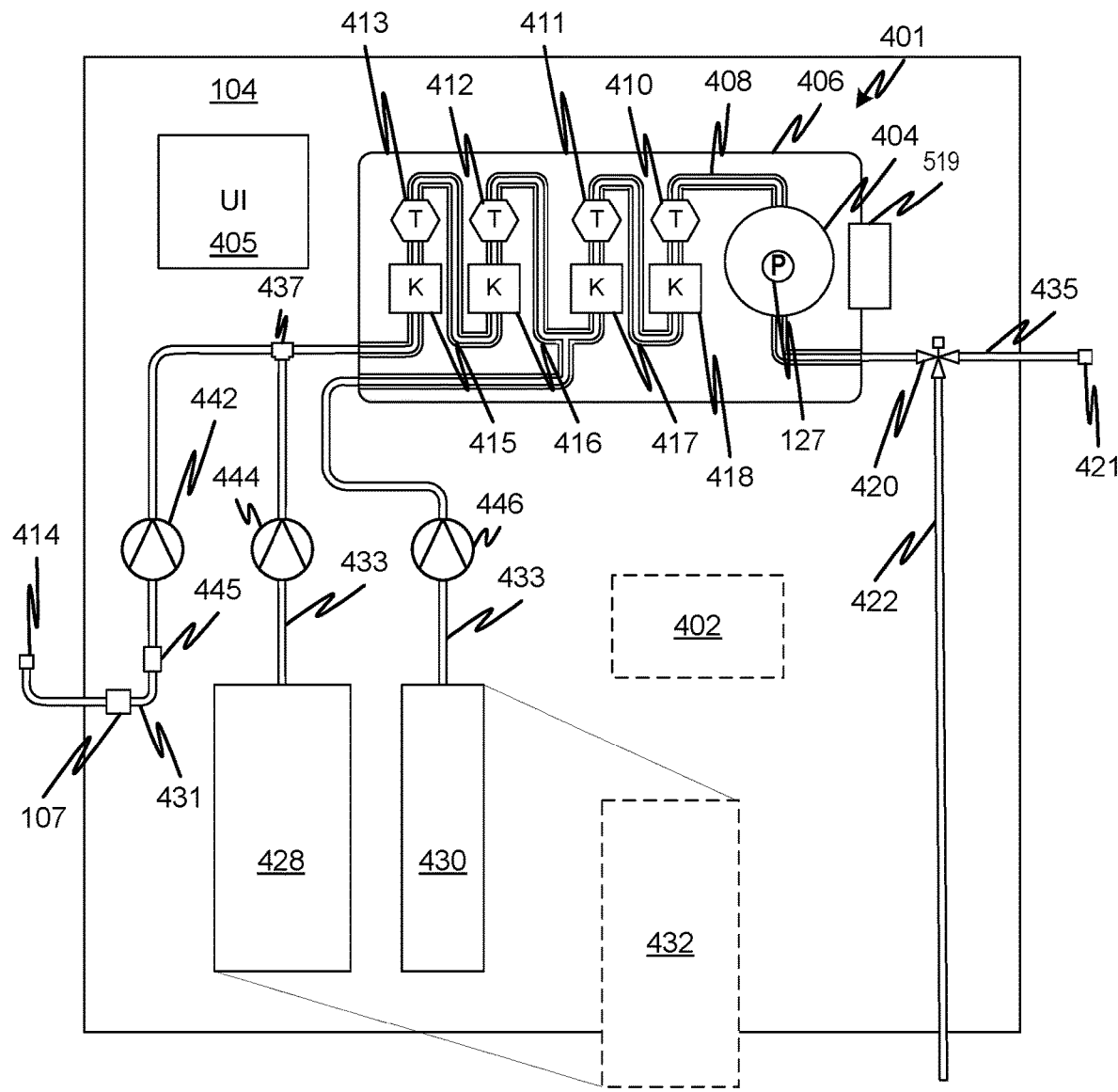
FIG. 5 shows details of an embodiment of medicament proportioning module, according to embodiments of the disclosed subject matter.

FIG. 5 shows details of an embodiment of medicament proportioning module 104 shown in FIG. 2. A sealed fluid circuit 401 is partially supported by a cartridge support 406. Flow lines supported by the cartridge support 406, shown generally at 408 may be tubes attached to the cartridge support 406 or formed therein by molded and sealed channels or in attached seam-welded flexible panels or by other suitable means. The sealed fluid circuit 401 may also include all the other lines and fluid circuit elements illustrated including such as waste line 422, inlet line 431, medicament concentrate lines 433, product medicament line 435, control valve 420, junction 437, and inlet sterile filter 445 to form a single pre-connected sterile disposable unit along with the flow lines 408 (and other elements supported by the cartridge support 406 described below). As explained, the entire sealed fluid circuit 401 shown in FIG. 5, save for the inlet line 431 inlet and product medicament line 435 are pre-connected and sealed from the external environment. The sealed fluid circuit 401 may be sterilized as a unit, for example, gamma-sterilized or heat-sterilized.

A source of pure water can be connected by way of a connector 414 which is capped and sterile-sealed prior to connection. By sterile-sealed it is meant that a seal is formed sufficient to physically block any contaminants from entering. A resistivity sensor 107 of the form of any of the disclosed conductivity sensor embodiments may be provided in the water inlet line. A sterile filter 445 ensures that any contamination in the flow, for example, resulting from touch contamination or a contaminated connector on the pure water source, is trapped by the sterile filter 445. Thus, sterile filter 445 forms part of the complete sterile barrier such that the entire sealed fluid circuit 401 has a continuous sterile barrier even after the connector 414 is unsealed, at least while the product medicament line 435 connector is capped with cap 421. The sterile filter may be one with a 0.2 μm membrane to block bacterial contaminants. Note that by ensuring that completely sterile deionized water flows into inlet line 431 and because the entire sealed fluid circuit 401 is sealed and sterile, the unit once set up and ready for treatment can be filled and used over an extended treatment without the risk of proliferation of contaminants. For example, the sealed fluid circuit 401 can be prepared for use and primed and used, up to 24 hours later. Alternatively, it may be used for more than one treatment.

Pure water flows through the sterile filter 445 at a rate of pumping determined by the pump 442. To match the rate of production of purified water with the rate of pumping by pump 442, the source of purified water may generate a constant supply into an accumulator, it may pump continuously with overflow to a drain, or a pump of the water purification module 102 may be commanded in response to the controller 402 of the medicament proportioning module 104. Reference numeral 432 indicates that a single concentrate, such as lactate buffered dialysate, can be substituted for the multiple-component concentrate. This is true of any of the embodiments.

The cartridge support 406 may be received in a medicament proportioning module 104 which may further be a stand-alone unit or combined with a water purification module 102. As illustrated, the medicament proportioning module 104 is a stand-alone unit. Purified water is received at an inlet 431, which forms a part of a disposable sterile fluid circuit that includes all the fluid lines and circuit components illustrated in the figure and/or discussed herein. Pump 442 pumps water that flows at a rate controlled by a controller 402. Pumps 444 and 446 regulate flows of respective medicaments concentrates in medicament concentrate lines 433 so that they are diluted in a precisely controlled ratio by the flow of water pumped by the pump 442. A first concentrate in container 428 pumped by pump 444 is combined in junction 437 with the flow of water pumped by pump 442, thereafter flowing into a conductivity measurement module 415 which generates a signal indicative of the concentration of medicament concentrate in the mixture emerging from the junction 437. A temperature signal indicating a temperature of the same flow is also generated by a temperature transducer 413. The signals indicating conductivity and temperature are applied to the controller 402 which converts them to concentration responsively to stored (in a data store of the controller—not shown separately) conductivity-temperature curves for the solution of the diluted first concentrate stored in the container 428. A secondary set of conductivity measurement modules 416, 417, 418 and temperature transducers 412, 411, 410 may be provided to provide signals indicating conductivity and temperature of the same flow as a confirmation. If the calculated concentrations differ, the controller 402 may generate a signal indicating a corresponding error condition. In response, the controller 402 may generate an error indication on a user interface 405 or halt the flow of medicament, or divert it through a diverting valve 420 to a waste line 422, for example.

The conductivity measurement modules 415, 416, 417, and 418 may each have a pair of electrodes sealed to a housing as described in more detail according to specific embodiments. Each electrode may be as described with reference to electrode 146 with a portion of a housing defining a fluid channel of each conductivity measurement module 415, 416, 417, and 418 corresponding to member 136. The interface element 135 corresponds to a permanent fixture, having the interface element and contacts 137A, and further having excitation and voltage detection circuits connected to the contacts 137A, the latter not being shown separately in the schematic of FIG. 5.

The second medicament concentrate is pumped by pump 446 from container 430 into a junction so that the second concentrate is mixed with the diluted first concentrate. The diluted and mixed first and second concentrates flow into a conductivity measurement module 417 which generates a signal indicative of the concentration of medicament concentrate in the mixture emerging from the junction. A temperature signal indicating a temperature of the same flow is also generated by a temperature transducer 411. The signals indicating conductivity and temperature are applied to the controller 402 which may convert them to concentration or some other parameter or the values may be used directly for comparison to a reference value. The temperature may be used to compensate the conductivity by a scaling factor to adjust for a difference between reference conductivity value taken at one temperature and an actual temperature at which the fluid conductivity is measured. In the present disclosure, in embodiments where concentration is an identified output from conductivity measurement it should be understood that temperature compensated conductivity or a raw signal may be used as well in any embodiment. As indicated, the conductivity measurements are made by the conductivity measurement modules 415, 416, 417, and 418. Note that a conductivity module of the same description may also be used for water quality sensing as described with reference to reference numeral 219.

A secondary (or redundant) set of conductivity measurement module and temperature transducers may be provided to provide signals indicating conductivity and temperature of the same flow as a confirmation. If the calculated concentrations differ, the controller 402 may generate a signal indicating a corresponding error condition. A final medicament product concentration flows through the line indicated at 408 into an accumulator 404 which has an expandable volume whose pressure may be substantially determined by a spring constant due to a spring-based restoring force. A pressure sensor 127 may measure the pressure in the accumulator 404. A connected device, such as cycler 106 can draw medicament through line 435. A cap 421 at the connector ensures a sterile output line and is removed before connection.

Figure 6:
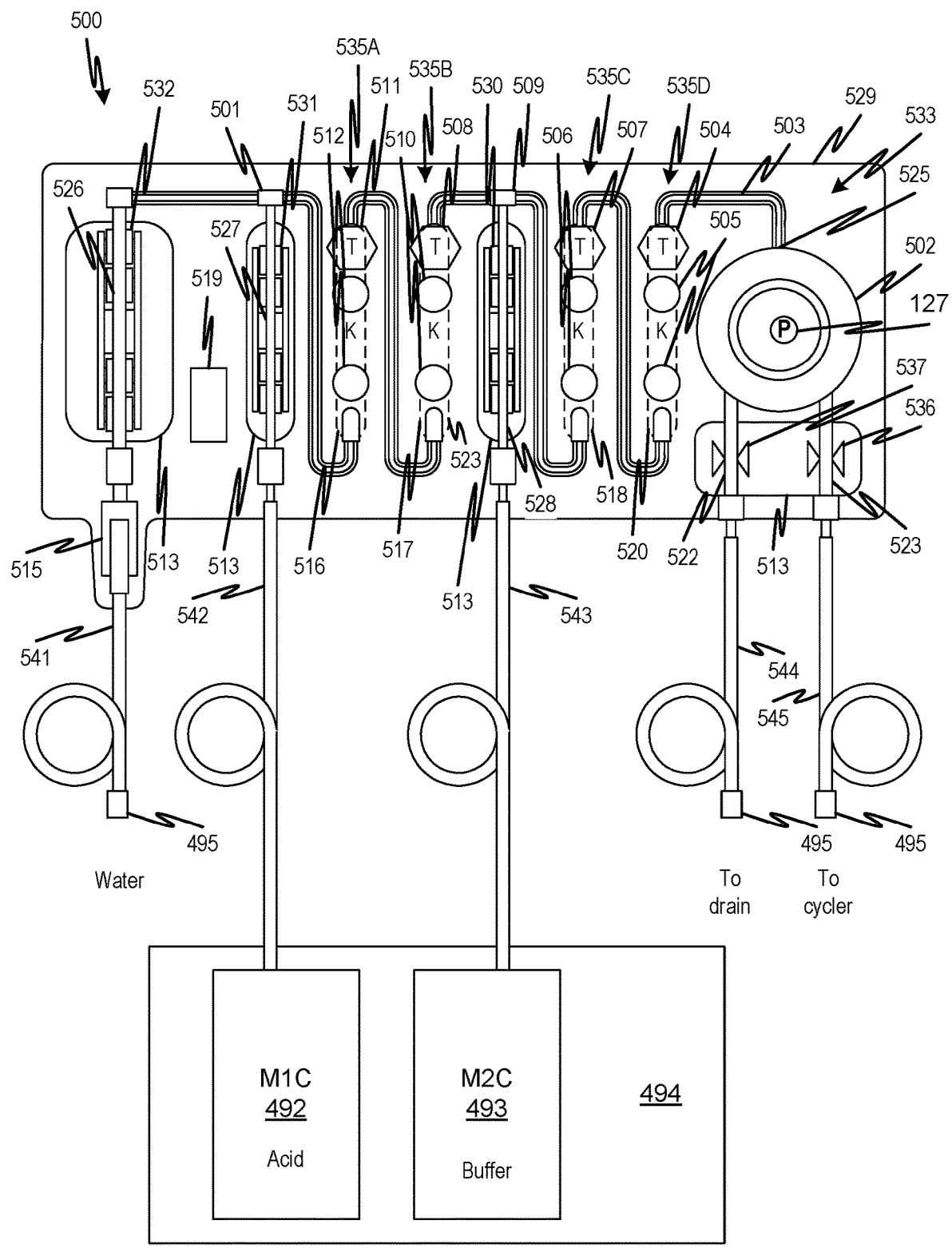
FIG. 6 shows further details of a fluid circuit cartridge according to embodiments of the disclosed subject matter.

Referring now to FIG. 6, an embodiment of a fluid circuit cartridge 500 is illustrated such as the fluid circuits of the medicament proportioning module 104 of any of the foregoing embodiments. The cartridge has a generally planar support 529 for the various fluid circuit elements. In embodiments, a fluid circuit is embodied in by a fluid circuit pattern defined in the support 529, for example by molded channels or seam welding or a combination thereof. Alternatively, the fluid circuit may be made up of discrete channel elements such as tubes, junctions, and valves. A fluid circuit 533 supported by the support 529 has channel elements 503 (indicated at 503 but also appearing at various locations as indicated), temperature measurement cells 504, 507, 508, 511, concentration measurement modules 535A, 535B, 535C, and 535D, pumping tube segments 526, 527, 528, an accumulator 502, and pinch valve tube segments 522, 523, junctions 501, 509. Cutouts 513 in the support 529 allow pumping actuators 532, 531, 530, to mechanically access pumping tube segments 526, 527, 528, respectively, and valve actuators 536, 537, to access pinch valve tube segments 522, 523, in order to pump fluid or halt or allow the flow of fluid.

Pure water enters in line 541 from a water purification module 102 pumped by pumping actuator 532 through pumping tube segment 526. An inline sterile filter 515 ensures that any touch contamination, or any contamination, does not enter the cartridge fluid circuit. Pumping tube segment 526 (as well as segments 527 and 528) may be made of a specialized construction and material that provide low material creep and precise size to allow consistent and predictable rates to be provided through the regulation of the pumping actuator 532. The rate of rotation of the pumping actuator 532 is regulated by a controller (not shown) to provide a medicament product flow required by a downstream treatment such as a flow commanded by a cycler 106 and received thereby, or some other consuming device such as storage container.

A first concentrate is received through a first medicament concentrate line 542 and is pumped at a rate controlled by the controller to provide a predefined dilution rate of the combined flow emerging from the junction 501. The mixed diluted first concentrate flows into a first concentration measurement module 535A. Each concentration measurement module 535A-535D is described in more detail with reference to FIGS. 7A through 7E, infra. The mixed diluted first concentrate flows into the first concentration measurement module 535A and contacts conductive electrodes, one of which is indicated at 512. A current is driven through a column channel of the concentration measurement module 535a and a voltage drop is measured across the conductive electrodes 512 using the conventional four-point conductivity measurement scheme in order to reduce contact resistance error. The fluid emerging from the column channel is received in a temperature measurement cell 511 and then flows into a second concentration measurement module 535B with temperature measurement cell 508 and conductive electrodes 510 (only one indicated, but the other is evident by inspection). The second concentration measurement module 535B provides a redundant indication of conductivity and temperature to confirm accuracy by agreement between concentration measurement module 535A and concentration measurement module 535B. The controller or an independent module may output a signal or data indicative of concentration based on temperature and conductivity. The signals indicating conductivity and temperature may be converted to concentration responsively to stored (in a data store of the controller—not shown separately) conductivity-temperature curves for the solution received thereby. The same is done using temperature and conductivity signals from concentration measurement module 535C and concentration measurement module 535D as well.

The diluted first concentrate is received at a junction 509 where it combines with a flow of second concentrate pumped through the pumping tube segment 528 by pumping actuator 530. The second concentrate is drawn through a second medicament concentrate line 543. The flow rate of the diluted first medicament is determined by the combined flow rates of the flows in pumping tube segments 526 and 527 which are regulated by the controller (not shown) through control of the actuator (532, 531) speeds. In a similar manner, the flow through the pump segment 528 is regulated by the rate of the pumping actuator 530 such that the concentration of the mixture emerging from the junction 509, which includes the first and second concentrates plus the dilution water, is regulated by the relative rotation rates of the three pumping actuators 532, 531, and 530. In this example, the concentration of the mixture emerging from the junction 509 represents a final concentration of product medicament and it is measured using the concentration measurement module 535C and then redundantly measured using the concentration measurement module 535D. As described above, the concentration measurement module 535C and the concentration measurement module 535D have conductive electrodes 506 and 505, respectively and temperature measurement cells 507 and 504. The conductive electrodes 512, 510, 506, 505 (each of the numerals identifying a pair of conductive electrodes) make contact with fluid in a respective one of the conductivity measurement columns 516, 517, 518, 520 (shown in broken lines indicating they are behind the fluid circuit 533 support 529).

The product medicament flows into a diaphragm chamber of an accumulator 502 which reduces flow fluctuations by expanding and contracting with the help of an urging element. Flow enters the accumulator 502 at a junction 525 and flows out through a pair of pinch valve tube segments 522 and 523, each leading to a respective outlet line 544 and 545. The outlet line 544 is connected to a drain and the outlet line 545 is provided with a connector for connection to a consuming device such as cycler 106. The cartridge 500 may be pre-connected with concentrate containers 492 and 493, capped with caps 495 so that the entire assembly is sealed from the environment, and sterilized before packaging for delivery and/or storage. The cartridge 500 may be attached to a container 494, which can be rigid, such a box such that it can be removed from the container 494 and slid onto a shelf while positioning the cartridge 500 in the medicament proportioning module 104, where the first medicament concentrate line 542 and second medicament concentrate line 543 are of sufficient length to allow them to extend between the positioned cartridge 500 and a storage for the container 494. In embodiments, the container 494 can be a cardboard box or plastic box.

Referring to FIGS. 7A through 7D, a concentration measurement module 535 as described above is now detailed according to an example embodiment. A section of a cartridge support 556 may correspond to a portion of cartridge 406, or the support 529 of cartridge 500 described above. Thus, the edges of the cartridge support 556 may be considered to extend and not be limited to the particular shape or size illustrated, the portion shown being merely a portion of a larger support structure. An inlet flow of conductive fluid enters through an inlet channel 566 molded into the cartridge support 556. A wall 567 rises from the plane of cartridge support 556 to define the channel 566. The edge of the wall 567 may be sealed with a plastic film to make channel 566 pressure-tight. Flow, indicated by arrow 564, entering the channel internal volume 557 from other parts of the cartridge support 556 leaves the channel 566 through an opening 568 where it flows into a flow column housing 575 as indicated by arrows 574, and flows from an end opposite the entry to an opening 570 in cartridge support 556, through a temperature sensing region 558. From there, the flow traverses a temperature measurement chamber 563 toward an exit channel 572 which is on an opposite side from the opening 570 where the flow entered the temperature measurement chamber 563. The flow leaves the concentration measurement module 535 as indicated by arrow 562. The temperature measurement chamber 563 and the exit channel 572 may be sealed in the same fashion as channel 566 such that the temperature measurement chamber 563 forms a flat broad chamber. A temperature transducer may be placed against the face of the film that is used to close the temperature measurement chamber 563 providing a broad contact area for accurate temperature measurement that limits edge losses that can bias the temperature measurement. In addition, a zero-flux temperature sensor can be used which actively cancels heat flux due to conduction through the major face of the temperature measurement chamber 563, providing an excellent application here because of the high sensitivity of concentration to temperature. Bosses 552 may be provided for support and additional structure and sealing competence in the cartridge support 556.

Figure 7A:
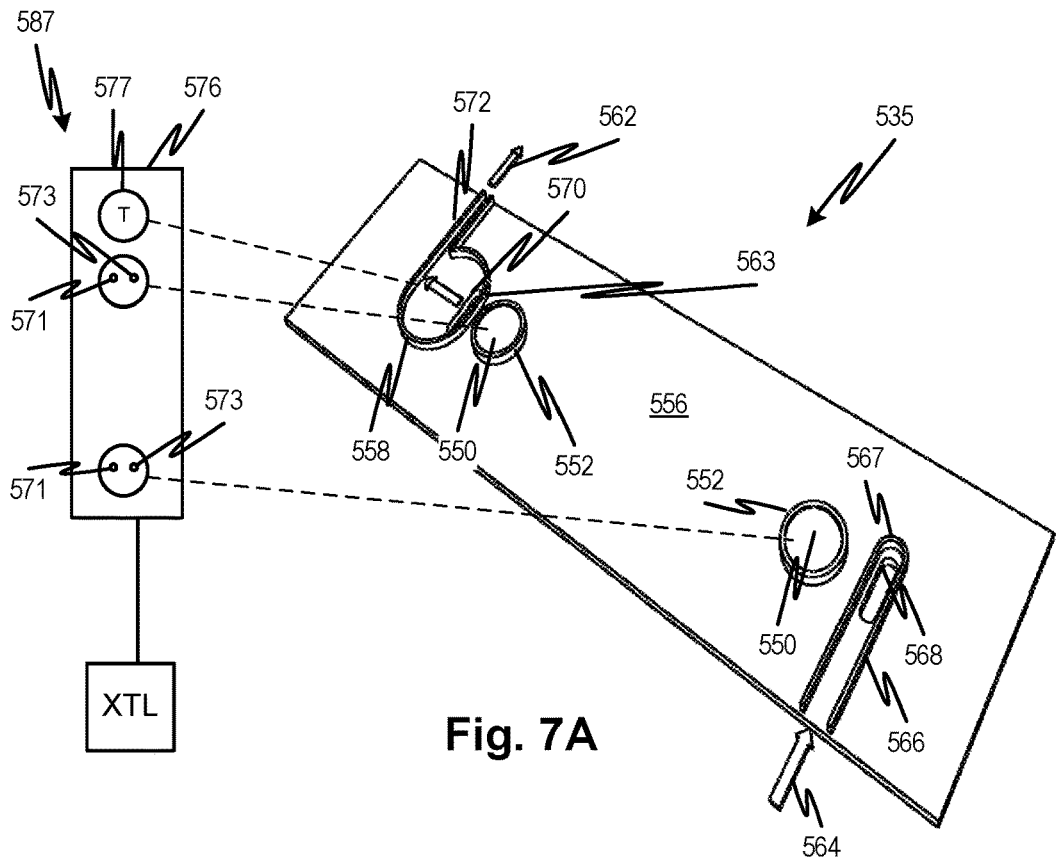
FIGS. 7A through 7E show features of a conductivity and temperature measurement cell that, according to embodiments, can be integrated in the fluid circuit cartridge of FIG. 6 and others disclosed herein, according to embodiments of the disclosed subject matter.
Figure 7B:
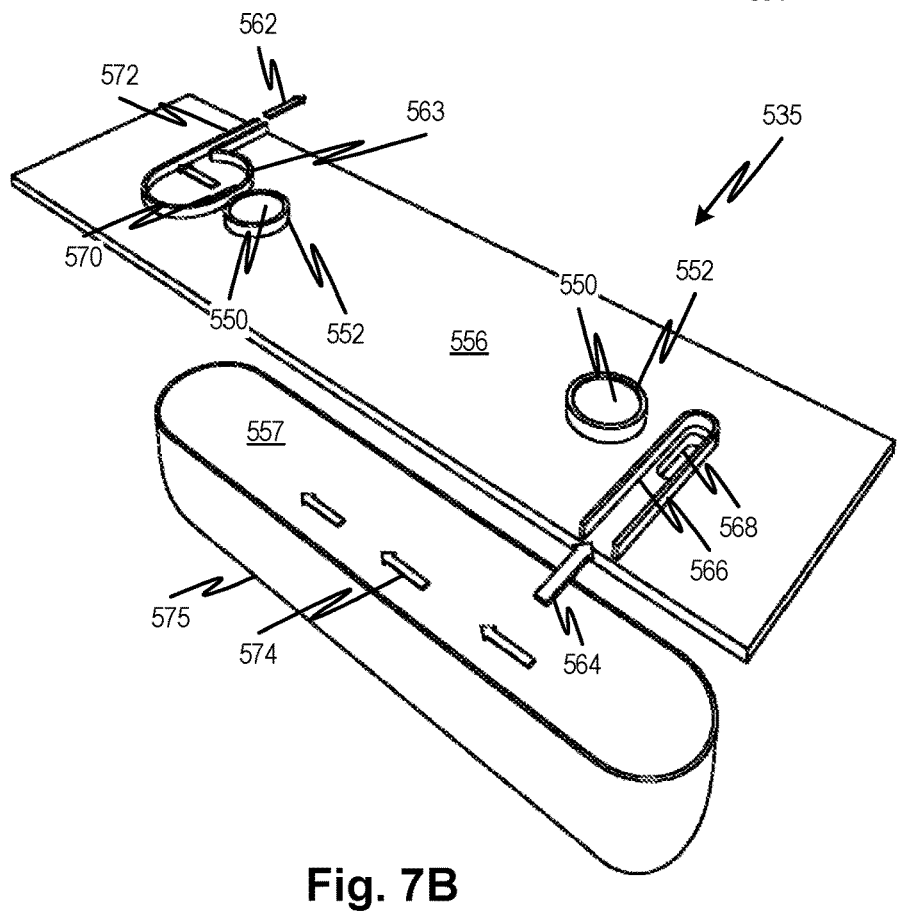
Figure 7C:
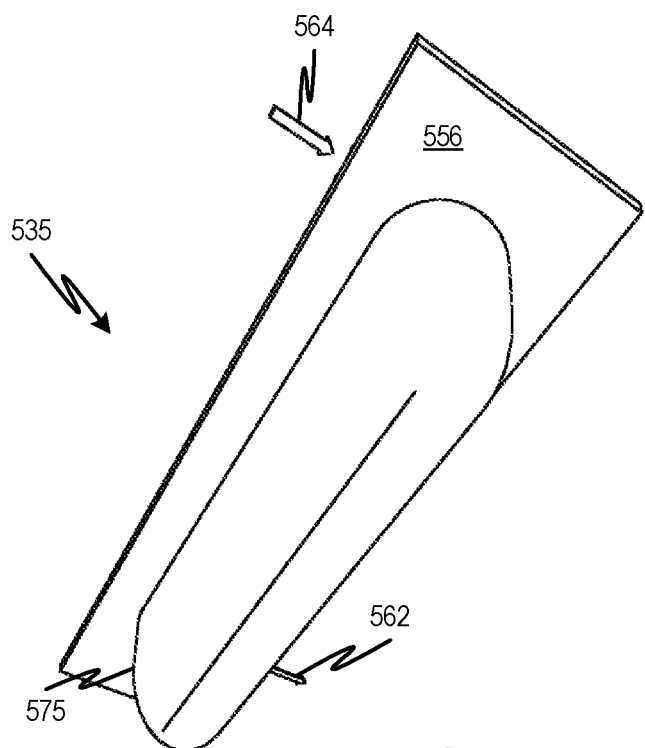
Figure 7D:
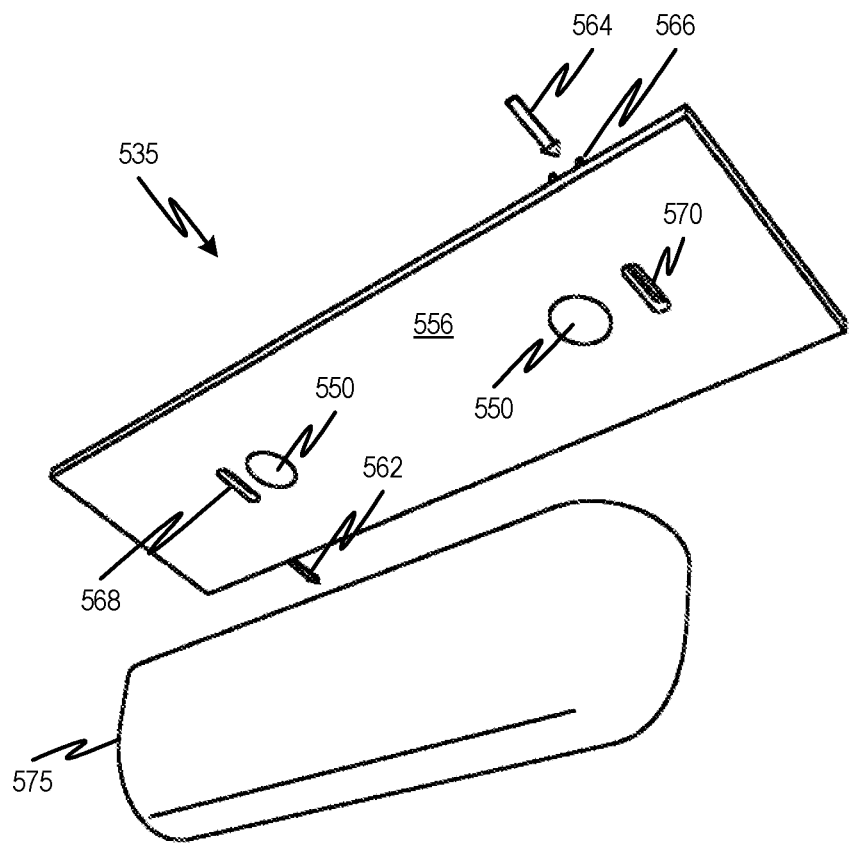

Conductive electrodes 550 may be bonded, welded, press-fitted, molded or otherwise affixed to the cartridge support 556 (a portion being shown at 576). In one embodiment, in use, spring biased contacts 571 and 573 may be pressed into each conductive electrode 550 while at the same time, a temperature transducer 577 is held against the temperature measurement chamber 563 as a sensor backplane 587 portion is held against the concentration measurement module 535 as a result of the entire cartridge being positioned in place in medicament proportioning module 104 and engaged for use. That is, when a cartridge of any of the embodiments, carrying the concentration measurement module 535 is positioned in place in a medicament proportioning module 104 and registered, the spring biased contacts 571 and 573 and temperature transducer 577 are placed against the conductive electrodes 550 and temperature measurement chamber 563 so that measurements can be taken by the connected controller. Note that FIGS. 7B and 7D are exploded views. Alternatively, elastomeric contacts may be used in place of spring biased contacts 571 and 573 as will be described in detail below.

Figure 7E:
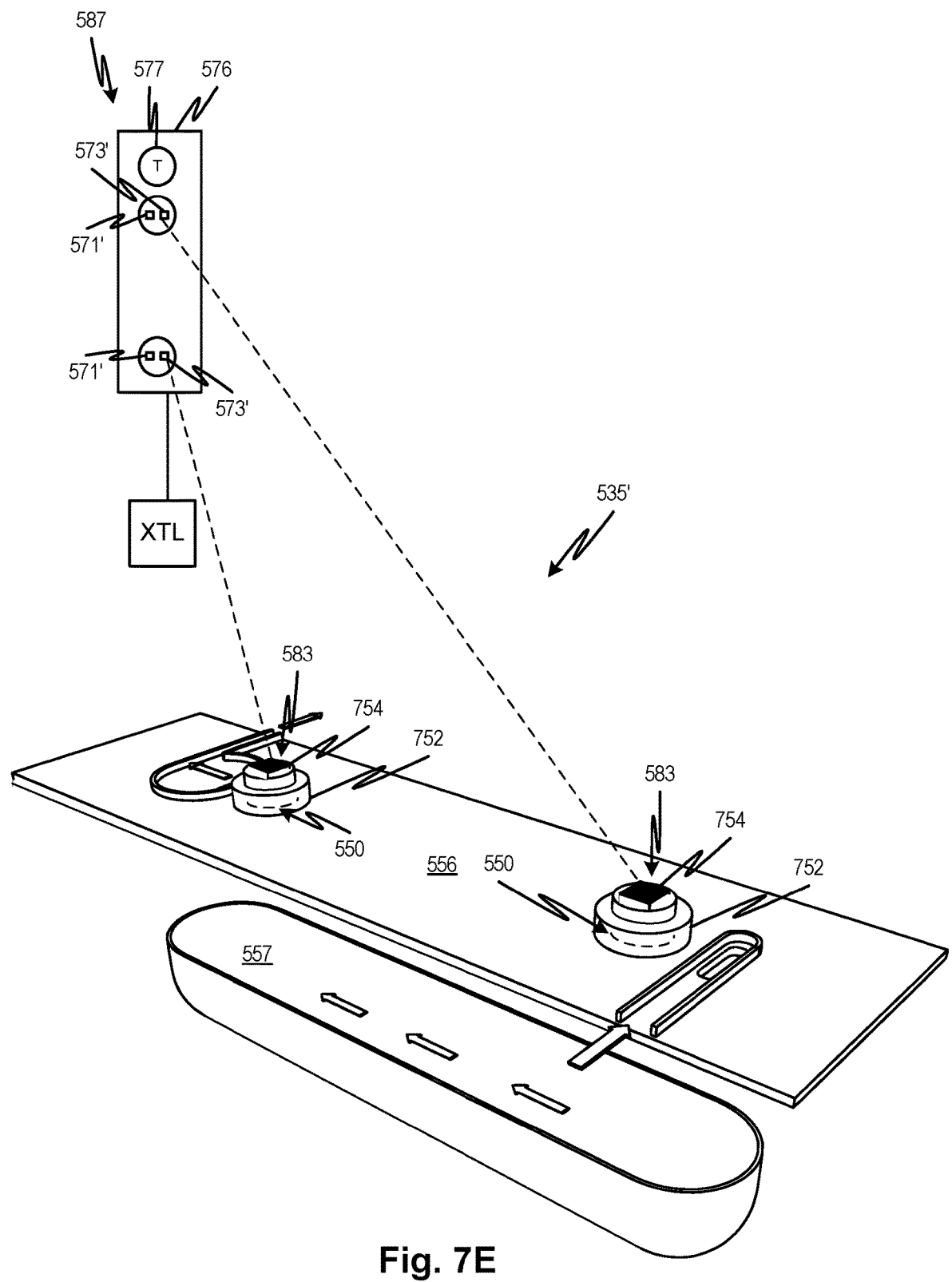

Referring to FIG. 7E, a concentration measurement module 535' similar to concentration measurement module 535 in all respects except that a compliant multiconductor device 583 is used to connect contact pads 571' and 573' to the conductive electrodes 550 shown by hidden lines. The compliant multiconductor device 583 has an elastomeric contact insert 754 partially enclosed by a housing 752. Further details are described infra. The elastomeric contact insert 754 connects contact pads 571' and 573' to respective points on the conductive electrodes 550. This replaces the contacts the spring biased contacts 571 and performs the same function with greater reliability and tolerance of manufacturing variability.

Note in any of the embodiments described herein, other types of tubing closures may be used. For example, frangible-seal valve-type closures may be used. An example of a frangible-seal valve is described in U.S. Pat. No. 4,586,928. The medicament proportioning module 104 may be equipped with an actuator to open a frangible-seal valve automatically during a set-up procedure. In a method, after installing the fluid cartridge, a linear actuator aligned with a frangible-seal valve by the positioning of the cartridge, may be controlled to open the valve in response to a command from a controller. The command may follow the complete preparation for a treatment, for example and a user input to a user interface indicating that the system should begin priming in preparation for treatment.

Note in any of the embodiments, a single sterilizing filter may be used to fill the concentrate containers of multiple fluid circuits. This may be done by connecting multiple fluid circuits to a single filter with a manifold. The latter may be sterilized prior to use. The fluid circuits connected to the filter and manifold may be sterilized after connection to prevent touch contamination from making the connection or the connection may be done in a sterile environment. The circuits may be filled and then sealed.

Figure 8A:
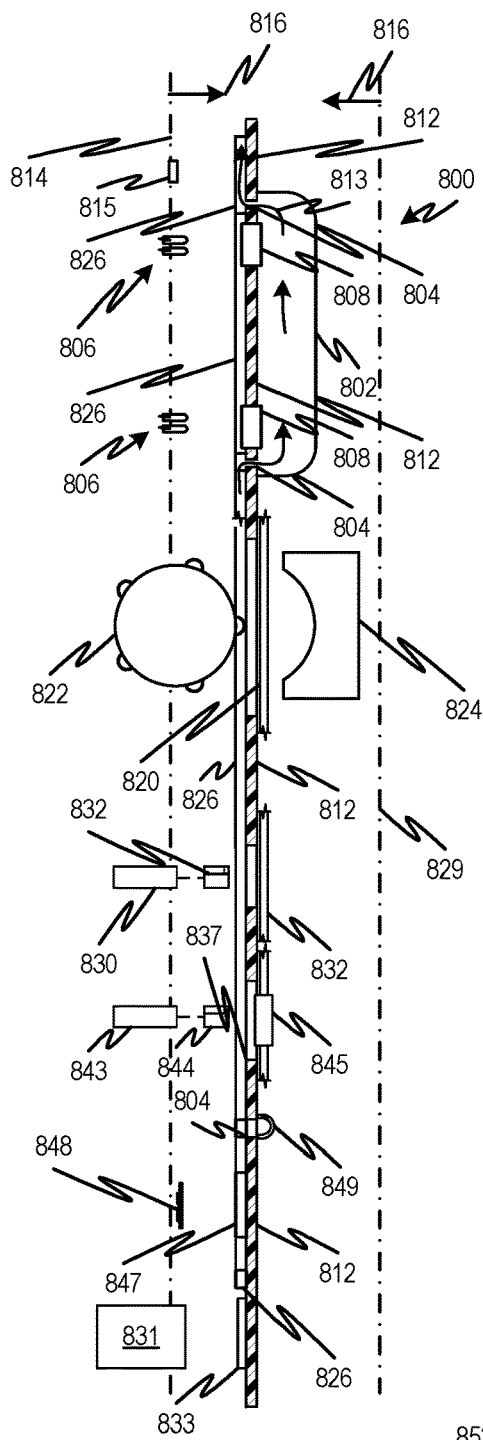
FIGS. 8A through 8C show an arrangement of elements that show how electrical, thermal, and mechanical engagement (contact) with sensor instrumentation and actuated elements can be made according to embodiments of the disclosed subject matter.

FIG. 8A shows a portion of a fluid circuit cartridge 800 to illustrate how electrical, thermal, and mechanical engagement of actuators and sensors are provided using the fluid circuit cartridge device. A fluid circuit base planar element 812, for example, injection molded plastic has molded walls that define channels 826 having a generally uniform cross section and may be covered by film by welding or adhesive. The wall extends from a base portion of the planar element forming a trough and the edges of the walls remote from the base element are then sealed with the film, fully closing the trough to form the channel. The film may be thin to minimize thermal resistance between a temperature sensor 815 (supported on a support 814) and the fluid carried by the channel 826. A channel 826 portion for engagement with temperature sensor 815 may be flattened out to reduce edge flux effects on the temperature measurement. In general, the channels 826 may be straight or curved segments that convey fluid with minimal resistance. Openings such as indicated at 804 allow the flow in the channels 826 to flow (see arrows 813) into other features such as a column channel 802 for measuring conductivity using electrodes 808 and the accumulator (not shown).

In one embodiment, the electrodes make electrical contact with contact pins 806 (which may be four in number for measuring contact resistance and for four-point measurement to minimize the effect of contact resistance on the conductance signal) also supported on an opposing planar actuator support indicated by dot-dash line along support 814 but which may be any type of support or supports. The temperature sensor 815 and contact pins 806 may be backed by urging elements such as springs.

In an alternative embodiment, instead of contact pins 806, the electrodes make electrical contact with elastomeric elements (which may also be four in number for measuring contact resistance and for four-point measurement to minimize the effect of contact resistance on the conductance signal) as will be described in detail below.

Pumping tube segments 820 can be clamped between a roller actuator 822 and a race 824, respectively supported on support 814 and an opposing support 829. A pinch clamp tube segment 832 of tubing can be positioned between clamping elements 830 supported on support 814 and clamped by a pinch clamp tubing segment. All of the engagements required are conveniently provided by moving the supports 814 and 829 in opposing directions as indicated by arrows 816 around the fluid circuit base planar element 812. Further, some of the fluid carrying features are formed by the fluid circuit base planar element 812 including the channels. Connections to the tube segments can be formed in the channel by molding as well. A tubing segment with a valve 845 such as a frangible-seal valve may be positioned to be opened at a time of set up and priming by an actuator motor 843 and actuator 844. Here the fluid circuit base planar element 812 may serve as a backstop to resist the force applied to the valve 845 or the actuator 844 may provide a clamping or scissor action that does not require an opposing support.

Another fluid circuit feature that can be formed in the fluid circuit base planar element 812 is a pressure sensor region 847, which may be formed similarly to the temperature channels 826. The overlying film provides a compliant surface that can apply force to a strain gauge 848 pressed into engagement with the overlying film of the pressure sensor region 847 when the 816 are positioned to engage the fluid circuit cartridge 800 elements. Openings 804 and elbows 849 may also be made in the fluid circuit base planar element 812 with to flow fluid from channels 826 to tubular portions such as a pinch clamp tubing segment 832, a valve 845, or pumping tube segment 820 attached at the opposite side of the fluid circuit base planar element 812.

As discussed above, the fluid circuit base planar element 812 may also support a data carrier 833 that is positioned when the cartridge is installed, to be read by a reader 831.

In embodiments, the fluid circuit base planar element 812 may be molded such that all the side action mold parts can be drawn in the same direction. In embodiments, the fluid circuit cartridge 800 may position all the sensor and actuator surfaces on one side of the fluid circuit base planar element 812. This allows all the actuators and sensors and their associated wiring and circuitry to be positioned on a first side and supported by only the support 814. The opposing support 829 can be passive. In the example shown, the opposing support 829 supports only the race 824 (a member often called a "shoe"). To facilitate tight packing of the elements, some of the larger elements such as column channel 802, pinch clamp tubing segment 832, a valve 845, and pumping tube segment 820 can be attached on the opposite side. This allows the sensors and actuators to be larger than they would be able to be if these elements were on the other side. Rather, most of the first side is flat or open. This can allow the cartridge to be much smaller than otherwise possible.

Figure 8B:
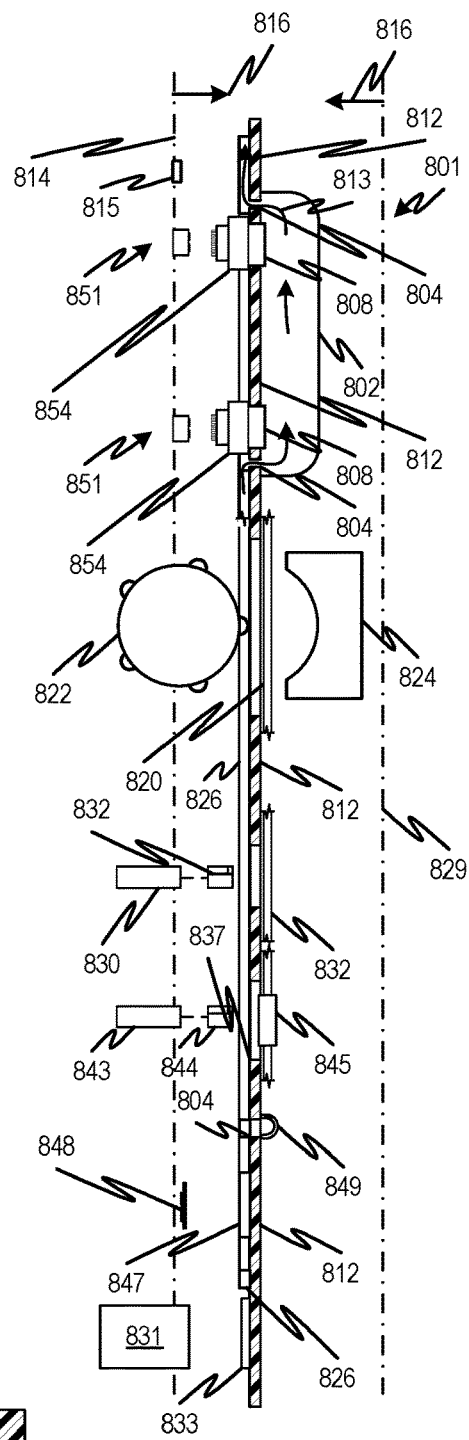
Figure 8C:
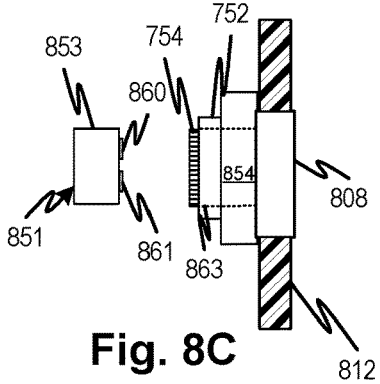
Figure 9A:
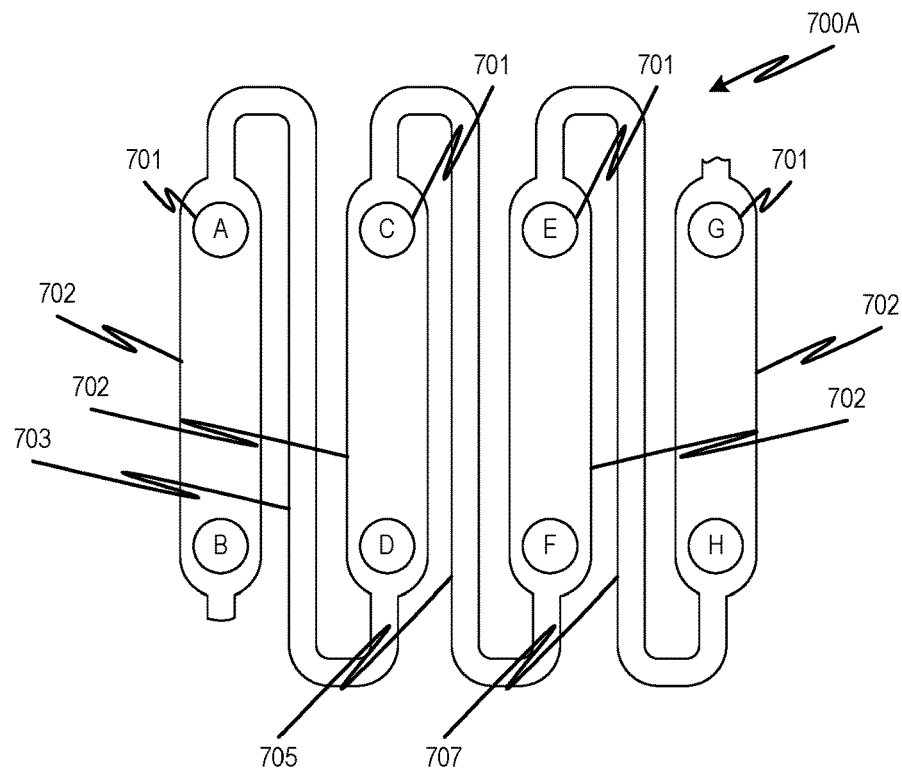
FIGS. 9A and 9B show embodiments of a conductivity measurement component that may be used with any cartridge embodiments, or substituted with equivalent conductivity measurement components thereof in any of the embodiments disclosed or claimed.
Figure 9B:
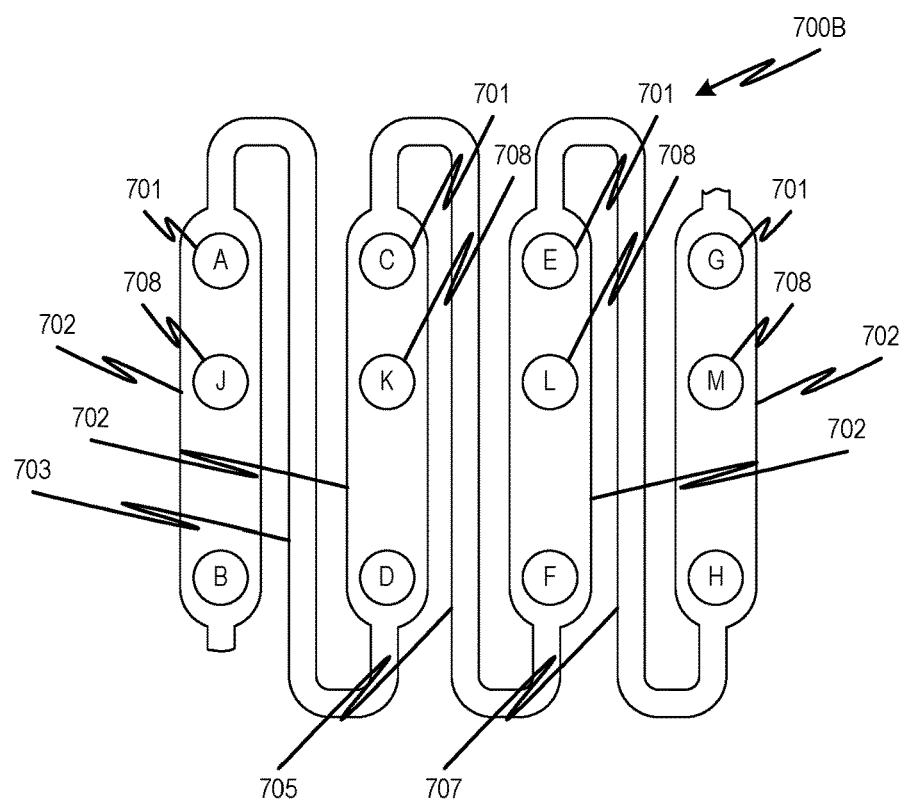

FIG. 8B shows a portion of a fluid circuit cartridge 801 similar to that of FIG. 8A except that instead of contact pins 806, the electrodes make contact with current source and voltage measurement contacts using the elements shown in FIG. 8C. FIG. 8C shows a contact device 854 according to embodiments of the disclosed subject matter. A portion of the fluid circuit base planar element 812 defines a wall of the column channel 802. The electrode 808 seals the flow space enclosing the fluid whose conductivity is to be measured. A housing 752 holds an elastomeric contact insert 754 against the electrode 808. Elastomeric contact insert 754 is shown by hidden lines at 863. The housing is attached to the fluid circuit base planar element 812 or the electrode itself by any suitable means including an interference fit, adhesive attachment, fasteners, or other means. A contact element 851 has a substrate 853 with current source 860 and voltage measurement 861 contacts. When a cartridge of which fluid circuit base planar element 812 is a part is moved relative to the other means the contact element 851, the elastomeric contact insert 754 is squeezed between the electrode 808 and the current source 860 and voltage measurement 861 contacts. See FIGS. 13A through 13D for more. The configuration avoids the need for contact pins 806. Other benefits of the elastomeric contact insert 754 and equivalents apply. Thus, the electrode 808 and other means the contact element 851 can Referring now to FIG. 9A, as in the fluid circuit 533, conductivity may be measured using series concentration measurement modules that are connected in series or series/parallel as described with reference to FIG. 5. In the present embodiment, which may be substituted into any of the foregoing or following embodiments, conductivity is measured based on multiple paths as well as the fluid column in a respective measurement column, such as columns 702. A fluid flows through columns 702 which are joined by channel elements 703. Additional channel elements may be included such as to inject concentrates or diluents as described with reference to FIG. 6. In the latter embodiment, the resistance of fluid to the flow of current was obtained between conductive electrodes at either end of a respective measurement column. In embodiments, additional measurements using the same conductive electrodes may be made. In FIG. 9A, conductive electrodes 701 are labeled A through H. Contact resistance on the dry side of each electrode may be made between current contacts and voltage sense contacts which are provided and used according to the well-known four-point resistance measurement technique. In the present embodiment, resistance is measured between multiple pairs that share a given conductive electrode 701. Not all the conductive electrodes are indicated by a reference numeral to avoid clutter, but each is labeled with a respective letter. Here, conductive electrode pair A-B is used for a resistance measurement through a respective fluid column 702. Further, conductive electrode pairs A-D and A-C are also used for a resistance measurement through a respective fluid column 702 plus channel element 703 and a respective fluid column 702 plus channel element 703 plus fluid column 702, which form respective longer fluid paths. The same may be done with conductive electrode pairs B-C, B-D, and C-D. Given known properties of the respective channels, which may be stored explicitly or tacitly (e.g., by way of a formula or look up table), the fluid conductivity can be derived from these resistance measurements. Further measurement columns 702, receiving the same fluid, may be added to provide additional fluid paths between additional conductive electrode pairs, such as A-E, A-F, E-F, E-H and so on. Additional conductive electrodes may also be added to each measurement column such as the conductive electrodes labeled J through M in FIG. 9B. In the latter example, additional conductive electrodes 708 forming pairs can be used for additional measurements of fluid conductivity, for example, A-J and A-K. Not all combinations of conductive electrodes are enumerated herein as it is straightforward to make a comprehensive list of conductive electrode pairs that can be formed with any such conductivity measurement system based on a desired number and allocation of conductive electrodes. As in the embodiment of FIG. 9A, branch lines that admit diluent or concentrate may be included at any point, of course with diminution of the number of combinations of conducting electrodes that may be available for conductivity measurement.

In the foregoing embodiments, by forming multiple electrical conduction paths through interconnected conductivity cells, using additional conductive electrodes for each measurement column, and/or by measuring across fluid paths between measurement columns, additional measurements of the same fluid conductivity or measurements that include additional variables such as the electrode "wet-side resistance," i.e., the resistance between an electrode and the fluid can be better gauged, at least for purposes of determining the reliability of a conductivity measurement. Where a resistance measurement appears faulty due to an unexpected resistance associated with an electrode, the multiple paths provide multiple equations to solve for the unknown additional resistance correction term that is used to compensate the resistance. The controller may perform these calculations automatically.

In any embodiments, an accumulator, such as accumulator 502, can be omitted and an inline pressure sensor alone may be employed thereby relying on the compliance of tubing for providing smooth pressure signals for control. The elimination or reduction in size of the accumulator may be an optimization variable. Reducing this volume may speed the synchronization process.

In any of the embodiments, including the claims, two medicament concentrates may be diluted by a medicament proportioning system or module. In these arrangements where there is concentration detection, the buffer may be diluted first and then the acid may be diluted to form a dialysate or replacement fluid product. This has benefits in that the concentration signal of the acid is stronger than that of the dilute buffer thereby causing more sensitive concentration detection.

In any of the embodiments including cycler 106, the latter may be replaced by any medicament consuming device or article such as a storage container for product medicament or a peritoneal dialysis cycler. In any of the foregoing embodiments, a pressure sensor may be positioned within an inlet or outlet of the accumulator to allow the controller to control flow through the accumulator. This may in effect be a mechanical pressure control signal from the device that demands fluid from any of the disclosed medicament proportioning system, medicament proportioning module, or other device.

In any of the foregoing embodiments, the flow channels and pumping mechanisms may be replaced with any equivalent elements adapted for fluid conveyance. They may be selected to handle flow rates in the range, in respective systems or in a single system to provide medicament to a consuming device at a rate of 25 through 400 ml/min. Any of the embodiments may be modified to provide an intermediate storage of medicament if the instantaneous demand of a consuming device exceeds the selected maximum generation rate of medicament. The medicament formed by the foregoing embodiments may be dialysate or replacement fluid for use any type of renal replacement therapy system, for example, peritoneal dialysis, hemodialysis, liver dialysis, and hemofiltration. The consuming appliance for any of the above systems may be a storage container to generate medicament to support a vacationing patient. It will be observed that in the embodiments disclosed, spent fluid (e.g., spent dialysate) from an attached cycler can be disposed of such that it never enters the medicament proportioning module 104 or any element upstream of the cycler. In embodiments, the cycler 106 is configured to prevent a backflow of fluid into the medicament proportioning module 104. For example, a check valve may be provided in-line between the medicament proportioning module 104 and cycler 106 for such a purpose.

By providing ultrapure water that has been reliably sterilized and guarded against touch contamination, it is possible to ensure against risk for a primed medicament proportioning module 104 to treat multiple patients within a long time period, in an exemplary embodiment, up to 24 hours apart. Also, the medicament proportioning module 104 may be primed and readied for a treatment to occur many hours, for example up to 24 hours, from the time of set-up.

In any of the foregoing cartridge embodiments, the cartridge may include a data carrier (e.g., 519) which may be or incorporate devices such as a bar code, RFID, smart chip, memory chip, or other device that includes data related to the concentrate or dry compound attached thereto for generation of medicament. Thus, by installing the cartridge, details related to the attached medicament concentrate can be communicated to the controller of the medicament proportioning module 104 or medicament preparation system (e.g., 600). For example, the data carrier may include data responsive to an expiration date, whether the fluid circuit attached to the cartridge has been used prior to the most recent installation, how much fluid has been generated from it, how long since it was first primed with fluid, the makeup of the concentrates attached to the fluid circuit. The pre-attachment of the concentrates to the circuit cartridge (e.g., 500, cartridge 406 and others), when the cartridge includes a data carrier that refers to information about the concentrates and other components of the fluid circuit, provides the two benefits (1) of allowing the cartridge, which may be of a types that is registered in a specific position and therefore convenient to allow for reading of data on the data carrier by means of a reader and (2) preventing contamination of fluid circuit by avoiding the need to make a new connection to combine the concentrate containers with the other elements of the fluid circuit. The precise positioning of the cartridge, for engagement of actuators and sensors therewith, can ensure predictable and reliable interaction between the data carrier and a reader co-located with the sensors and actuators. Also, the cartridge may be of a type that is convenient and relatively small, making handling easier for less able-bodied users, since the cartridge may be tethered to the heavier concentrate containers which may be placed in separate positions and, in embodiments, with less accuracy. In embodiments, a receiving support for the concentrate containers may be low down next to the floor while the cartridge receiving position may be located above that receiving support for the concentrate containers. For example the medicament concentrate disposable package, which may contain the medicament concentrates as discussed with reference to the various embodiments, is positioned on a low shelf. A slide out tray (on roller rails for example) may be provided (not shown) to allow the medicament concentrate disposable package to rested thereon so that the medicament concentrate disposable package can be pushed into position without sliding. Similarly, for the ultrafilter module and any other similar components.

The controller of the medicament proportioning module 104 or medicament preparation system 700A, 700B, or any other of the modules or systems herein described may have an identifier of one or more patients correlated with the medicament that is prescribed for that patient. The data included in the data carrier may be used by the controller to confirm that the correct fluid circuit is loaded by verifying the circuit cartridge data carrier. The control of the proportioning by pumps may be regulated to conform to the required medicament product. When the cycler is attached to the medicament preparation system (e.g., 600) or module 104, a signal communication between the controller of the medicament proportioning module 104 or medicament preparation system 700A, 700B and the attached consuming device, such as cycler 106 (e.g., see lines 124) may contain data indicating the type of medicament required, an identification of the patient, a prescription, or other information that may be correlated by any of the controller with the parameters of the connected fluid circuit as indicated on the data carrier of the cartridge and a signal indicating permitted or non-permitted component installation generated by any of the controllers. Such a signal may cause the generation of an output indication or prevent further operation of the equipment, if a non-permitted component installation is performed.

The data carrier may also establish expected reading ranges for measured concentration of medicament concentrate indicated by concentration measurement module 535A-535D. These data may be used to control the dilution rate of the respective medicament concentrates using feedback control from the concentration measurement modules or conductivity/temperature sensors in accord with the respective embodiments. Note that as used herein, a combination of a conductivity sensor and a temperature sensor may also be referred to as a concentration measurement module. The data carrier may include calibration data or data used for ensuring the accuracy of measurement using the cartridge or other parts of the fluid circuit. For example, in embodiments, the data carrier may communicate to the controller the cell constants or dimensions of the conductivity sensors of the cartridge for use in computing conductivity and thereby concentration. The data relating to disposables attached to and used with the system (e.g., water purification module 102 and medicament proportioning module 104) may be logged in a maintenance and/or procedure log for troubleshooting and service. The latter may be output by the user interface by maintenance, treatment, or service personnel. Solute concentration is used to set target conductivity values. Reading-in solute concentration allows addition of new catalogue numbers without requiring a software update.

The replaceable components used for water purification may include replaceable tagged components with data carriers permitting various similar functions as the data carriers described herein and other relevant to the cartridge. Generally, the function of the water purification module 102 (or the water purifying function of an integrated medicament preparation system), is to purify water to a same standard. However, the performance characteristics of the replaceable tagged components may vary. The control of the water purification module 102 may include determining whether the replaceable tagged component is correct for the particular water purification module 102. In embodiments, the controller may predict a total amount of fluid that may be processed before replacement of certain replaceable tagged components is appropriate.

Referring now to FIG. 9A, a conductivity measurement portion 700A of a fluid circuit includes multiple measurement columns 702 connected in series by channel elements 703, 705, 707. Additional junctions may be provided as described with reference to FIG. 10. Four pairs of conductive electrodes A-B, C-D, E-F, G-H, are shown but the number of columns and number of electrodes can vary. As described with reference to FIG. 10, each conductive electrode pair can be used for an independent measurement of a conductivity of fluid (or fluids) flowing therethrough. In the present embodiments, resistance is measured across other pairs of conductive electrodes than the pairs, A-B, for example, at opposite ends of each measurement column 702. For example, the resistance between conductive electrodes A-C and A-D as well as B-C and B-D may also be measured. With predefined channel properties between these pairs of conductive electrodes stored in a controller (or effectively stored in a lookup table or formula for computing fluid conductivity, multiple equations with multiple unknowns that include the contact resistances of the electrical contacts used to measure conductivity can be obtained.

In any of the foregoing embodiments, fluid circuits may include inline chambers (accumulators) to reduce water hammer due to interaction between interconnected peristaltic pumps. Additional lengths of tubing may also be included for the same purpose. Also, tubing diameters of pump tubing segments may be selected to minimize interaction issues which may reduce accuracy or cause breakage of circuit elements.

In any of the disclosed embodiments that measure the conductivity of a fluid by using conductivity cells, conductivity sensors, or conductivity measurement modules (e.g., 415, 416, 417, 418 in FIG. 8A, 535A-D in FIG. 6, or 535 in FIGS. 7A-7D), electrical contact with wetted electrodes (e.g., 505, 506, 510, 512 in FIG. 8A, 550, 577 in FIGS. 7A-7D, or 808 in FIGS. 8A, 8B) may be made through elastomeric contacts instead of spring-biased contacts. An embodiment of an elastomeric contact insert is shown in two oblique views 710a and 710b in FIGS. 10A and 10B, respectively. The contact insert is configured to be inserted into a housing that exposes the top side and the bottom side of the contact insert such that the top side of the elastomeric contact can make electrical contact with appropriate electrical point/points in an electrical circuit of a conductivity measurement module, while the bottom side of the elastomeric contact can make electrical contact with a wetted electrode (further details of embodiments of the housing are described below with reference to FIG. 13A and 13B). As compared to spring-biased contacts, using the disclosed elastomeric contacts allows for positional tolerance, for example, at least along the Z axis 718. Further, the disclosed elastomeric contacts are less susceptible to fluid leaks as compared to spring-biased contacts such as pogo pens. This is due to the fact that pogo pens have sliding surfaces (to slide the pen to make contact with wetted electrodes) while the disclosed elastomeric contacts include no sliding surfaces.

Figure 10A:
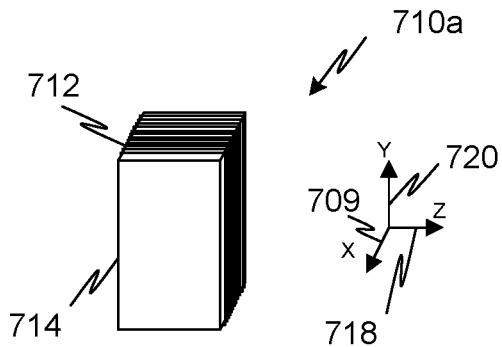
FIGS. 10A and 10B show oblique views of embodiments of an elastomeric contact insert of an elastomeric contact that may be used with a conductivity measurement component in any of the embodiments disclosed or claimed.
Figure 10B:
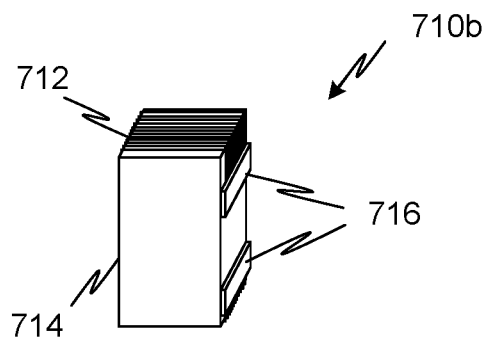

Still referring to FIGS. 10A and 10B, in one embodiment, the contact insert is formed by wrapping (along the Y axis 720 and the Z axis 718) at least a portion of an elastomeric block 714 with a parallel array of electrically conductive wires 712, where each two adjacent wires are separated by an electrically insulating material. Alternatively, the contact insert may be formed by attaching/gluing/molding a ZEBRA® connector strip (i.e., an elastomeric connector strip with alternating electrically conductive and electrically insulating regions in an elastomeric matrix) around at least a portion of the elastomeric block 714. The ends of the wires 712 may be protected by an adhesive protector 716, for example, an adhesive film. The elastomeric block 714 may be of any suitable elastomeric material such as silicon, rubber, synthetic rubber, or other material. The elastomeric block 714 is preferably of an electrically insulating material. The wires 712 may be bonded to the elastomeric block 714. The wires 712 may be of any electrically conductive material. In embodiments, the wires 712 are 0.002" in diameter and made of gold over nickel-plated copper.

Figure 11A:
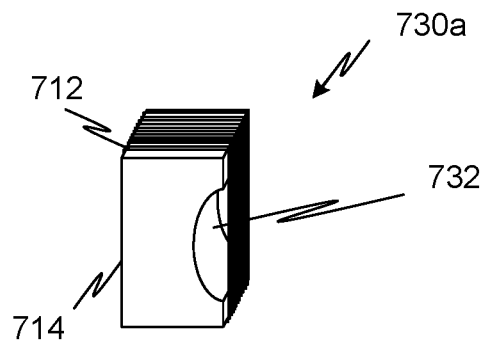
FIGS. 11A and 11B show oblique views of additional embodiments of an elastomeric contact insert of an elastomeric contact that may be used with a conductivity measurement component in any of the embodiments disclosed or claimed.
Figure 11B:
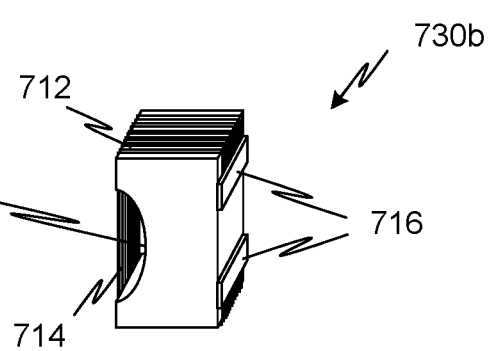

FIGS. 11A and 11B respectively show two oblique views 730a and 730b of an embodiment in which the elastomeric block 714 has a relief recess 732 that allows for improved positional tolerance along the Z axis 718. That is, the relief recess 732 permits the elastomeric block to better flex. The wires 712 span the relief recess 732 at the corresponding side of the elastomeric block 714. The shape, size, and location of the relief recess 732 in FIGS. 11A and 11B represent only one possible embodiment for improving flexibility of the elastomeric contact, and alternative shapes, sizes, locations, and numbers of relief recesses will be apparent to a skilled person in the relevant arts.

Figure 12A:
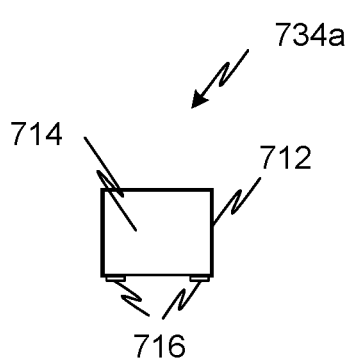
FIGS. 12A-12C show cross-sectional views of embodiments of an elastomeric contact insert of an elastomeric contact that may be used with a conductivity measurement component in any of the embodiments disclosed or claimed.
Figure 12B:
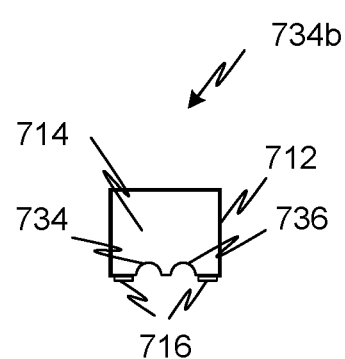
Figure 12C:
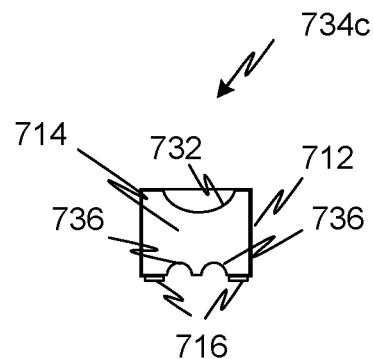

FIGS. 12A, 12B, and 12C respectively show cross-sectional views 734a, 734b, and 734c (orthogonal to the X axis 709) of example embodiments of variations of the disclosed elastomeric contact. The elastomeric block 714 of the elastomeric contact insert illustrated in FIG. 12A is solid, while the elastomeric block 714 of the elastomeric contact insert illustrated in FIG. 12B has cutouts 736 to provide springiness, and the elastomeric block 714 of the elastomeric contact insert illustrated in FIG. 12C has both the relief recess 732 and the cutouts 736 to provide better flexibility and springiness.

FIGS. 13A-13D show various views 750a, 750b, 750c, and 750d of embodiments of a housing 752 that supports an elastomeric contact insert 754 for use. More specifically, FIGS. 13A and 13B show oblique views 750a and 750b of the housing 752 with the elastomeric contact insert 754 inserted, FIG. 13C shows a cross-sectional view 750c of the housing 752 without the elastomeric contact insert 754 being inserted, and FIG. 13D shows a cross-sectional view 750d of the housing 752 with the elastomeric contact insert 754 being inserted. The housing 752 may be a block of rigid plastic or other electrically insulating material. In embodiments, the housing is of silicone. The elastomeric contact insert 754 is configured to be inserted in a receiving well 756 of the housing 752. The resilience of the elastomeric contact insert 754 allows for variations in the smoothness of the receiving well 756 to be accommodated. Adhesive may be inserted in the receiving well 756 prior to the insertion of the elastomeric contact insert 754.

In one embodiment, the elastomeric contact insert 754 and the receiving well 756 of the housing 752 are configured such that when the elastomeric contact insert 754 is inserted in the receiving well 756, the top portion of the housing 752 snugly fits the top portion of the elastomeric contact insert 754 while the bottom portion of the housing 752 is wide enough to allow for a void space being created between the inner surface of the bottom portion of the housing 752 and the outer surface of the bottom portion of the elastomeric contact insert 754.

In one embodiment, the elastomeric contact insert 754 is inserted such that a top surface 758 of the elastomeric contact insert 754 slightly protrudes from the top portion of the housing 752, while a bottom surface 760 of the elastomeric contact insert 754 slightly protrudes from the bottom portion of the housing 752.

In one embodiment, once the elastomeric contact insert 754 is inserted, an array of wires at the top surface 758 of the elastomeric contact insert 754 are configured to make electrical contact with a wetted electrode in a conductivity measurement module when the housing 752 is forced against the wetted electrode. Further, an array of wires at the bottom surface 760 of the elastomeric contact insert 754 are configured to make electrical contact with wires or printed circuit board (PCB) traces that are forced against the bottom surface 760 of the elastomeric contact insert 754, where the PCB traces may in turn be soldered or otherwise electrically connected to a sensor. As described herein with reference to various embodiments, for example, in FIGS. 13A, 13B, 13C, and 13D, each wire in the array of wires at the top surface 758 of the elastomeric contact insert 754 is electrically connected to a corresponding wire in the array of wires at the bottom surface 760 of the elastomeric contact insert 754. By pressing the top surface 758 of the elastomeric contact insert 754 against a flat wetted electrode and at the same time pressing the bottom surface 760 of the elastomeric contact insert 754 against the PCB traces, the array of wires provides redundant points of electrical contact between the wetted electrode and the sensor. Accordingly, the housing 752 and the elastomeric contact insert 754 form a contact device that is part of a fluid management system with associated electronics for completing the sensor as well as other elements.

In embodiments, the sensor may be a fluid conductivity cell of a disposable fluid circuit having wetted electrodes that are pressed against the elastomeric contact insert 754 when installed. In embodiments, the sensor may include driving and detection circuitry of a conductivity measurement electrical circuit such as a 4-terminal sensing circuit as described below with reference to FIG. 5.

Figure 14:
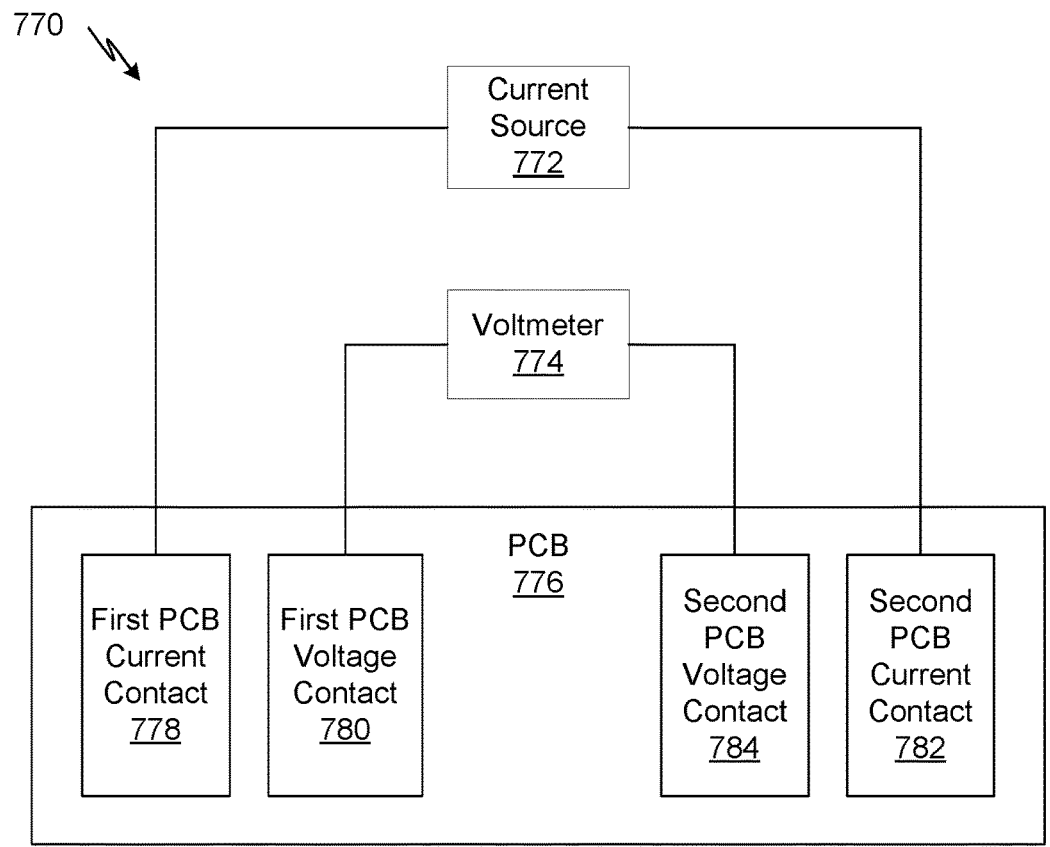
FIG. 14 shows a schematic view of various components forming a 4-terminal sensing circuit in a fluid conductivity cell that may be used in any of the embodiments disclosed or claimed.
Figure 14:
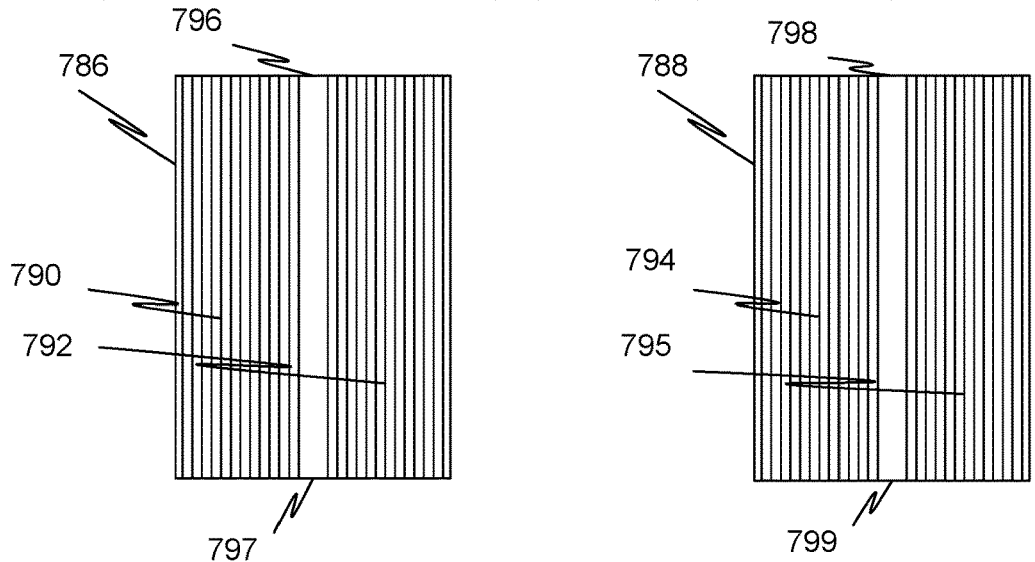

FIG. 14 shows a schematic view 770 of various components forming a 4-terminal sensing circuit in a fluid conductivity cell of a disposable fluid circuit in order to measure the conductivity of a fluid that is in contact with a first wetted electrode 773 and a second wetted electrode 771, according to an embodiment. 4-terminal sensing, also known as Kelvin sensing, refers to a method of measuring the electrical impedance between two points by driving current between the two points via a circuit formed between the first PCB current contact 778 and the second PCB current contact 782 while measuring the voltage between the first PCB voltage contact 780 and the second PCB voltage contact 784. Accordingly, since the induced current does not go through the contacts that are used for measuring voltage, the impedance of the voltage measurement contacts cannot induce errors in the impedance measurement, and the impedance measurement is insensitive to contact resistance in the current portion of the circuit.

As shown in the embodiment of FIG. 14, 4-terminal sensing is implemented by a current source 772 and a voltmeter 774 that are both electrically connected to respective electrodes in a PCB 776, where the PCB 776 is in electrical contact with the first wetted electrode 773 and the second wetted electrode 771 via a first elastomeric contact insert 786 and a second elastomeric contact insert 788, respectively. The current source 772 drives an electrical current between a first PCB current contact 778 and a second PCB current contact 782 on the PCB 776, while the voltmeter 774 measures the voltage difference between a first PCB voltage contact 780 and a second PCB voltage contact 784.

The PCB 776 is pressed or held against a first side 796 of the first elastomeric contact insert 786 and a first side 798 of the second elastomeric contact insert 788 such that:
  a first group of parallel wires 790 on the first elastomeric contact insert 786 make electrical connection with the first PCB current contact 778 on the PCB 776,
  a second group of parallel wires 792 on the first side 796 the first elastomeric contact insert 786 make electrical connection with the first PCB voltage contact 780 on the PCB 776, a first group of parallel wires 794 on the second elastomeric contact insert 788 make electrical connection with the second PCB voltage contact 784 on the PCB 776, and a second group of parallel wires 795 on the second elastomeric contact insert 788 make electrical connection with the second PCB current contact 782 on the PCB 776.

In one embodiment, the first PCB current contact 778 and the first PCB voltage contact 780 may be printed on the PCB 776 as a pair of adjacent parallel rectangular contact pads, collectively covering an area smaller in area than, or approaching the area of the first elastomeric contact insert 786 that in contact with the PCB 776. Similarly, the second PCB current contact 782 and the second PCB voltage contact 784 may be printed on the PCB 776 as another pair of adjacent parallel rectangular contact pads, collectively covering an area smaller in area than, or approaching the area of the second elastomeric contact insert 788 in contact with the PCB 776.

In the embodiment of FIG. 14, all PCB electrodes are printed on the same PCB 776. However, in alternative embodiments, the PCB electrodes may be printed on more than one PCB. For example, in an alternative embodiment, the first PCB current contact 778 and the first PCB voltage contact 780 may be printed on a first PCB, while the second PCB voltage contact 784 and the second PCB current contact 782 may be printed on a second PCB different than the first PCB. In this alternative embodiment, the first PCB is forced against the first elastomeric contact insert 786, while the second PCB is forced against the second elastomeric contact insert 788.

A second side 797 of the first elastomeric contact insert 786 is forced against the first wetted electrode 773, so that both the first group of parallel wires 790 and the second group of parallel wires 792 make electrical connection with the first wetted electrode 773. Similarly, a second side 799 of the second elastomeric contact insert 788 is forced against the second wetted electrode 771, so that both the first group of parallel wires 794 and the second group of parallel wires 795 make electrical connection with the second wetted electrode 771. As a result, the current source 772 is in effect driving a current across the fluid in between the first wetted electrode 773 and the second wetted electrode 771, and the voltmeter is in effect measuring the voltage drop across the fluid in between the first wetted electrode 773 and the second wetted electrode 771. Accordingly, fluid conductivity may be determined as a linear function of the driven current value divided by the measured voltage value.

In any of the embodiments, the PCB 776 may provide test points for measuring the integrity of the electrical connections made between the PCB electrodes, the elastomeric contact inserts, and the wetted electrodes, as will be apparent to a skilled person in the relevant arts. Also, the resistance of the connection between the contacts and a respective electrode can be confirmed by a controller by applying a current between the first or second PCB current contact and its adjacent voltage contact and measuring a voltage drop. If a resistance above a threshold level is detected, the controller may generate an error output.

Figure 15A:
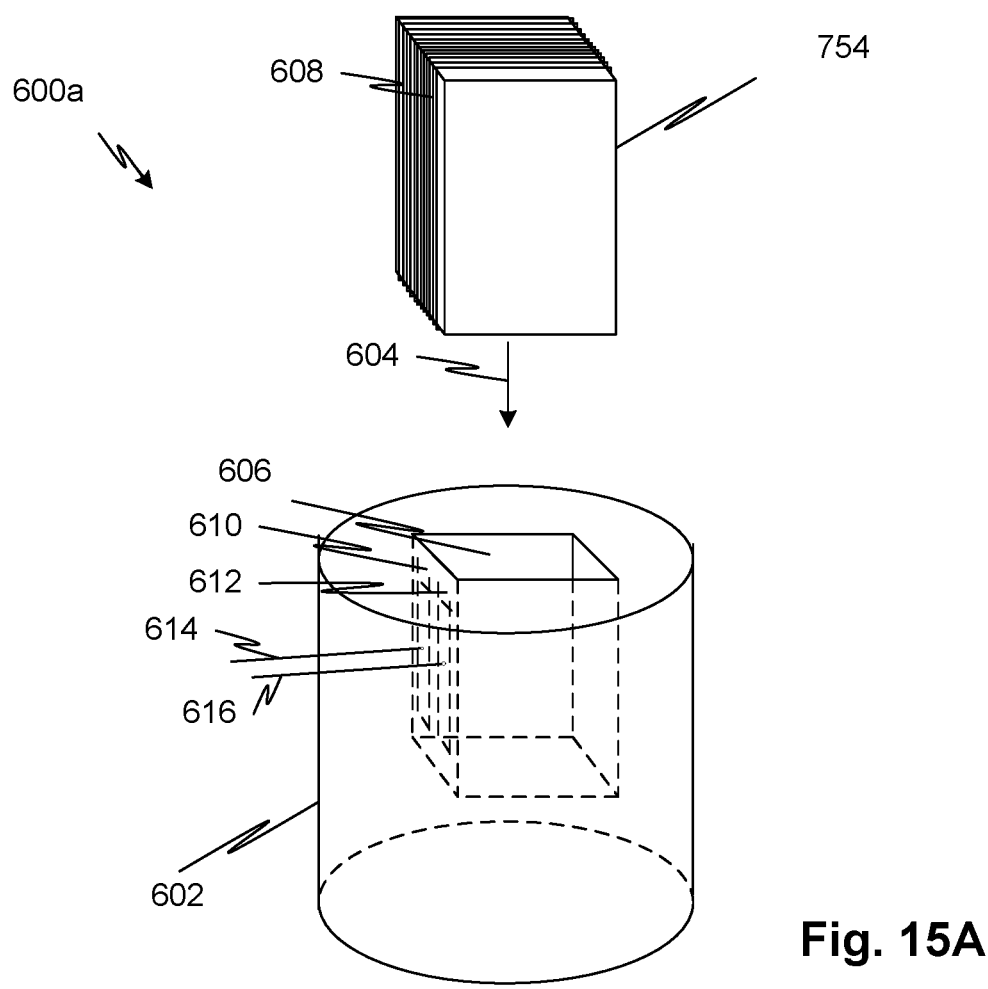
FIGS. 15A and 15B show cross-sectional views of additional embodiments of a housing that supports an elastomeric contact insert in an elastomeric contact that may be used with a conductivity measurement component in any of the embodiments disclosed or claimed.
Figure 15B:
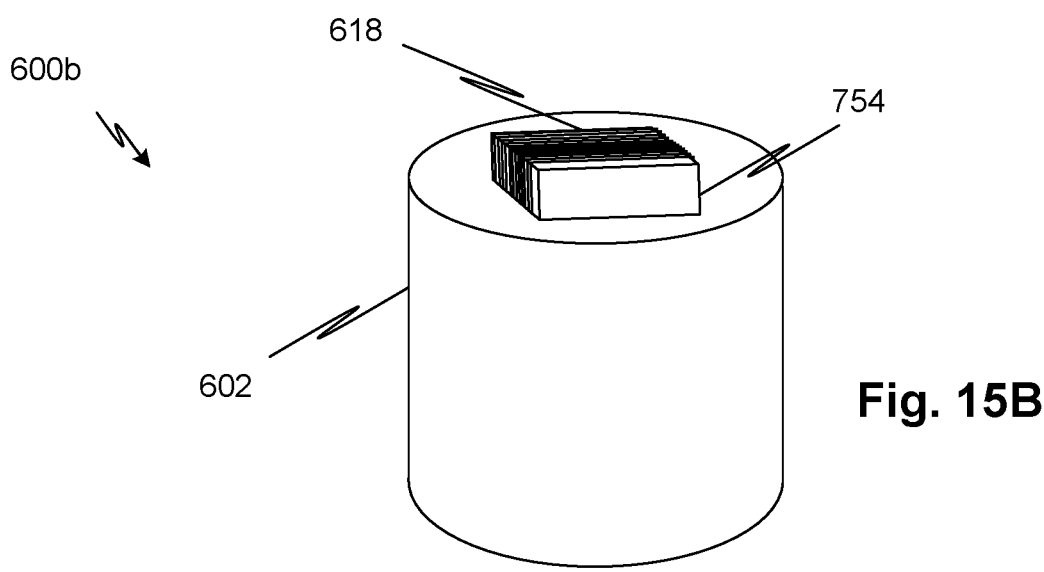

FIGS. 15A and 15B show cross-sectional views 600a and 600b of an alternative housing 602 that can support the elastomeric contact insert 754 in embodiments. The elastomeric contact insert 754 may be inserted along the direction indicated as 604 into a receiving well 606 of the housing 602. The insertion places the parallel wires 608 of the elastomeric contact insert 754 in electrical contact with a first electrical housing contact 610 and a second electrical housing contact 612 provisioned on the surface of an internal wall of the receiving well 606. A first electrical housing contact 614 and a second electrical housing contact 616 may be electrically connected to a respective one of the first electrical housing contact 610 and the second electrical housing contact 612 to provide electrical connection access to respective ones of the first electrical housing contact 610 and the second electrical housing contact 612 from outside the housing 602. The first electrical housing contact 610 and the second electrical housing contact 612 may be made of machined bores in the internal wall of the receiving well 606 of the housing 602 and may be round or have any other shape rather than being rectangular as illustrated.

Once inserted, each wire in an array of wires on a top surface 618 of the elastomeric contact insert 754 is electrically connected to a respective one of the first electrical housing contact 610 and the second electrical housing contact 612, and thus is also connected to a respective one of the first electrical housing contact 614 and the second electrical housing contact 616. The first electrical housing contact 614 and the second electrical housing contact 616 may in turn have wires or PCB traces connected to them which may then be soldered to a device such as driving and detection circuitry of a sensor as described herein with reference to various embodiment. A wetted electrode may then be forced against the top surface 618 of the elastomeric contact insert 754, thereby allowing for electrical connections to be made between the wetted electrode and both of the first electrical housing contact 614 and the second electrical housing contact 616. Accordingly, the housing configuration shown in the embodiment of FIGS. 15A and 15B may be used to implement 4-terminal sensing for fluid conductivity measurement as described herein with reference to FIG. 14.

Figure 16:
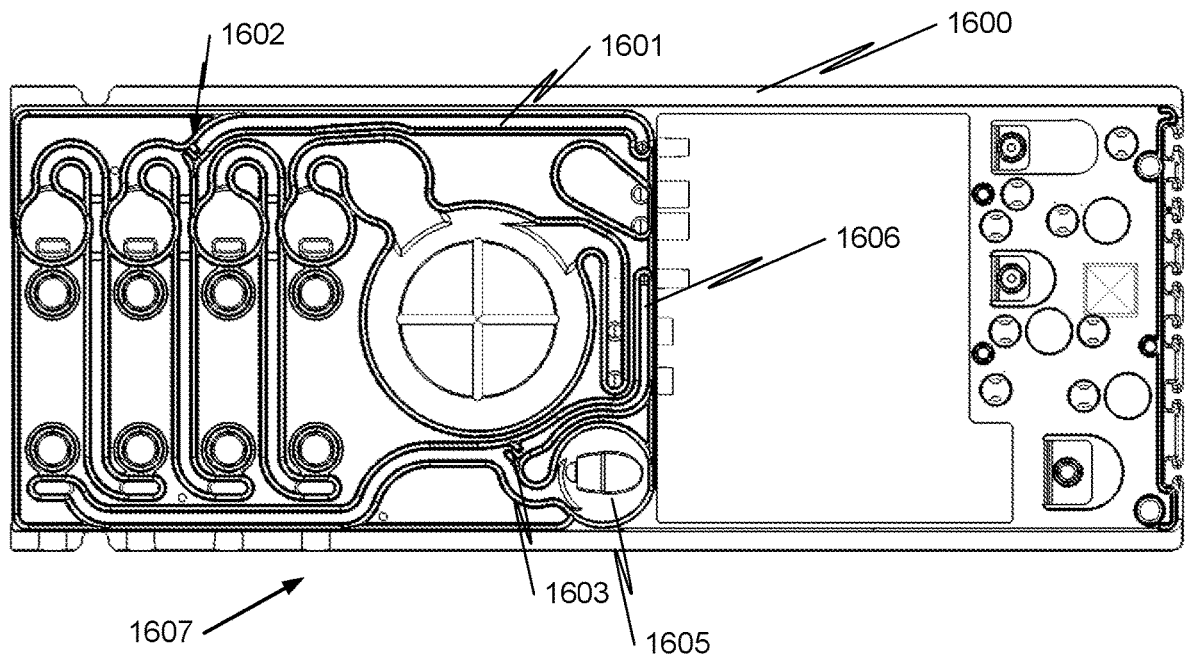
FIG. 16 illustrates a view of a fluid circuit according to embodiments of the disclosed subject matter.

Referring to FIG. 16, a medicament preparation system 1600 includes a fluid circuit 1601. In the example of FIG. 16, the medicament preparation system 1600 is formed on a cartridge of a dialysis system, but system 1600 is not limited to this exemplary embodiment. In an embodiment, the cartridge may be the same as cartridge 500 in embodiments above. Embodiments disclosed below are also applicable in non-cartridge based fluid circuits, where two flow paths come together and where it is desirable to control the quantity of fluid in each flow path.

In the example of a cartridge, the cartridge may be rigid, thus forming a rigid fluid path on or within the cartridge. Thus, the fluid circuit 1601 may be formed in a rigid structure. The cartridge may be a disposable component of a dialysis system, or may be a part of a disposable component.

It will be understood that the present disclosure is not limited to a fluid circuit on cartridge, and other types of fluid circuits 1601 are contemplated by this disclosure. The cartridge 1607 may be a disposable component of a fluid machine, such as a dialysis machine, or may be a part of such a disposable component that includes tubes and other parts. In some embodiments the cartridge may be pre-connected to container of concentrated substance such that the cartridge, the connection to the concentrate container, and the concentrate container are all sterilized together.

The fluid circuit 1601 shown in FIG. 16 may take various shapes and forms, and the particular arrangement is only exemplary. The fluid circuit 1601 includes one or more junctions 1602 and 1603, as shown in FIG. 16. The junctions are oriented in a particular position relative to the force of gravity, and the entire fluid circuit may be oriented in a predefined way relative to the force of gravity when installed in a receiving portion of a fixed machine such as a fluid preparation system (not shown). In an embodiment, when the fluid circuit 1601 is in use, such as when mixing fluids, the junctions 1602 and 1603 are positioned such that a trough or valley 1704 is formed at the lowest position of the junction. An enlarged view of an example of junction 1602 is shown in FIG. 17, and an enlarged view of an example of junction 1603 is shown in FIG. 18.

Figure 17:
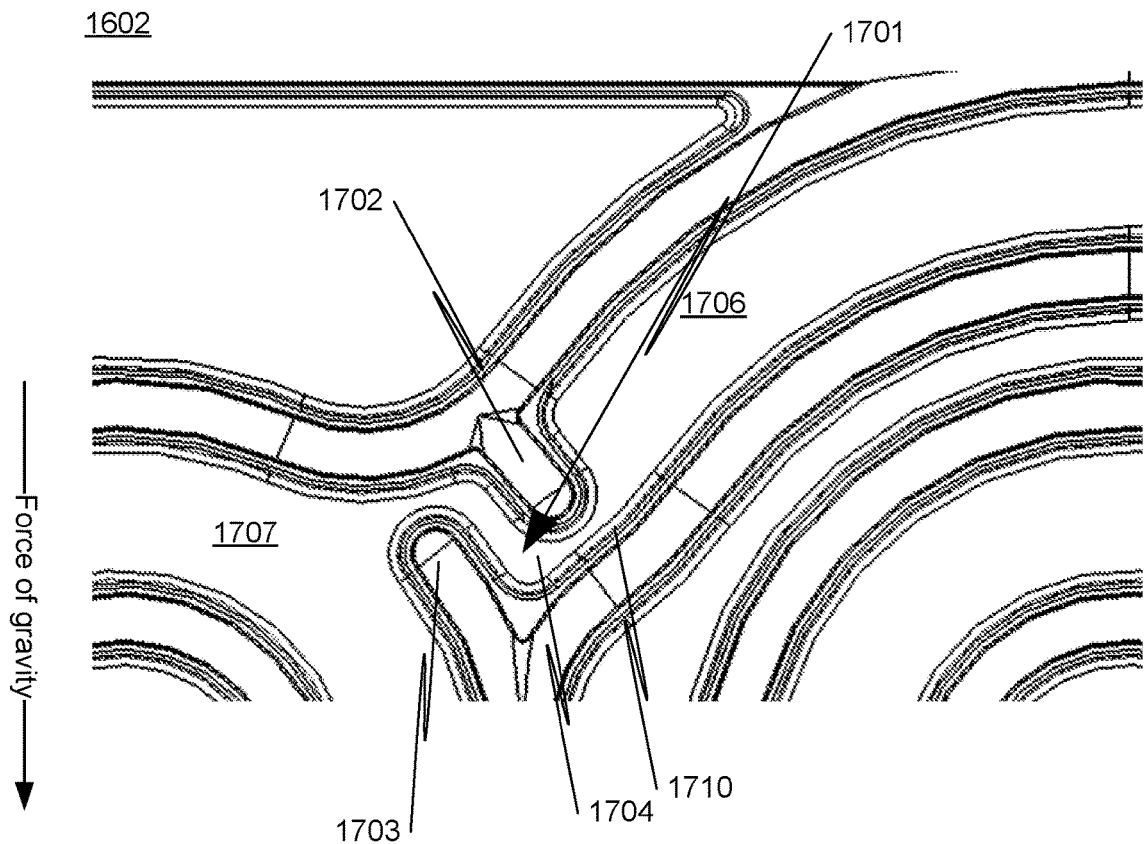
FIG. 17 illustrates a closeup view of a portion of FIG. 16.
Figure 18:
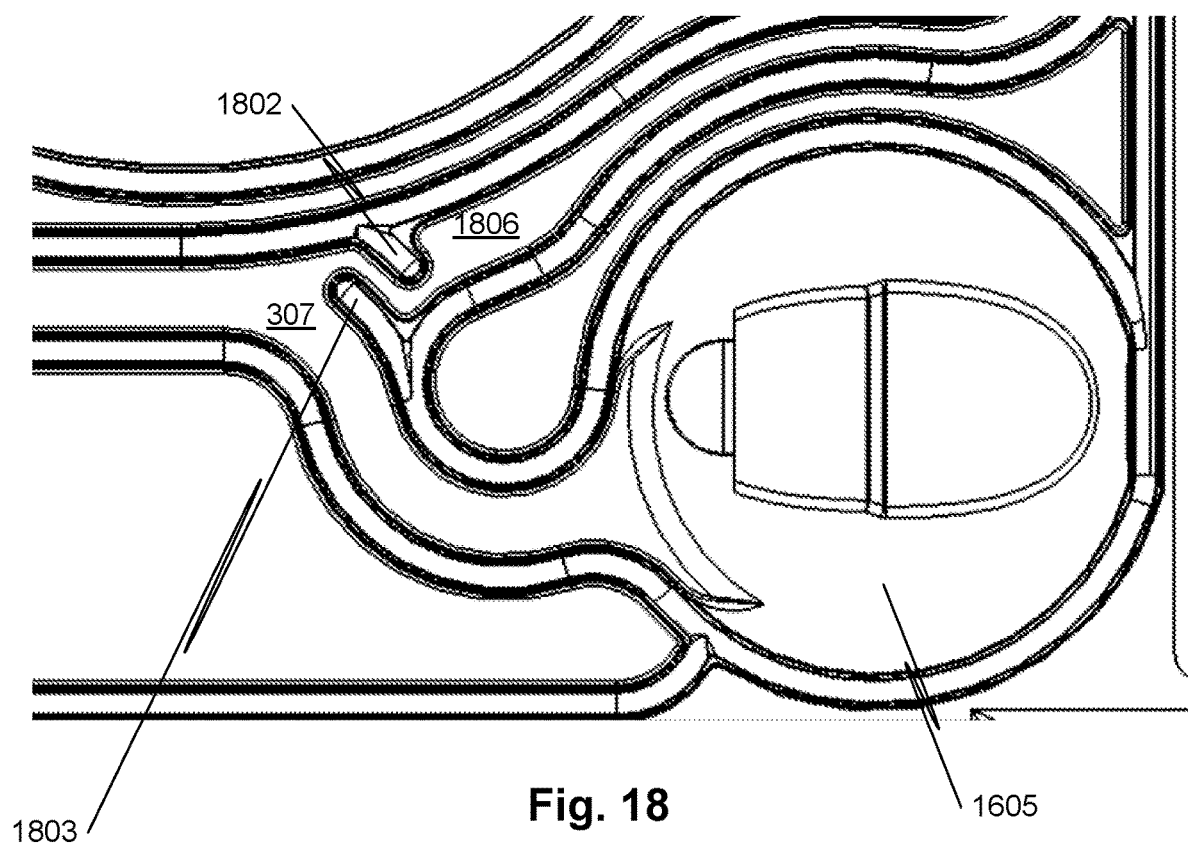
FIG. 18 illustrates a closeup view of another portion of FIG. 16.

Referring to FIG. 17, the junction 1602 may be generally "Y" shaped, where the left upper branch of the Y and the lower channel 1707 branch form common channel 1707. It is contemplated that the channel 1707 carries a fluid with a particular density. In an exemplary embodiment, the fluid is purified water mixed with some medicament. In another embodiment, the fluid is a mixture of purified water and bicarbonate. In another embodiment, the fluid is a diluted dialysate.

The upper right branch of the junction 1602 is formed by concentrate channel 1706, which carries a fluid with a density that is greater than the density of the fluid in the common channel. The relative difference in the density, together with a chicane formed in the concentrate channel 1706 and described below will be appreciated when considering the operation of the medicament preparation device. In embodiments, the fluid flowing through channel 1707 has different viscosity than the fluid flowing through channel 1706, such that the fluid in channel 1706 has a greater viscosity.

Figure 19:
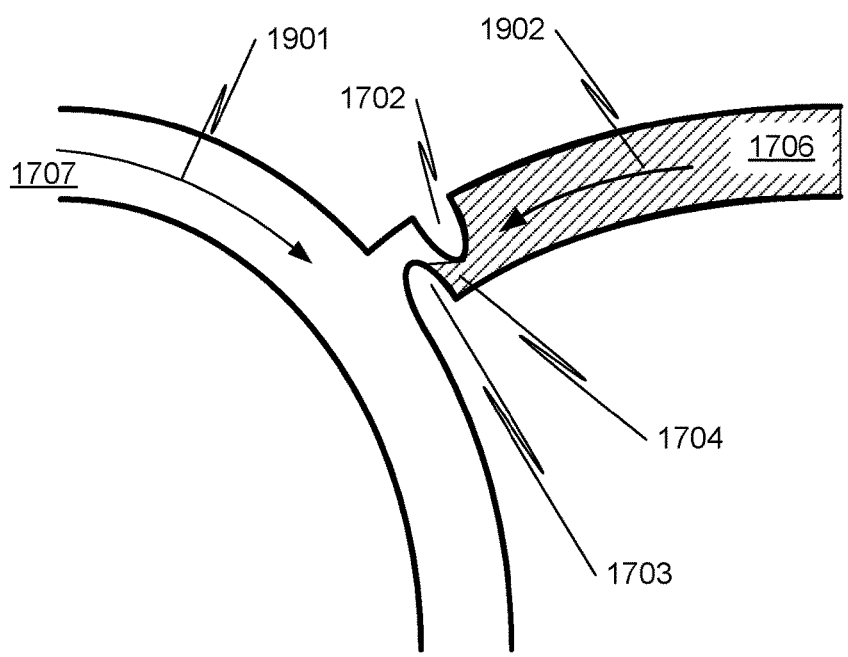
FIG. 19 illustrates a junction of a common flow channel and a concentrate channel according to embodiments of the disclosed subject matter.

As noted above, the medicament preparation system 1600 is used to create a medicament by admixing two fluids. In an exemplary embodiment, dialysate is produced by admixing purified water with a dialysate concentrate. To mix the two fluids, a mechanism, such as a pump, moves each of the fluids through the two upper branches of the junction. In some embodiments, the pump may be a peristaltic pump (not illustrated) that exerts force on a pumping segment to move the fluid(s) through the fluid circuit 1601. FIG. 19 illustrates flow 1901 of a diluent, or other fluid, in channel 1706 and concentrate flow 1902 in channel 1707.

Staying with the example of producing dialysate, channel 1707 will be filled with purified water (or water with other chemicals mixed in, such as bicarbonate). The concentrate channel 1706 will be filled with a fluid that has a higher density that the fluid in the channel 1707 (for example concentrated dialysate or acid).

As shown in FIG. 17, the concentrate channel 1706 has a chicane 1701 that curves sharply upward and then sharply downward before the concentrate channel 1706 meets the common flow channel 1707. The chicane 1701 can be created by a lower protrusion 1703 extending upward from the floor 1710 of the concentrate channel 1706 and an upper protrusion 1702 extending from the roof of concentrate channel 1706. The chicane also includes a valley 1704 as shown in FIG. 17. By providing that the higher density fluid must flow upward in order to passively flow into the common channel, the chicane acts as a fluid gravity trap.

When the common flow channel 1707 is filled with a first fluid and the concentrate channel 1706 is filled with a second fluid, and the junction 1602 is oriented as shown in FIG. 17 (relative to the force of gravity), it can be appreciated that the first fluid and the second fluid meet at the junction 1602. Because the second fluid has a higher density that the first fluid, the second fluid fills the valley 1704, but without a pumping force, will not flow over the upper edge of lower protrusion 1703 due to its higher density compared to the first fluid. In other words, the chicane 1701 prevents gravity siphoning or mixing of the second fluid into the common flow channel 1707 and concomitant mixing with the first fluid. When mixing is desired, pumping force is applied to convey the second fluid through the concentrate channel 1706 into the common flow channel 1707. Likewise, pumping force may be applied to the first fluid to accurately meter an appropriate amount of each fluid into the mixture. As shown in FIG. 16, the first fluid can come from diluent supply 1605, while the second fluid may come from concentrate supply 1606. A feature that aids in the prevention of mixing is also the diameter of the channels relative to the viscosity of the fluids. Smaller diameter tubing helps to prevent mixing when the pump is stopped.

Referring to FIG. 18, another embodiment of junction 1603 is shown. The junction 1603 is different in the shape of the upper protrusion 1802 and the shape of the concentrate channel 1806. The upper protrusion 1802 lies substantially parallel to the lower protrusion 1803, but may be oriented at other angles as well. The upper protrusion 1802 extends away from the roof of the concentrate channel 1806 at an angle, which is imposed by the shape of the roof. The height of the concentrate channel 1806 is not constant, in contrast to the concentrate channel 1706. The concentrate channel 1806 widens as it approaches the upper protrusion 1802, creating a larger cross sectional area than farther upstream. In FIG. 18, diluent is provided from diluent supply 1605 and flows left (in FIG. 18) and up. Concentrated fluid flows through concentrate channel 1806 and is admixed with the diluent when the concentrated fluid is pumped through the concentrate channel 1806.

FIGS. 19-22 illustrate schematic examples of the junctions 1602 and 1603. These figures can be thought of as cross-sectional views of the flow paths. While no particular shape of the flow channel is shown, it is contemplated that the concentrate channel 1706 and 1707 may be circular, oval, rectangular, or rounded rectangular in cross sectional shape.

Referring still to FIG. 19, the interaction between water (possibly with bicarbonate added) and an acid at a junction 1602 is shown. The water flow 1901 flows through channel 1707, while the concentrate flow 1902 flows through channel 1706. In this example, the concentrate is an acid, illustrated as a slanted line pattern. The water and acid is mixed to produce dialysate. The acid has a higher density than water, and thus remains in the valley 1704 unless sufficient pumping force is applied to the acid to raise it over the lower protrusion 1703 of junction 1602. The flow in FIG. 19 is the same as in FIG. 17, downward as indicated by arrows 1901 and 1902.

Figure 20:
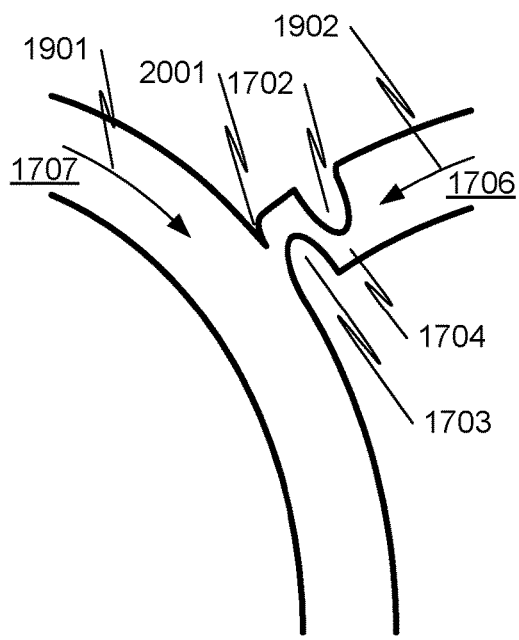
FIG. 20 illustrates a junction of a common flow channel and a concentrate channel according to embodiments of the disclosed subject matter.

Referring to FIG. 20, the junctions 1602 and 1603 may include all features of FIG. 19, and also an overhang 2001. The overhang 2001 can be provided to reduce or avoid turbulence in flow 1901 through channel 1707. As would be understood, the overhang 2001 has a sufficient length to shunt fluid in channel away from channel 1706. The length of overhang 2001 can be set based on expected flow rate of flow 1901 and the expected back pressure in channel 1706, which naturally opposes the ingress of fluid from channel 1707 into channel 1706.

Figure 21:
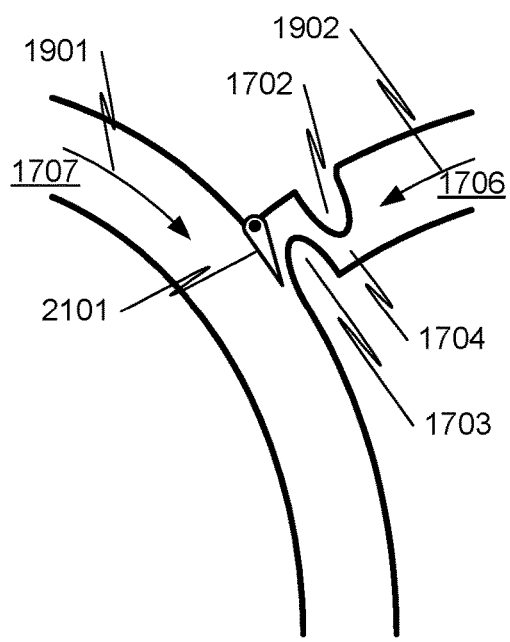
FIG. 21 illustrates a junction of a common flow channel and a concentrate channel according to embodiments of the disclosed subject matter.

Referring to FIG. 21, a flap 2101 may be added in addition or instead of overhang 2001. The flap 2101 can be biased such that biasing force keeps the flap 2101 closed until sufficient pressure builds up in channel 1706, at which point the flap permits fluid from channel 1706 to flow and mix with fluid in channel 1707. The flap 2101 is illustrated as a separate element with a hinge pin, but the flap 2101 can be molded at the same time as the flow channel, and can be made of a material that provides the necessary biasing force to keep the flap 2101 normally closed. The flap 2101 can be made of the same material as the rest of the flow channel, and the biasing force is controlled by selecting a particular thickness for the flap 2101. In embodiments, the flap 2101 can be made of a different material than the rest of the flow channel, and it is molded in a two-step molding process so that the flap 2101 can move and flex relative to the rest of the flow channel structure. In embodiments the flap is coated with a hydrophobic coating that reduces the likelihood of the concentrate from sticking to the flap 2101.

Figure 22:
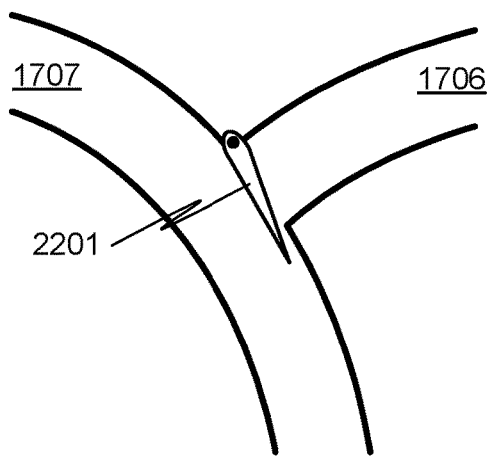
FIG. 22 illustrates a junction of a common flow channel and a concentrate channel according to embodiments of the disclosed subject matter.

FIG. 22 illustrates an embodiment where the flap 2201 may be larger than the flap 2101, and the lower protrusion 1703 is not present. The upper protrusion 1702 may also be absent in this embodiment. The flap 2201 is biased to keep the concentrate channel 1706 closed, but the biasing force is overcome when fluid in the concentrate channel 1706 is pumped toward the channel 1707.

Build-up of chemical and biological material in waste lines and drains used in medical application can require premature replacement or extensive cleaning using aggressive chemical. This is often expensive, burdensome, and can result in exposure of the user to harmful chemicals. The disclosed embodiments include devices and methods for preventing or at least delaying waste build-up that would negatively affect system operation. This is particularly important in applications where the waste fluid has high hardness that can result in calcium carbonate deposit. Examples are reverse osmosis, electro-deionization, and capacitive deionization reject water.

Figure 23:
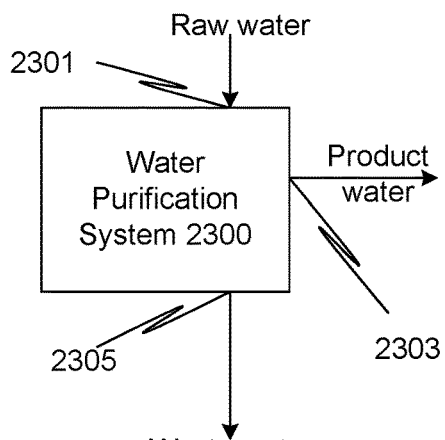
FIG. 23 illustrates a water purification system according to embodiments of the disclosed subject matter.

FIG. 23 shows a water purification system 2300 which may be based on reverse osmosis (RO) electro-deionization (EDI), or capacitive deionization (CDI) all of which are examples of purification processes that generate a waste water product that is highly concentrated in solutes and therefore subject to precipitation of solids on the internal wetted walls of the drain lines. In FIG. 1, raw input water enters the system through inlet 2301, the raw input water is purified, producing purified product water and waste water. The purified product water exits through product water outlet 2303 while the waste water exits through waste water outlet 2305. It should be understood that this discussion also applies to other drain lines, such as drain line 545 described above.

In embodiments of the disclosed subject matter, the pipe, tube, conduit, channel that conveys waste water from waste water outlet 2305 is treated to make its normally-wetted surface hydrophobic. In embodiments, a coating is a fluoropolymer of tetrafluoroethylene. In embodiments, the coating is Polytetrafluoroethylene (PTFE). In embodiments the coating may be hydrophobic and also oleophobic. This may reduce or delay scaling.

In embodiments, the drain is made to be replaced on a longer-term schedule than other fluid handling elements such as filters and fluid circuit connections. The RO (or EDI or) CDI device may have a controller that generates a reminder on a user interface to notify personnel to replace the drain line on a different (longer-term) schedule than for replacing the raw and product water handling circuit.

According to embodiments, the drain line may be treated with chemicals that prevent attachment of material to the wall of a permanent or durable (i.e., long-term-use) waste line such as tube formed with a hydrophobic material. An example is known commercially as UltraEverDry.

Figure 24:
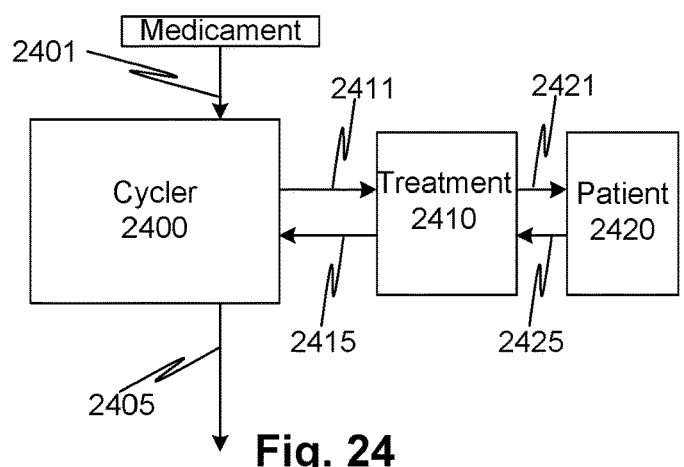
FIG. 24 illustrates a medical treatment system according to embodiments of the disclosed subject matter.

FIG. 24 shows a cycler 2400 receiving medicament through inlet 2401. This inlet is expected to be less susceptible to fouling and buildup of solutes due to the purified nature of the medicament. The cycler 2400 outputs waste fluid, which may be a mixture of the medicament and solutes that were extracted from patient 2420 during treatment, through drain line 2405. The drain line 2405, similarly to waste water outlet 2305 above, is at an increased risk of fouling and material buildup. As shown in FIG. 24, treatment device 2410 receives medicament from cycler 2400 through inlet port 2411, conveys the medicament to a consumer process (that may be connected to patient 2420) through patient access 2421 and receives waste fluid through drain line 2425. The waste fluid is returned to the cycler through drain line 2415. In many treatments, such as peritoneal dialysis or hemodialysis, the waste fluid may contain organic material from the patient such as shed cells and proteins in spent dialysate. The organic material is susceptible to fouling and sticking to the drain lines that convey it. To mitigate such effects, one or more of the drain lines 2425, 2415, and 2405 can be coated with a hydrophobic and/or oleophobic coating as discussed above. In an embodiment, only drain line 2405 is coated with the hydrophobic and/or oleophobic coating, as it may be reused multiple times, while the drain lines 2425 and/or 2415 may be replaced at a greater frequency when those lines are a part of a disposable fluid circuit used in medical treatments. In an embodiment, the drain lines 2425 and 2415 are connected to the cartridge 1607, such that those drain lines are only used for the same number of treatments as the cartridge 1607. It is envisioned that the cartridge 1607 can be used a single time for a treatment, such as hemodialysis of peritoneal dialysis, and then can be disposed, along with the drain lines 2425 and 2415.

In other embodiments, the drain line's wetted surface may be provided with texturing (not illustrated) that prevents adhesion such as nano or micro textures known to have such effect. The texturing can be applied instead of, or in addition to, the hydrophobic and/or oleophobic coating. Biomimetic surfaces that mimic the surfaces of butterfly wings and shark skin have demonstrated such properties.

Figure 25:
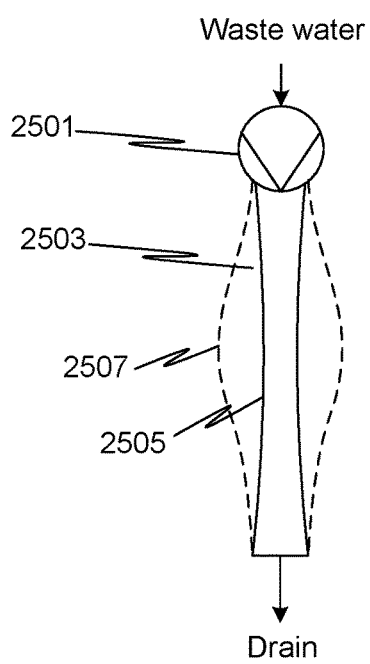
FIG. 25 illustrates a waste water line according to embodiments of the disclosed subject matter.

Referring now to FIG. 25, in further embodiments, the waste water outlet 2305 and drain line 2405 can be made of elastic tubing 2503 that contracts and expands with pressure. The contracted state 2505 is shown with a solid line, while the expanded state 2507 is shown with a broken line in FIG. 25.

The contraction and expansion of the elastic tubing changes the shape of interior of the tubing and hence breaks deposits off the inner wall of the tubing. A pump 2501 having a characteristic that generates pressure pulses may be provided and connected to such a tube to cause the expansion and contraction and thereby prevent scale buildup. The drawing is not to scale, and the effect of the contraction does not necessarily occur in the center of the tubing 2503, but can be spread along the entirety of the tubing. For example, the pump 2501 can generate pulses at a specific frequency that may generate a standing wave in a particular length of tubing 2503, such that expanded and contracted regions alternate along the length of the tubing 2503.

Figure 26:
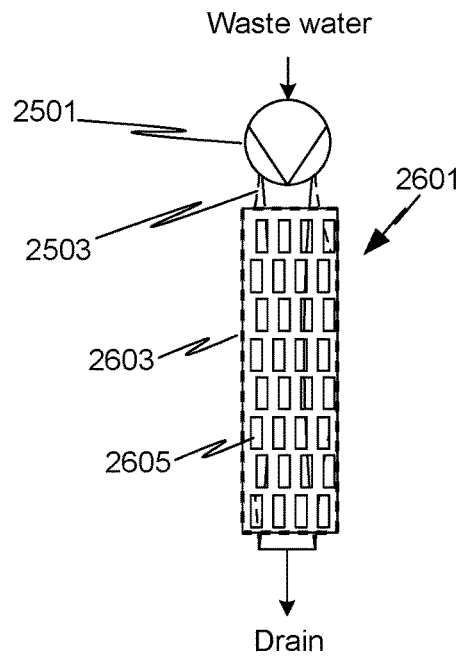
FIG. 26 illustrates another waste water line according to embodiments of the disclosed subject matter.

Referring to FIG. 26, the flexible tubing 2503 can be supported in a rigid support 2601. The support 2601 may not be completely rigid, but it is less elastic than the tubing 2503. As shown in FIG. 26, the support 2601 may include a body 2603 with cut-outs 2605, which provide visibility into the support 2601 and may also reduce the weight of the support 2601 and reduce manufacturing costs by reducing the amount of material needed.

FIG. 26 shows pump 2501 as in other embodiments, but the pump may be omitted and instead a different mechanism or force generator can apply force to the tubing 2503 to cause its movement and change of shape within the support 2601. In an embodiment, the mechanism may apply a twisting force to the tubing 2503, which will cause the tubing to collapse onto itself, but then return to the original shape when the twisting force is reversed. This can be thought of as wringing the tubing 2503, and can be applied periodically or whenever the flow rate through the tubing 2503 is reduced. To this end, a flow rate monitor (not shown) may be provided to measure and report the flow rate to a controller, which determines when to take steps such as wringing the tubing or operating the pump 2501.

Figure 27:
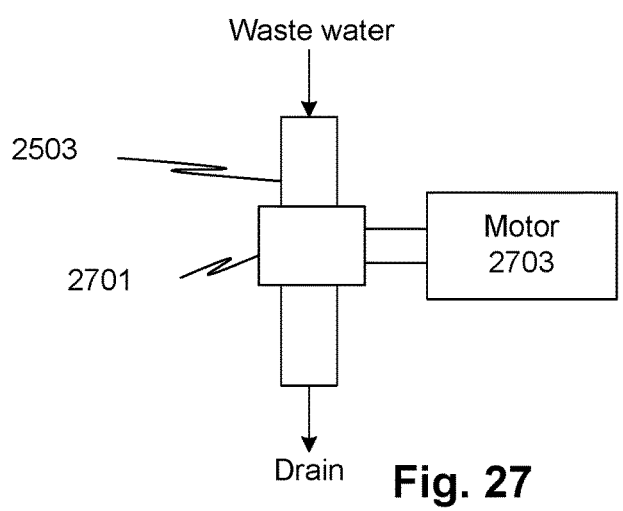
FIG. 27 illustrates another waste water line according to embodiments of the disclosed subject matter.
Figure 30:
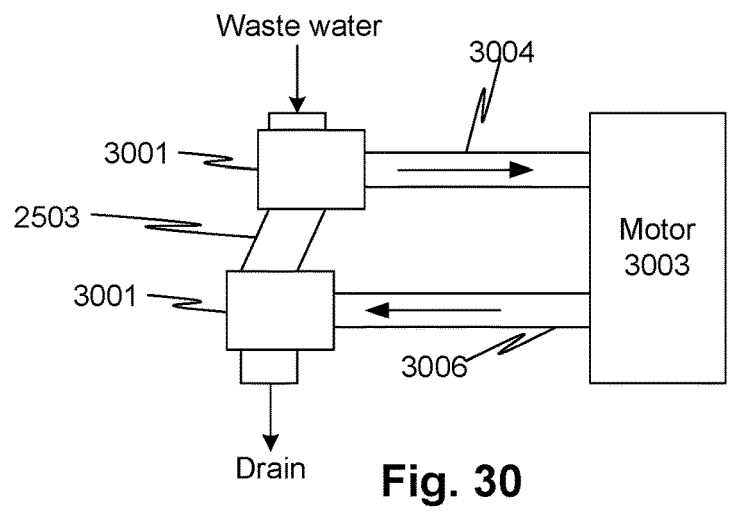
FIG. 30 illustrates another waste water line according to embodiments of the disclosed subject matter.

Referring to FIG. 27, in an alternative embodiment, an active device such as a vibrator or an actuator bends or vibrates a flexible drain tube periodically to prevent or remove scaling. Tubing 2503 passes through holster 2701. While only a single holster 2701 is illustrated, multiple such holsters 3001 can be provided, as shown in FIG. 30.

A motor 2703 can be a linear motor that moves the holster 2701 fore and aft to cause bending of the tubing 2503. If multiple holsters 3001 are provided, they can move in opposite directions and be driven by motor 3003 through multiple drive shafts 3004 and 3006. The drive shafts 3004 and 3006 may move in opposite directions to cause the tubing 2503 to flex in opposite directions to dislodge any accumulated or adhered on fouling matter. Alternative, a single motor 2703 can be linked to the multiple holsters 3001 by a cam-shaft system (not shown) to cause the alternating fore-aft movement.

In further embodiments, the drain channel 2815 is selectively flushed with deionized water to reduce scaling and minimize the possibility of bacterial or fungal growth. The drain channel 2815 may be permanently connected to the proportioning or treatment system 2800, as opposed to being a component of a disposable unit. This embodiment may be implemented for example in a system that consumes deionized water such as a medicament admixing system shown in FIG. 28. Here concentrates C1 and C2 are admixed to form a product fluid. Ultrapure water is pumped through a common line, and may be provided from product water outlet 2303 of the water purification system 2300. Concentrate, or partially or incompletely mixed, medicament may be selectively directed along channel 1707 to the drain for testing by a sensor 2810 under control of a switch valve 2805 controlled by a controller. At intervals, the control valve may divert pure water from the ultrapure source to the drain to flush it.

Figure 28:
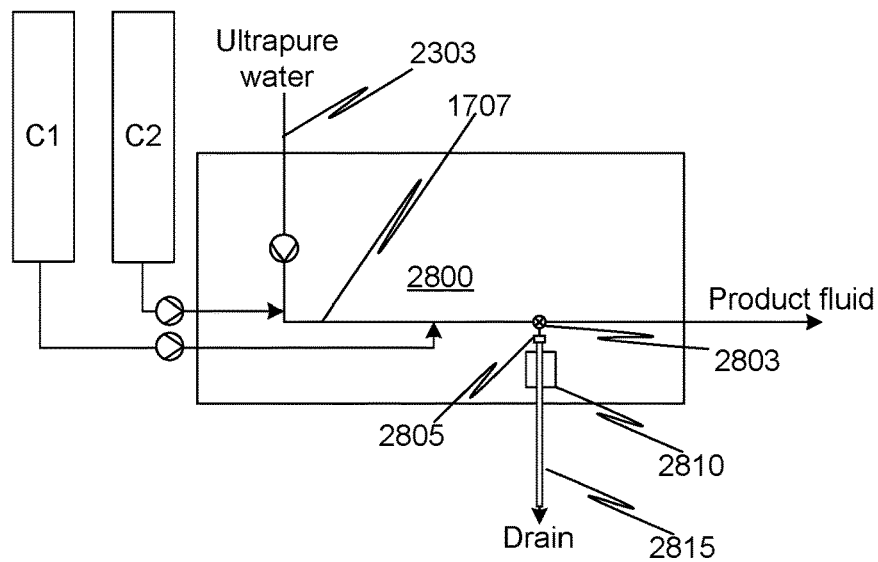
FIG. 28 illustrates a medicament admixing system according to embodiments of the disclosed subject matter.
Figure 29:
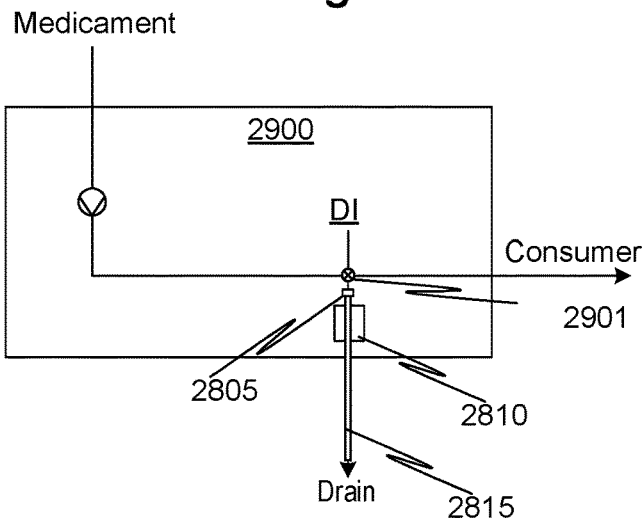
FIG. 29 illustrates another medicament admixing system according to embodiments of the disclosed subject matter.

Referring to FIG. 29, flushing deionized water may be done in a system 2900 that does not ordinarily consume ultrapure water for other purposes by providing a source of deionized water (DI) connected to a control valve 2901 and used to flush a drain in the same way, as shown in FIG. 28.

Figure 31:
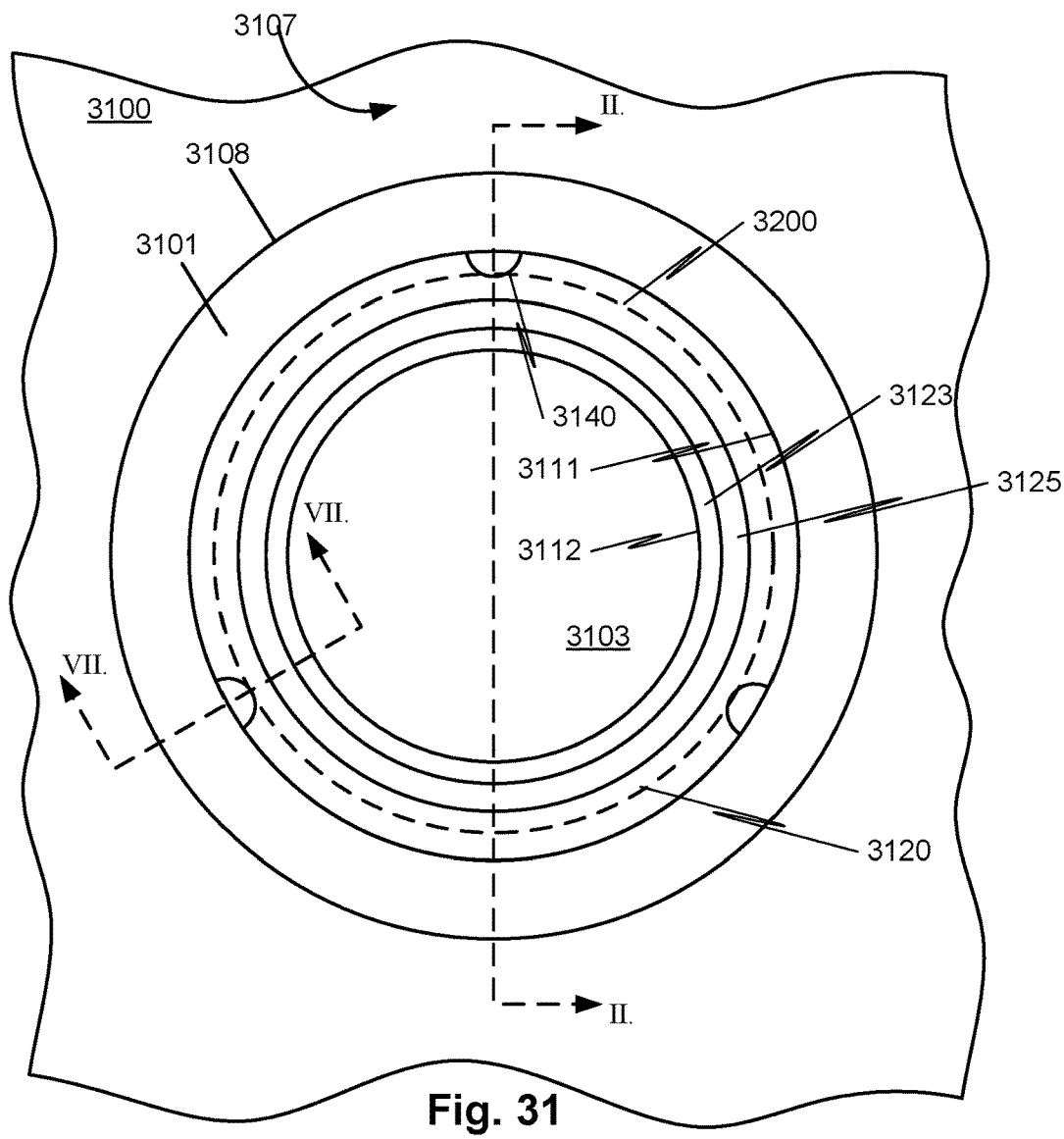
FIG. 31 illustrates a view of an opening of a housing of a conductivity sensor according to embodiments of the disclosed subject matter.

Referring to FIG. 31, a view of housing 3100 opening 3112 is shown. This type of a housing could be a part of the cartridge 500 and used to securely position a conductivity sensor. The housing may be a portion of a flow through channel, a chamber, or any element that confines a determined volume of a fluid whose conductivity is to be measured. The housing 3100 may be a part of a fluid circuit, for example one taking the form of a disposable cartridge for a medical treatment device. For purposes of this disclosure, the specifics of the housing as a fluid containment device are not essential to understanding the structures related to the assembly of an electrode 3200 to it including a stepped opening 3103 that secures and seals an insertable electrode 3200.

Figure 32:
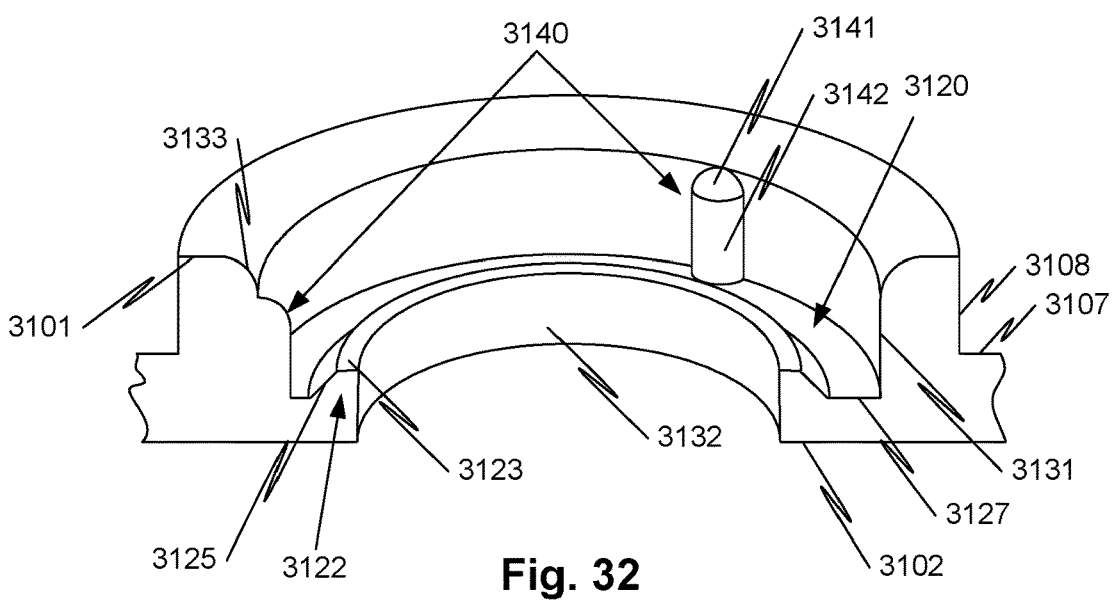
FIG. 32 illustrates an axial section of the embodiment of FIG. 31 taken along plane II-II.

Referring now also to FIG. 32, which illustrates a cross-section view of the housing viewed along plane II-II in FIG. 31, opening 3103 is defined by riser 3108 extending axially from the housing 3107. In some embodiments the riser 3108 may be omitted or reduced in size, such that the opening 3103 is defined in the housing 3107 outer surface. In other embodiments, a riser may extend into an interior of the housing 3107. The rise has a top surface 3101 that surrounds the opening 3103. In the illustrated embodiment the overall shape of the stepped opening 3103 is circular, but the opening may have other shapes as well, as illustrated in the embodiments in FIGS. 34-36, infra.

Referring again to FIG. 32, the top surface 3101 defines the opening 3103 which may be seen from FIGS. 31 and 32 to be stepped defining an outer opening portion 3111 an inner opening portion 3112. The outer opening portion 3111 is larger than the inner opening portion 3112. The outer opening portion 3111 may have a rounded lip 3133 that forms a progressively narrowing entry to the outer opening portion 3111 from the riser top surface 3101 to a sidewall 3131 of the outer opening portion 3111. In embodiments, the axial section profile of sidewall 3131 may be perpendicular the cross-section profile of the riser top surface 3101, as shown in FIG. 32. However, in other embodiments, the axial section profile of the sidewall 3131 may be sloped. In addition instead of the rounded lip 3133, the entry to the outer opening portion 3111 may be beveled or simply step-shaped.

Figure 37A:
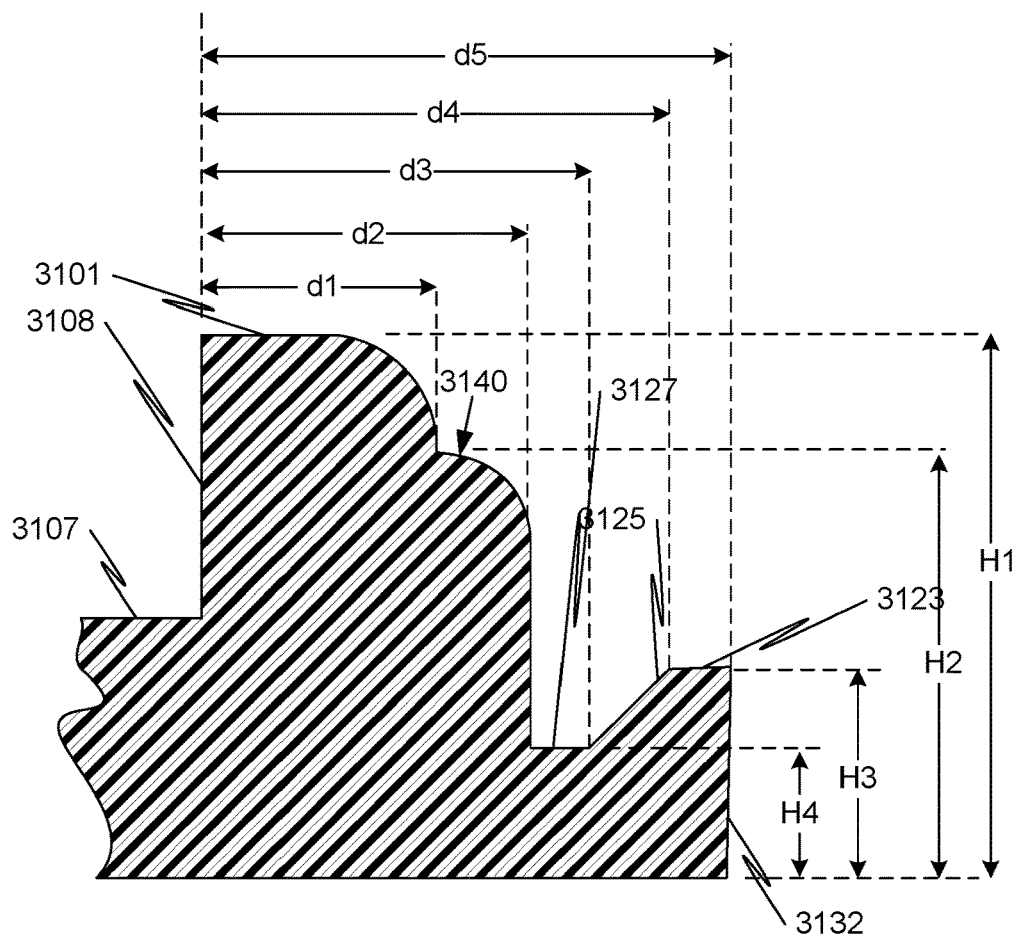
FIGS. 37A and 37B illustrate a portion of an axial section through the plane indicated by VII-VII of FIG. 31.
Figure 37B:
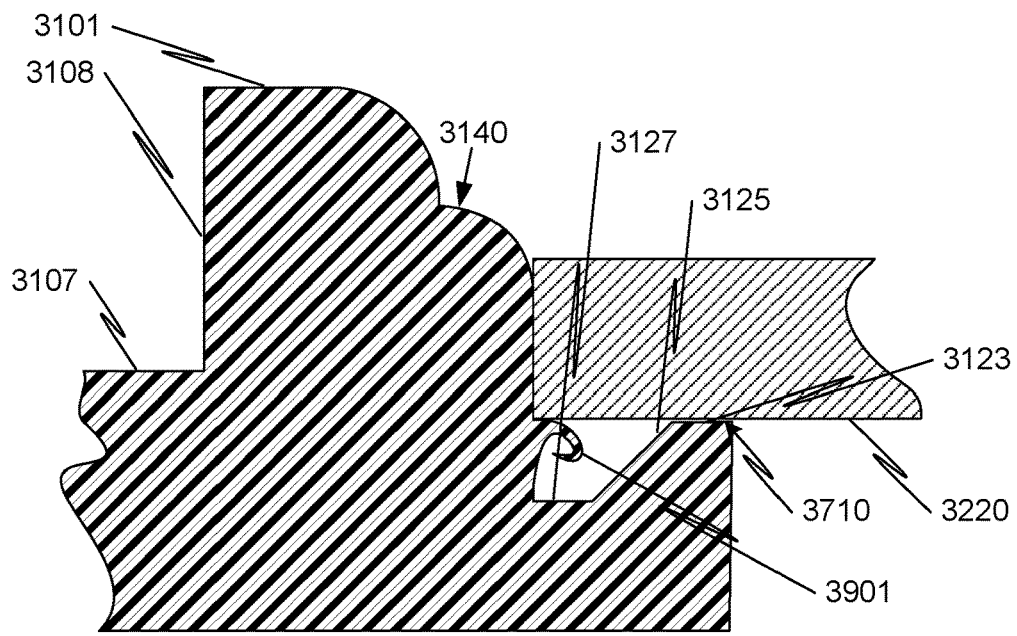
Figure 38A:
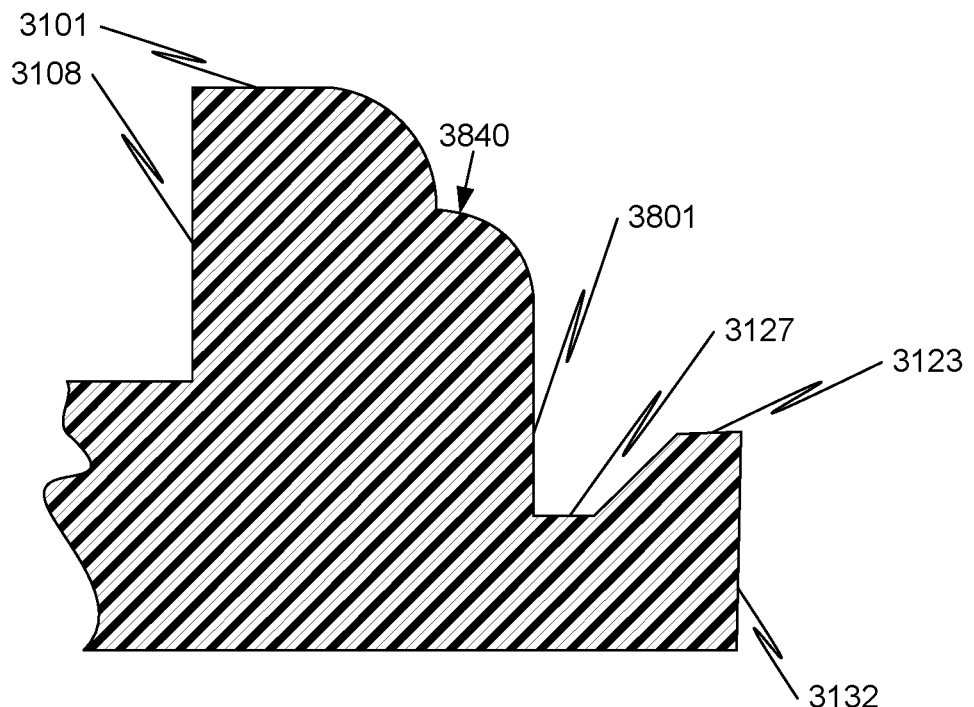
FIG. 38A illustrates a portion of a cross-section view of a spacer according to another embodiment of the disclosure.
Figure 38B:
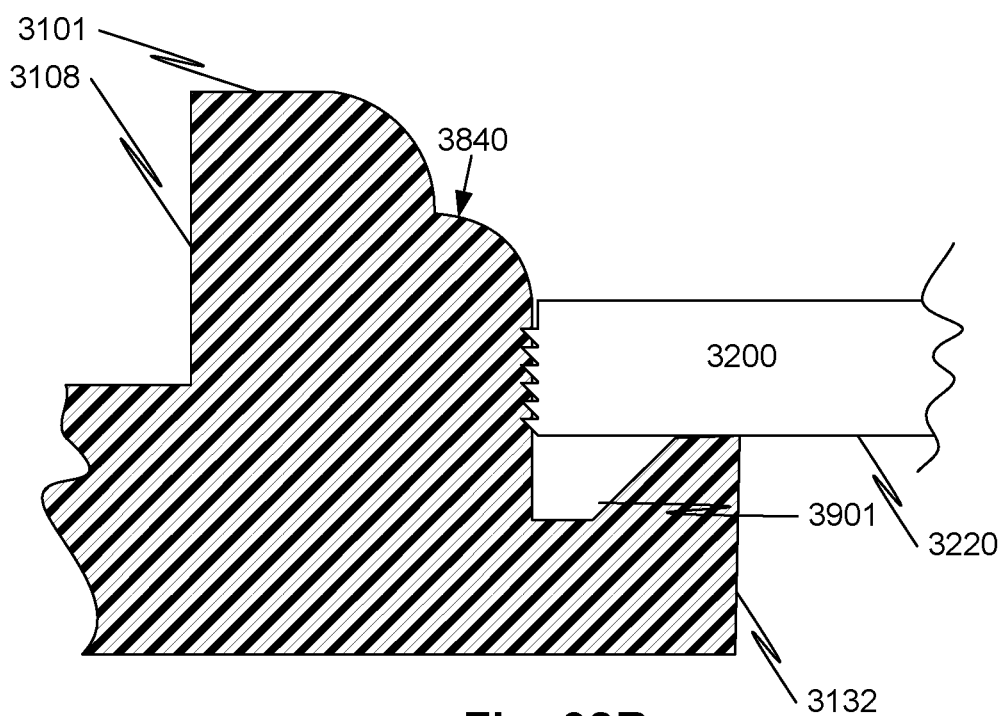
FIG. 38B illustrates a portion of a cross-section view of a spacer according to another embodiment of the disclosure with an inserted electrode.

The inner opening portion 3112 is defined by a sidewall 3132 which has a landing 3123 extending axially toward the outside of the housing thereby defining a trough 3120 between the end of the sidewall 3131 and a landing 3123 at the outside extend of the rim, as shown in FIG. 32. The trough 3120 may have a flat bottom as shown in FIG. 32, or a curved bottom (not shown). The depth and width of the trough 3120 permit shavings or burrs to be received therein when the electrode 3200 is inserted. The dimensions are discussed with reference to FIGS. 37A and 37B. The electrode 3200 may be of a material that is harder or more rigid than the housing 3100, so that pressing the electrode 3200 into the outer opening portion 3111 may produce burrs or shavings 3901 debris as an edge of the electrode 3200 scrapes against sidewall 3131. The burrs or shavings 3901 occupy the trough 3120 such that they are retained in a position that cannot block the electrode 3200 from being seated on the landing 3122, as shown in FIGS. 37B and 38B. The electrode 3200 may have barbs as illustrated in FIGS. 38A and 38B, but in various embodiments, the electrode 3200 can have smooth sides as shown in FIGS. 37A and 37B.

Referring again to FIGS. 31 and 32, the landing 3123 forms a rim 3122 of the inner opening portion 3112. The landing 3123 may provide a support against which a bottom surface 3220 of the electrode 3200 comes to rest. The landing 3123 ensures the electrode 3200 is consistently oriented at a precisely-defined axial position after insertion by providing an interfering engagement with the electrode 3200 which seats against it. The landing 3123 has a finite radial width that may be selected to ensure that it provides a positive stop and resists variable forces to prevent variation in the axial position of the electrode 3200. A fluid-tight seal may be provided but is not essential. An additional function of the radial width of the landing 3123 is to define an elongate narrow fluid path 3710 (See FIG. 37B) between the housing 3107 interior and the portion of the electrode overlying the landing 3123.

After the electrode 3200 is positioned with the bottom surface 3220 resting against the overlying the landing 3123, an open space remains between the radial edge of the 200 and the sidewall 3131 at locations around the sidewall 3131 that do not have a spacer 3140. This open space may be filled with an adhesive substance. The adhesive substance may be a glue or a sealant that cures into a solid or semi-solid form, or may remain pliable even after curing. The adhesive may expand in volume as a part of the curing process, thereby filling any gaps between the bottom surface 3220 and the landing 3123. The viscosity of the uncured adhesive is selected to enable the adhesive to flow into the gap between the sidewall 3131 and the electrode. The adhesive may fill the trough 3120, and may seep onto the top surface of the electrode 3200. It may be desirable to select the volume of the adhesive such that it does not seep onto the top surface, or at least not onto the entirety of the top surface.

Figure 34:
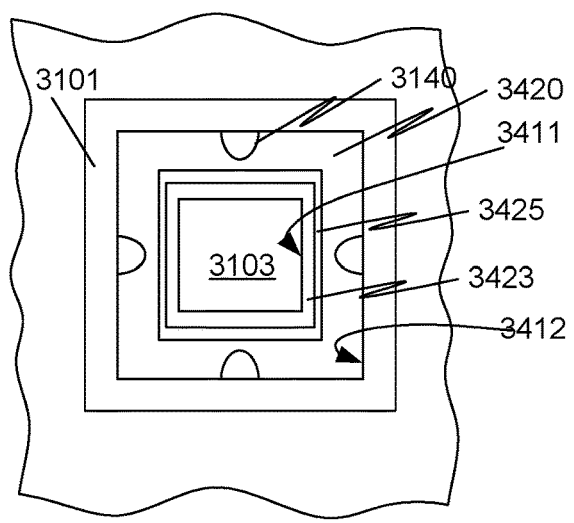
FIGS. 34 through 36 illustrate views of housings with rectangular, elliptical, and triangular openings according to embodiments of the disclosed subject matter.
Figure 36:
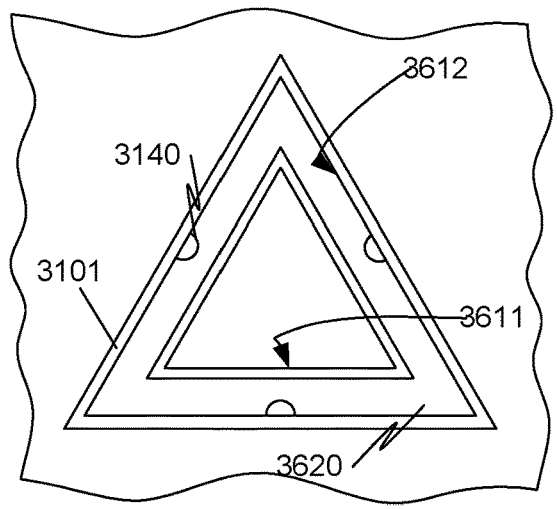
Figure 35:
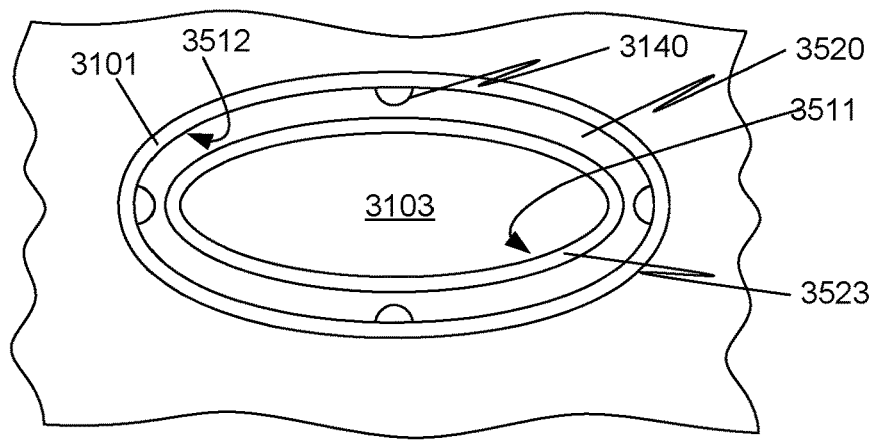

Although FIGS. 31 and 32 illustrate a circular embodiment, the housing is not limited to this shape. FIGS. 34-36 illustrate rectangular, oval, and triangular shapes.

Three spacers 3140 function to constrain the lateral (relative to the opening axis) position of the electrode 3200. The spacers 3140 may be evenly spaced around the perimeter of the opening 3103. A greater number of spacers may be used in alternative embodiment. A smaller number of spacers may cooperate with the walls of the opening to constrain the electrode in further embodiments.

FIGS. 32 and 37A, 37B illustrate details of an embodiment showing spacers 3140. As seen in FIG. 32, spacer 3140 protrudes partially out of the sidewall 3131 of the outer opening portion 3111 and has a semi-circular profile. The general shape of each spacer 3140 may be a hemi-cylinder with an elongate portion 3142 and a rounded end 3141. The spacer 3140 can have other shapes consistent with the function described herein, such as a flat bevel, conical shape, etc. The radial span of the spacer 3140 can be selected to constrain or over-constrain the electrode such that it is deformation or cut when the electrode 3200 slides along the space until it is seated on the overlying the landing 3123.

Advantageously, the provision of the spacers 3140 reduces the contact area of the force of the sidewall against the electrode 3200 making it easier to deform the spacers 3140. By permitting the spacers 3140 to deform or be cut with relatively low force, it possible to provide a relatively gentle over-constraint to the electrode 3200 to keep it centered as it is advanced. The deformation engagement also helps to secure the electrode 3200 axially after it seats against the landing 3123.

Figure 33:
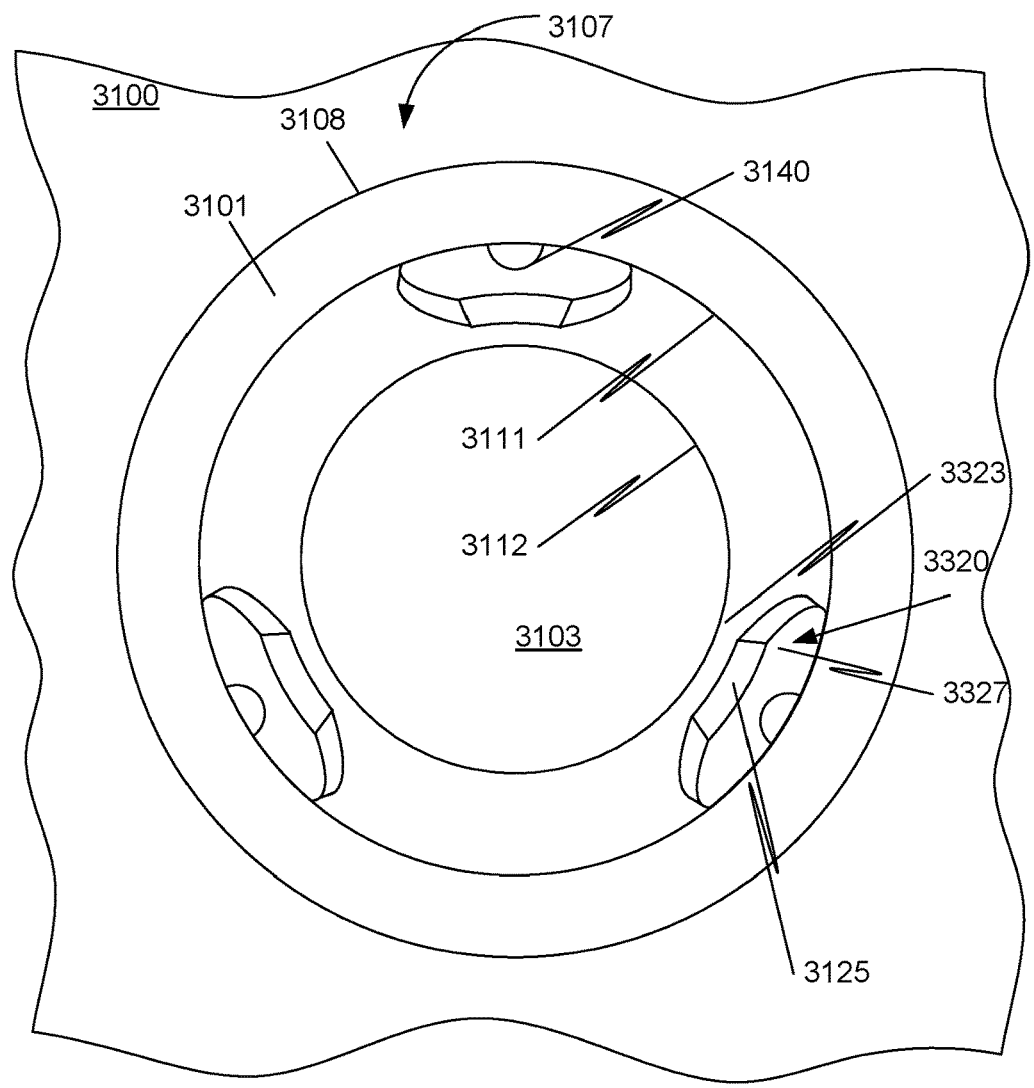
FIG. 33 illustrates a view of an exemplary housing according to embodiments of the disclosed subject matter.

Referring to FIG. 33, an embodiment of the housing 3100 includes a modified trough 3320 that does not extend around the entire perimeter of the opening 3103. Instead, the modified trough 3320 is formed only in the vicinity of the spacers 3140 to accommodate burrs or shavings 3901. No burrs or debris 3901 are scraped off from the sidewall 3131.

The modified trough 3320 has a bottom 3327 and sidewall 3325 which terminates at the sidewall 3131 of the outer opening portion 3111. FIG. 33 illustrates the sidewall 3325 as sloping from the bottom 3327 up to a modified landing 3323. This embodiment provides maximum rigidity of the landing 3323 due to the extra material present, and at the same time still provides the advantages of the trough that accommodates burrs from spacers 3340.

In an embodiment, the modified trough 3320 extends 5 degrees (measured radially from the center of the outer opening portion 3111) on both sides of each of spacers 3140. In another embodiment, the modified trough 3320 extends 10 degrees, 15 degrees, 20 degrees, 25 degrees, or 30 degrees on both sides of each of spacers 3140. The angular extension of the modified trough 3320 can be selected based on the expected amount of burrs 3901 and debris from the spacers 3140 so that the modified trough 3320 can accommodate all of the burrs 3901 and debris.

Turning to FIGS. 34-36, alternate embodiments of the opening may have a rectangular, elliptical, or triangular shape. These shapes may encounter different challenges than those of the round disc embodiment, but nevertheless benefit from spacers 3140. FIG. 34 illustrates an embodiment with a rectangular trough 3420, much like trough 3120 above. FIG. 34 also shows a rectangular landing surface 3423. It is noted that a sidewall 3425 is analogous to the sidewall 3125. However, the slope of the sidewall 3425 (and of the sidewall 3125) may be varied with other aspects of the disclosed embodiments. To illustrate this point further, FIG. 35 shows an embodiment with an elliptical outer opening portion 3511 and elliptical inner opening portion 3512. While this embodiment also includes an elliptical or oval trough 3520 and a landing surface 3523, the slope of the sidewall of the trough 3520 connecting to the surface 3523 is perpendicular to the page, hence not visible in this top view. Such a steeply sloped wall may be desirable space is at a premium, as the resulting stepped opening can be made smaller than other designs.

Referring to FIG. 36, a triangular stepped opening includes a triangular outer opening portion 3611 and a triangular inner opening portion 3612. A triangular trough 3620 is similar to the other embodiments described above in terms of cross section, and can have varying slope of the sidewall (not visible in FIG. 36, as it portrays an embodiment with a side wall of the trough rising out of the page).

FIG. 37 illustrates dimensions of the cross-section of the spacer 3140 as well as the overall stepped opening 3103. The distance from the lower surface 3102 to top surface 3101 is represented at H1. The distance from the lower surface 3102 to the top of the spacer 3104 is represented as H2. The distance from the lower surface 3102 to the landing surface 3123 is represented as H3. The distance from the surface of the bottom 3127 of the trough 3120 is represented as H4. Thus, the height of the spacer 3140 from the bottom 3127 is H2-H4, and must be less than H1.

Still referring to FIG. 37A, the distance from outer wall 3108 to inner wall 3131 of the outer opening portion is represented as d1. The distance from wall 3108 to the farthest point of the closes spacer 3140 is represented as d2. Therefore, the thickness of the spacer 3140 is d2-d1, and is less than the width of the bottom 3127 of the trough 3120, as illustrated in FIG. 37. The distance from the wall 3108 to the farthest end of the bottom 3127 is represented as d3. Therefore, the thickness of the bottom surface 3127 of the trough 3120 is given by d3-d1 in places without a spacer 3140, and by d3-d2 when radially adjacent to a spacer. Distance d4 represents the distance from the wall 3108 to the boundary of the second sidewall 3125 of the trough and the top surface 3123 of the landing 3122. It can be appreciated that varying the slope of the sidewall 3125 affects the thickness of the bottom 3127. If the sidewall 3125 is perpendicular to the lower surface 3102, d3 becomes the same length as d4. The distance from the wall 3108 to the sidewall 3132 is represented as d5.

It has been found that certain ratios of the above-noted dimensions produce particularly desirable results.

Figure 39:
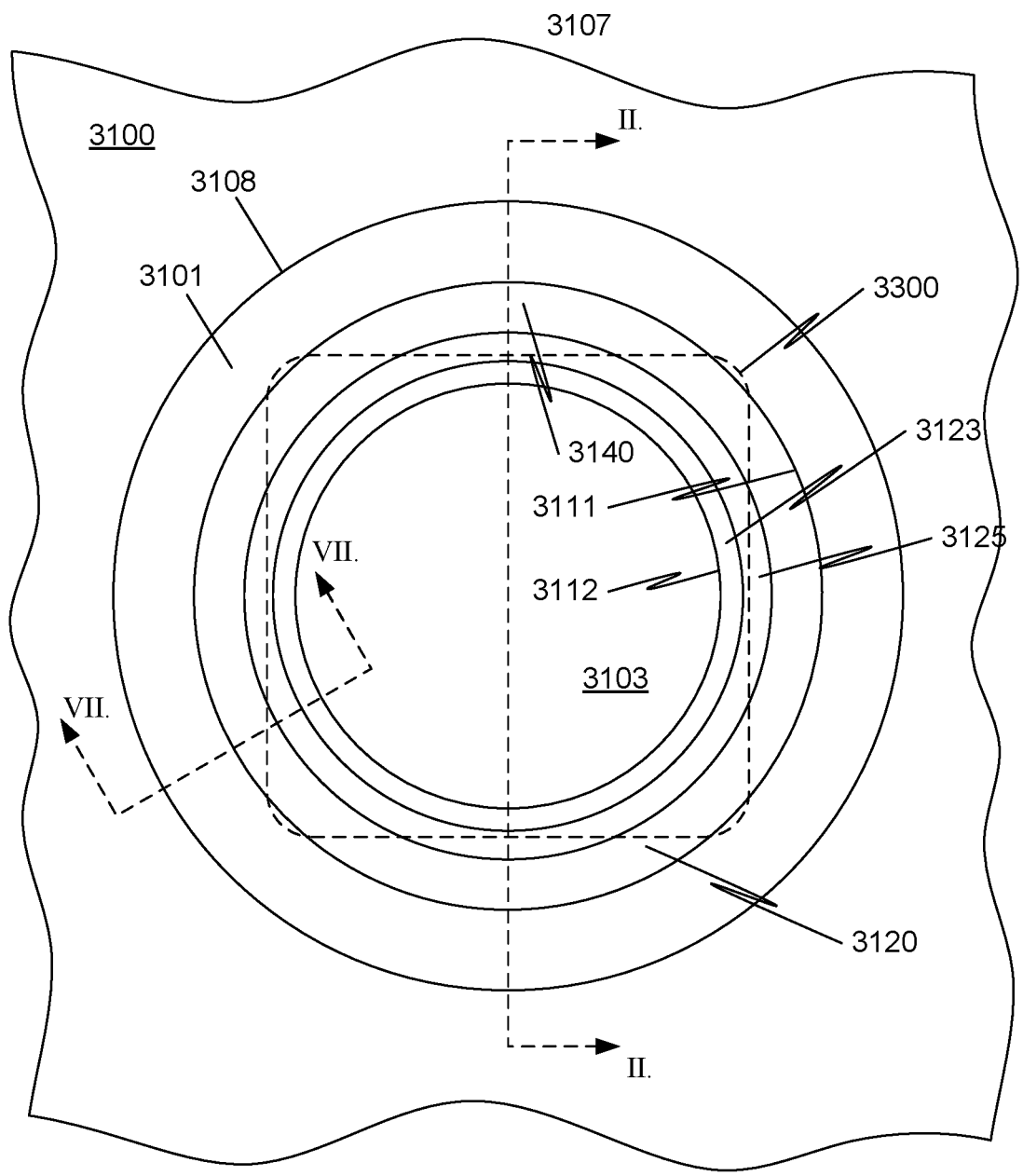
FIGS. 39, 40A, and 40B show alternative embodiments in which, rather than using standoffs extending from the aperture to focus the forces for aligning and engaging the electrode, the electrode itself is shaped to provide a similar effect by forming a non-round electrode that engages the walls of the aperture at predefined points.

Referring to FIG. 39, an alternative embodiment of the electrode 3300 has a shape that, rather than using standoffs extending from the aperture to focus the forces for aligning and engaging the electrode, provides a similar effect by forming a non-round electrode that engages the walls of the aperture at predefined points. In an exemplary embodiment, electrode 3300 has a substantially square profile with rounded corners, as shown in the dashed line in FIG. 39. The rounded corners are the outer-most contact points of the electrode 3300 when it is inserted into an opening 3103, such that the rounded corners come into contact with sidewall 3131, as is shown in FIG. 32. While FIG. 32 illustrates standoff 3140 along sidewall 3131, it is understood that the standoffs 3140 may be omitted.

Figure 40A:
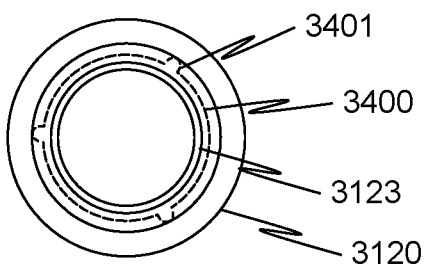

Referring to FIG. 40A, another embodiment of electrode 3400 has a circular profile, like electrode 3200, but may include spacers 3401. The spacers 3401 may be an integral part of the electrode 3400, manufactured as a part of the electrode 3400 during a casting and/or machining process. However, the spacers 3401 may also be added, attached, or machined into electrode 3400 at a later time, before the electrode 3400 is inserted into the opening 3103. The spacers 3401 may be sized to extend radially outward from the electrode 3400 farther than the diameter of the sidewall 3131, such that the sidewall 3131 may be at least partially deformed when the electrode 3400 is inserted.

Figure 40B:
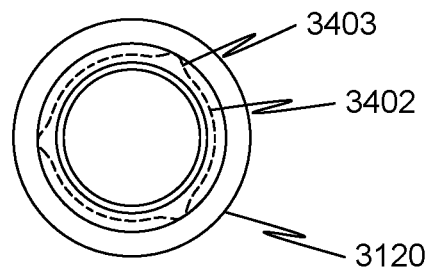

The particular shape of the spacer 3401 may differ from that shown in FIG. 40A. For example, FIG. 40B illustrates an embodiment of electrode 3402 that has spacers 3403 that have a more flat profile as compared to spacers 3401. Thus, spacers 3403 may have a larger contact area that presses against sidewall 3131, and may also be able to exert more force onto that larger area without deforming.

FIGS. 40A and 40B show views that do not illustrate the extension of the spacers 3401 and 403 into the page. It would be understood that the spacers 3401 and 403 need not have the same height as the electrode. In other words, the spacers 3401 and 403 may be formed on only a portion of the electrode 3400, 402 sidewall.

It may be advantageous for electrode 3400 to have three spacers 3401, but it is understood that a different number may be provided. In some embodiments, the electrode may have no spacers and spacers may be omitted from the opening 3103.

Figure 41A:
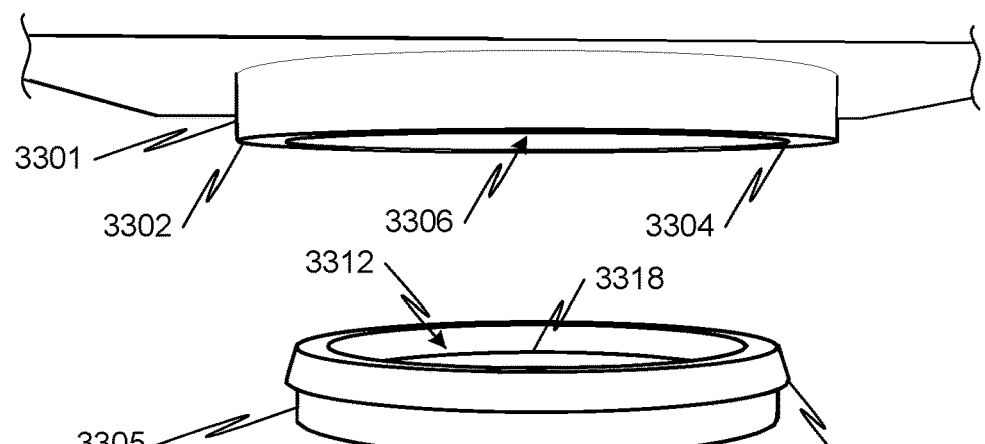
FIGS. 41A and 41B show an electrode embodiment in which the entire circumference engages the outer aperture and is shaped as an annular barb and the electrode may have a recess with an inner aperture pressing against the base of the recess to form a seal while the electrode is pressed into engagement with the inner aperture wall.
Figure 41B:
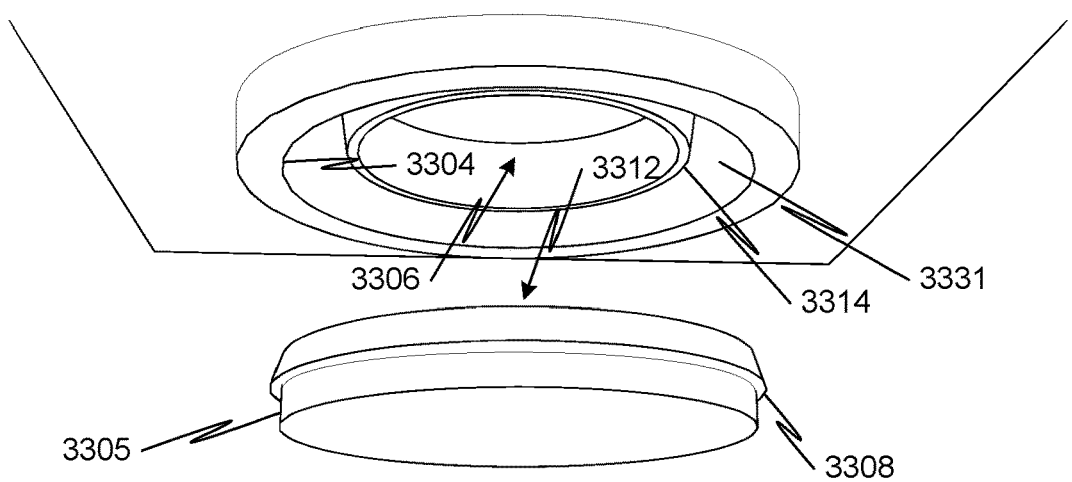

Referring to FIGS. 41A-B, the electrode 3305 includes no spacers, but may include an annular barb 3308 and a recess 3312 at one end. The recess 3312 is bound but upper surface 3318 of the electrode 3305. As shown in FIG. 41A, the annular barb 3308 may have an outer diameter that varies along the height (vertical in FIG. 41A) of the barb. The upper surface 3318 engages with a rim surface 3314 forming a seal when the electrode 3305 is inserted into the opening 3306.

FIGS. 41A-B illustrate the electrode 3305 prior to insertion into or coupling with a housing without any standoffs or spacers. The housing is as shown in FIG. 32, but includes no standoffs. FIGS. 41A and 41B can be thought of as FIG. 32 flipped upside down, with the electrode 3305 being inserted from the bottom rather than from the top.

The housing in FIGS. 41A and 41B includes may include a riser 3301 with a bottom surface 3302. The height of the riser 3301 may vary to accommodate the size of the electrode 3305. The bottom surface 3302 defines the opening 3304 which may be seen from FIG. 41B to be stepped defining an outer opening portion and an inner opening portion. The outer opening portion is larger than the inner opening portion. The outer opening portion may have a rounded lip or have a sharp edge. In embodiments, the axial section profile of sidewall 3331 may be perpendicular the cross-section profile of the bottom surface 3302. However, in other embodiments, the axial section profile of the sidewall 3331 may be sloped.

As would be understood from FIGS. 41A and 41B, when the electrode 3305 is pressed into the housing, outermost edge of the annular barb 3308 engages with the sidewall 3331 and the upper surface 3318 of the electrode 3305 comes to rest against the surface 3314. This engagement may form an air tight or fluid tight seal between the electrode 3305 and the housing. Optionally, an adhesive or sealant may be added into the gap remaining between electrode 3305 and riser 3301 after the electrode is inserted to create an airtight or fluid tight seal.

According to first embodiments, the disclosed subject matter includes a method for measuring a conductivity in a fluid flowing in a fluid channel. The method includes contacting a flowing fluid with two electrodes spaced apart across a portion of the fluid channel. The method includes contacting each of the two electrodes to a current source contact and a voltage measuring contact by creating a continuity between each of two respective portions of the each of the two electrodes and a respective one of the current source and voltage measuring contacts with multiple conductors.

In variations thereof the first embodiments include ones in which the multiple conductors are located on a surface of a resilient insulating member. In variations thereof the first embodiments include ones in which the creating a continuity includes squeezing the resilient member for each of the two electrodes between the each of the two electrodes and a respective combination of the current source and voltage measuring contacts. In variations thereof the first embodiments include ones in which the insulating member and the multiple conductors form a Zebra connector. In variations thereof the first embodiments include ones in which the contacting includes attaching the resilient member to the fluid channel. In variations thereof the first embodiments include ones in which the contacting includes attaching the resilient member to the fluid channel loosely such that it can move in a limited range along an axis perpendicular to a surface of the each of the two electrodes. In variations thereof the first embodiments include ones in which the contacting includes attaching the resilient member to the fluid channel loosely by a housing such that it can move in a limited range along an axis perpendicular to a surface of the each of the two electrodes. In variations thereof the first embodiments include ones in which the contacting includes attaching the resilient member to the fluid channel loosely by a housing partially surrounding the resilient member such that it can move in a limited range along an axis perpendicular to a surface of the each of the two electrodes. In variations thereof the first embodiments include ones that include measuring a resistance of electrical continuity between a voltage measuring contact and a current source contact to detect contact resistance. In variations thereof the first embodiments include ones that include performing Kelvin sensing by electrical impedance between the two electrodes by driving current between the them and measuring a voltage between them. In variations thereof the first embodiments include ones in which the resilient member and all multiple conductors constitutes an elastomeric contact insert or a compliant multiconductor element as described in the embodiments.

According to second embodiments, the disclosed subject matter includes a conductivity measurement system. A single-use fluid circuit has at least two planar electrodes forming a part of a wall of a fluid channel such that the electrode has a wetted side facing an interior of the fluid channel and a contact side opposite the wetted side. Flexible electrically-conducting elements are attached to the fluid channel each with at least one conductor thereof facing a respective one of the electrode contact sides. A multi-use driver has a pair of electrical contacts connected to a current source and a voltage sensor for each of the electrodes. The multi-use driver has a receiving member shaped to receive the single-use fluid circuit fluid channel planar electrodes. The multi-use driving has a forcing member that opens to receive the single-use fluid circuit and closes to force each flexible electrically-conducting element between the each of the electrodes and a respective pair of the electrical contacts.

According to third embodiments, the disclosed subject matter includes a conductivity measurement system. A fluid channel has a first wetted electrode and a second wetted electrode configured to directly contact a fluid flowing in the fluid channel. A first contact device includes a first electrically insulating block wrapped by a first array of parallel electrically conductive wires that span at least a first side of the first contact device and a second side of the first contact device. Conductors on the first side of the first contact device are in electrical contact with the first wetted electrode. A second contact device includes a second electrically insulating block wrapped by a second array of parallel electrically conductive wires that span at least a first side of the second contact device and a second side of the second contact device, wherein wires on the first side of the second contact device are in electrical contact with the second wetted electrode. A conductivity measurement circuit is in electrical contact with the first wetted electrode via wires on the second side of the first contact device and in electrical contact with the second wetted electrode via wires on the second side of the second contact device. A controller is programmed to control the conductivity measurement circuit to pass a current through the fluid between the first wetted electrode and the second wetted electrode and measure a voltage difference between the first wetted electrode and the second wetted electrode as the current is passed, the controller is further programmed to determine a conductivity of the fluid based on the passed current and the measured voltage difference. In variations thereof the third embodiments include ones in which each wire in the first array of parallel electrically conductive wires and in the second array of parallel electrically conductive wires is coated with gold.

In variations thereof the third embodiments include ones in which each adjacent pair of wires in the first array of parallel electrically conductive wires and in the second array of parallel electrically conductive wires are electrically isolated from each other by an electrically insulating material. In variations thereof the third embodiments include ones in which the first electrically insulating block is made of an elastomeric material. In variations thereof the third embodiments include ones in which the first electrically insulating block is made of silicon, rubber, or synthetic rubber. In variations thereof the third embodiments include ones in which the first electrically insulating bock has a recess on a third side of the first contact device, wherein wires spanning the recess are not in contact, over the recess, with the first electrically insulating block. In variations thereof the third embodiments include ones in which the first electrically insulating bock has at least one recess on a fourth side of the first contact device, wherein no wires span the fourth side of the first contact device over the at least one recess. In variations thereof the third embodiments include ones in which the conductivity measurement circuit is in electrical contact with the wires on the second side of the first contact device and in electrical contact with the wires on the second side of the second contact device via a printed circuit board (PCB).

In variations thereof the third embodiments include ones in which a first current contact, a second current contact, a first voltage contact, and a second voltage contact are printed on the PCB, wherein the first current contact is in electrical contact with a first group of wires on the second side of the first contact device, wherein the first voltage contact is in electrical contact with a second group of wires on the second side of the first contact device, wherein the second current contact is in electrical contact with a first group of wires on the second side of the second contact device, wherein the second voltage contact is in electrical contact with a second group of wires on the second side of the second contact device. In variations thereof the third embodiments include ones in which the first current contact and the second current contact are electrically connected to two sides of a current source in the conductivity measurement circuit, wherein the first voltage contact and the second voltage contact are electrically connected to two sides of a voltmeter in the conductivity measurement circuit, wherein the current passed through the fluid between the first wetted electrode and the second wetted electrode is sourced by the current source, wherein the voltage difference between the first wetted electrode and the second wetted electrode is measured by the voltmeter. In variations thereof the third embodiments include ones in which the first contact device includes a housing that supports the first electrically insulating block, wherein the housing is made of an electrically insulating material. In variations thereof the third embodiments include ones in which the first electrically insulating block is inserted into a receiving well of the housing. In variations thereof the third embodiments include ones in which the first side of the first contact device and the second side of the first contact device at least partially protrude from a first end of the receiving well and second end of the receiving well, respectively.

In variations thereof the third embodiments include ones in which the conductivity measurement circuit comprises a permanent electrical device of a treatment system, wherein the fluid channel comprises a replaceable component of the treatment system. In variations thereof the third embodiments include ones in which the treatment system comprises a fluid circuit for preparation of a medicament for renal replacement therapy. In variations thereof the third embodiments include ones in which the treatment system further comprises a water filtration module with a fluid circuit and a pump positioned in the fluid circuit to pump water therethrough, the water filtration module further comprising an inlet, an outlet, and at least one filtration stage has a replaceable filter component, the controller controlling the conductivity measurement circuit to detect the quality of water upstream of the at least one filtration stage and output a water quality signal and control the pump accordingly. In variations thereof the third embodiments include ones in which, when the water quality signal is below a threshold, the controller prevents operation of the pump until the replaceable filter component is changed. In variations thereof the third embodiments include ones in which the replaceable filter component includes a deionization filter or an activated carbon filter. In variations thereof the third embodiments include ones in which the treatment system further comprises a medicament preparation device comprising a medicament supply line that includes at least one concentration sensor station, the concentration sensor station includes the conductivity measurement system and a temperature sensor portion.

In variations thereof the third embodiments include ones in which the conductivity of the fluid is determined based on based on the current passed through the fluid, the voltage difference across the first wetted electrode and the second wetted electrode, and a temperature of the fluid as measured by the temperature sensor portion. In variations thereof the third embodiments include ones in which a supply of a medicament by at least one pump in the medicament preparation device is controlled based on the determined conductivity of the fluid. In variations thereof the third embodiments include ones in which the temperature sensor portion includes a flow chamber with a flat surface to permit a temperature sensor to be placed against the flat surface of a predefined sensor of the medicament preparation device.

According to fourth embodiments, the disclosed subject matter includes a medicament preparation system. A fluid circuit has fluid channels with at least one junction, the junction joining a common flow channel that leads from a water inlet to a medicament outlet. The junction is joined to a pumping tube segment connected to a source of medicament concentrate by a concentrate channel. The at least one junction is oriented in a predefined way relative to the force of gravity. The concentrate channel has a chicane that curves sharply up and sharply down before the concentrate channel meets the common flow channel.

In variations thereof the fourth embodiments include ones in which the chicane's length is no greater than ten internal diameters of the concentrate channel local to the chicane. In variations thereof the fourth embodiments include ones in which the chicane is immediately adjacent a point where the common flow channel and the concentrate channel meet. In variations thereof the fourth embodiments include ones in which the internal cross-sectional flow area of the chicane is smaller than that of the remainder of the concentrate channel. In variations thereof the fourth embodiments include ones in which the chicane is operable as a trap when fluid of a first density remains in the concentrate channel while fluid of a second density remains in the common flow channel at the junction, where the first density is higher than the second density, whereby gravity siphoning is prevented. In variations thereof the fourth embodiments include ones in which the fluid circuit is formed in a rigid structure. In variations thereof the fourth embodiments include ones in which the fluid circuit is formed in a rigid cartridge.

According to fifth embodiments, the disclosed subject matter includes a medical device with a fluid plant that includes a purification element, a patient treatment element, or an admixing element that generates a waste fluid. A drain channel includes means for avoiding fouling including one of, an elastic channel and a pump programmed to expand the elastic channel responsively to a pulsation generated by starting and stopping or reversing the pump.

According to sixth embodiments, the disclosed subject matter includes a medical device with a fluid plant that includes a purification element, a patient treatment element, or an admixing element that generates a waste fluid. A drain channel has a biomimetic surface on an interior surface thereof, the biomimetic surface is selected to prevent attachment or growth of non-flowing material thereon originating from a predefined waste material generated by the purification element, patient treatment element, or admixing element.

According to seventh embodiments, the disclosed subject matter includes a medical device with a fluid plant that includes a purification element, a patient treatment element, or an admixing element that generates a waste fluid. A drain channel is of flexible material, waste is pumped by a pulsatile pump, the flexible material is selected to expand and contract sufficiently to prevent the formation of scaling on the drain channel.

According to eighth embodiments, the disclosed subject matter includes a medical device with a fluid plant that includes a purification element, a patient treatment element, or an admixing element that generates a waste fluid. A drain channel is of expandable material and is connected to receive the waste fluid. An actuator is in engagement with the drain channel and adapted to shake or vibrate the drain channel to prevent fouling thereof by a predefined material generated by the purification element, patient treatment element, or admixing element.

According to ninth embodiments, the disclosed subject matter includes a conductivity sensor with a housing defining an internal fluid compartment. The housing has openings for receiving electrodes. The openings are round. Each of the openings has an inside, closer to the internal fluid compartment, and an outside portion further from the interior. The each of the openings has an axial section with a stepped profile such that the outside portion has a larger diameter than the inside portion. The inside portion has a rim extending axially at least partly into the outside portion. The outside portion has at least three spacers extending radially inward toward an axis of a respective one of the openings.

In variations thereof the ninth embodiments include ones in which the rim is shaped to define an annular trough surrounding a respective one of the openings. In variations thereof the ninth embodiments include ones in which the annular trough is interrupted by the at least three spacers. In variations thereof the ninth embodiments include ones in which the at least three spacers have an axial dimension that is greater than a radial dimension thereof. In variations thereof the ninth embodiments include ones in which the at least three spacers each has a rounded axial end facing away from the interior. In variations thereof the ninth embodiments include ones that include an electrode seated in each of the openings and forming a seal with the rim. In variations thereof the ninth embodiments include ones in which the annular trough is filled with a cement. In variations thereof the ninth embodiments include ones in which the electrode directly abuts the rim. In variations thereof the ninth embodiments include ones in which the trough contains burrs. In variations thereof the ninth embodiments include ones in which the trough contains burrs resulting from over-confinement of the electrode by the spacers and resulting from a press-fitting operation. In variations thereof the ninth embodiments include ones in which the spacers are sized to over-confine the electrode such that burrs are produced by press-fitting of the electrode, the burrs are received by and present in the trough. In variations thereof the ninth embodiments include ones in which the trough is continuous such that it encircles each opening. In variations thereof the ninth embodiments include ones in which the trough is shallower between the spacers than proximate the spacers. In variations thereof the ninth embodiments include ones in which the trough exists only proximate the spacers. In variations thereof the ninth embodiments include ones in which the rim has a base and a tip that is narrower than the base in axial section, the tip and base is spaced apart along the axis of the opening. In variations thereof the ninth embodiments include ones in which the cement partly covers the electrode.

According to tenth embodiments, the disclosed subject matter includes a medical treatment system with a fluid circuit that includes at least one junction where a first fluid line meets a second fluid line. The second fluid line includes a ceiling protrusion extending out of a ceiling of the second fluid line and at least partially blocking the second fluid line. The second fluid line further includes a floor protrusion extending out of a floor of the second fluid line and at least partially blocking the second fluid line. The ceiling protrusion is located farther away from the junction than the floor protrusion.

In variations thereof the tenth embodiments include ones that include a rigid cartridge that contains the fluid circuit. In variations thereof the tenth embodiments include ones in which the ceiling protrusion and the floor protrusion overlap and completely obstruct a central axis of the second fluid line, but leave open a tortuous path through the second fluid line. In variations thereof the tenth embodiments include ones in which the second fluid line has a circular cross sectional profile. In variations thereof the tenth embodiments include ones in which the ceiling protrusion and the floor protrusion cooperate to prevent or reduce flow of fluid through the second fluid line into the junction in the absence of pumping of the fluid when the junction is oriented in a predetermined orientation relative to force of gravity. In variations thereof the tenth embodiments include ones in which a valley is formed immediately adjacent to the floor protrusion and below the ceiling protrusion, and the predetermined orientation is with a center of the valley is vertically aligned with a center of a lowest portion of the ceiling protrusion. In variations thereof the tenth embodiments include ones in which a valley is formed immediately adjacent to the floor protrusion and below the ceiling protrusion when the fluid junction is oriented in a predefined orientation relative to force of gravity and a fluid in the second fluid line is prevented from flowing past the valley due to gravimetric action. In variations thereof the tenth embodiments include ones that include a first pump that selectively applies pumping force to the fluid in the second fluid line and the pumping force causes the fluid in the second fluid line to flow past the valley into the junction. In variations thereof the tenth embodiments include ones that include a second pump that selectively applies pumping force to a fluid flowing in the first fluid line. In variations thereof the tenth embodiments include ones in which the fluid flowing in the first fluid line has a lower density than the fluid flowing in the second fluid line. In variations thereof the tenth embodiments include ones in which the fluid from the second fluid line is mixed with the fluid from the first fluid line when the first and second pumps operate. In variations thereof the tenth embodiments include ones that include an upper protrusion at an intersection of a ceiling of the first fluid line and the ceiling of the second fluid line, the upper protrusion has a tapered cross-sectional shape that extends into a flow channel of the second fluid line. In variations thereof the tenth embodiments include ones in which the upper protrusion reduces turbulence in flow of the fluid in the first fluid line at the junction. In variations thereof the tenth embodiments include ones in which the upper protrusion is rigid. In variations thereof the tenth embodiments include ones that include a flap at an intersection of a ceiling of the first fluid line and the ceiling of the second fluid line, the flap extending from the intersection of the ceilings toward a side wall of the floor protrusion. In variations thereof the tenth embodiments include ones in which the flap is moveable about a pivot and is biased to be touching the side wall of the floor protrusion in the absence of external force applied to the flap. In variations thereof the tenth embodiments include ones in which the flap is a live hinge molded at the intersection of the ceilings. In variations thereof the tenth embodiments include ones in which the flap is movably attached to the pivot with a hinge pin.

According to eleventh embodiments, the disclosed subject matter includes a medical treatment system. A fluid circuit includes a first fluid line and a second fluid line meeting the first fluid line at an intersection. The first fluid line ceiling intersects the second fluid line ceiling at a first location. A fluid flows along the first fluid line in single direction. A flap extends from the first location and rests against a rim of the second fluid line at the intersection. The flap is biased in a closed position that reduces fluid leakage from the second fluid line into the first fluid line in the absence of force that overcomes the bias of the flap.

In variations thereof the eleventh embodiments include ones in which the flap is a living hinge made of a flexible material extending from the first location and substantially parallel to a flow direction of fluid flowing in the first fluid line. In variations thereof the eleventh embodiments include ones in which the flap is a rigid piece of material attached at a pivot location with a hinge pin. In variations thereof the eleventh embodiments include ones that include a fluid pump that pumps the fluid in the second fluid line with a pumping force sufficient to overcome the bias of the flap such that the fluid from the second fluid line flows into the intersection when the fluid pump operates.

According to twelfth embodiments, the disclosed subject matter includes a medical device cartridge insertable into a medical treatment device. The cartridge has a rigid frame that provides structure for the cartridge and a fluid circuit supported within the rigid frame. The fluid circuit includes fluid channels with at least one junction, the junction joining a common flow channel that leads from a water inlet to a medicament outlet. The junction is joined to a pumping tube segment connected to a source of medicament concentrate by a concentrate channel. The at least one junction is oriented in a predefined way relative to the force of gravity. The concentrate channel has a chicane that curves sharply up and sharply down before the concentrate channel meets the common flow channel. At least one conductivity sensor that measures conductivity of fluid in the fluid circuit, the conductivity sensor includes a housing defining an internal fluid compartment, the housing has openings for receiving electrodes, the openings being round. Each of the openings has inside portions closer to the internal fluid compartment and outside portions further from the interior of the internal fluid compartment, the each of the openings having an axial section with a stepped profile such that the outside portion has a larger diameter than the inside portion. The inside portion has a rim extending axially at least partly into the outside portion. The outside portion has at least three spacers extending radially inward toward an axis of a respective one of the openings.

In variations thereof the twelfth embodiments include ones that include a drain line fluidly attached to a drain channel of the fluid circuit, wherein the drain line conveys waste fluid.

In variations thereof the twelfth embodiments include ones in which the drain line includes means for reducing fouling in the drain line. In variations thereof the twelfth embodiments include ones in which the drain line is made of an elastic material that allows the drain line to expand and contract and the waste fluid is pumped by a pump with fluctuating pumping pressure that causes the drain line to expand and contract and thereby reduce attachment of fouling on an interior of the drain line. In variations thereof the twelfth embodiments include ones that include a support structure surrounding at least a portion of the drain line. In variations thereof the twelfth embodiments include ones in which the support structure is more rigid than the drain line. In variations thereof the twelfth embodiments include ones in which the support structure includes a plurality of cut-outs in a body of the support structure. In variations thereof the twelfth embodiments include ones that include a holster holding at least a portion of the drain line, the holster mechanically coupled to motor. In variations thereof the twelfth embodiments include ones in which the motor applies force to the holster and causes the holster to flex the drain line held by the holster to thereby remove fouling built up inside the drain line. In variations thereof the twelfth embodiments include ones that include multiple holsters arranged along at least a portion of the drain line, wherein the motor causes adjacent holsters to move in opposed directions to flex the drain line held by the holsters.

In variations thereof the twelfth embodiments include ones in which at least one of the drain line and the drain channel has a biomimetic surface on an interior surface thereof, the biomimetic surface is selected to prevent attachment or growth of non-flowing material thereon originating from a predefined waste material generated by a purification element, a patient treatment element, or an admixing element.

According to thirteenth embodiments, the disclosed subject matter includes a medical device cartridge insertable that is into a medical treatment device. The cartridge has a fluid circuit that includes fluid channels with at least one junction, the junction joining a common flow channel that leads from a water inlet to a medicament outlet. The junction is joined to a pumping tube segment connected to a source of medicament concentrate by a concentrate channel. The at least one junction is oriented in a predefined way relative to the force of gravity. The concentrate channel has a chicane that curves sharply up and sharply down before the concentrate channel meets the common flow channel. At least one conductivity sensor measures conductivity of fluid in the fluid circuit. The conductivity sensor includes a housing defining an internal fluid compartment. The housing has openings for receiving electrodes. The openings are round. Each of the openings has inside portions closer to the internal fluid compartment and outside portions further from the interior of the internal fluid compartment. The each of the openings has an axial section with a stepped profile such that the outside portion has a larger diameter than the inside portion. The inside portion has a rim extending axially at least partly into the outside portion. The outside portion has at least three spacers extending radially inward toward an axis of a respective one of the openings. A fluid channel has a first wetted electrode and a second wetted electrode configured to directly contact a fluid flowing in the fluid channel. A first contact device includes a first electrically insulating block wrapped by a first array of parallel electrically conductive wires that span at least a first side of the first contact device and a second side of the first contact device, wherein conductors on the first side of the first contact device are in electrical contact with the first wetted electrode. A second contact device includes a second electrically insulating block wrapped by a second array of parallel electrically conductive wires that span at least a first side of the second contact device and a second side of the second contact device, wherein wires on the first side of the second contact device are in electrical contact with the second wetted electrode. A conductivity measurement circuit in electrical contact with the first wetted electrode via wires on the second side of the first contact device and in electrical contact with the second wetted electrode via wires on the second side of the second contact device. A controller is programmed to control the conductivity measurement circuit to pass a current through the fluid between the first wetted electrode and the second wetted electrode and measure a voltage difference between the first wetted electrode and the second wetted electrode as the current is passed, the controller is further programmed to determine a conductivity of the fluid based on the passed current and the measured voltage difference.

Features of the disclosed embodiments may be combined, rearranged, omitted, etc., within the scope of the disclosed subject matter to produce additional embodiments. Furthermore, certain features may sometimes be used to advantage without a corresponding use of other features. It is, thus, apparent that there is provided, in accordance with the present disclosure, a needle guard and associated manufactures, components, systems, and methods of use. Many alternatives, modifications, and variations are enabled by the present disclosure. While specific embodiments have been shown and described in detail to illustrate the application of the principles of the disclosure, it will be understood that the disclosed subject matter may be embodied otherwise without departing from such principles. Accordingly, Applicants intend to embrace all such alternatives, modifications, equivalents, and variations that are within the spirit and scope of the present disclosure.

In any of the embodiments described herein, including the claims, the terms compliant multiconductor element elastomeric contact element, elastomeric contact, and elastomeric contact insert may be interchanged to form alternative embodiments. In any of the embodiments, the terms compliant multiconductor element, elastomeric contact insert, or elastomeric contact may be loosely held to an electrode by a housing such as housing 752. In embodiments, the housing may be a flexible material such as soft plastic, rubber, silicone, elastomer, or other compliant material. The housing (e.g., 752) may be attached to the cartridge support 556 or equivalent conductivity measurement channel portion but not directly affixed to the compliant multiconductor element and elastomeric contact insert. That is, the housing may hold the element/insert in place over the electrode but permit it to move relative to the electrode so that it can be firmly pressed against it.

It will be appreciated that the modules, processes, systems, and sections described above can be implemented in hardware, hardware programmed by software, software instruction stored on a non-transitory computer readable medium or a combination of the above. For example, a method for controlling the generating of a medicament or treatment fluid (or methods therewithin such as for the generating of purified water) can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems, sensors, electromechanical effecters and/or computer programming arts.

Moreover, embodiments of the disclosed method, system, and computer program product can be implemented in software executed on a programmed general-purpose computer, a special purpose computer, a microprocessor, or the like.

It is, thus, apparent that there is provided, in accordance with the present disclosure, medicament preparation and treatment devices, methods, and systems. Many alternatives, modifications, and variations are enabled by the present disclosure. Features of the disclosed embodiments can be combined, rearranged, omitted, etc., within the scope of the disclosed subject matter to produce additional embodiments. Furthermore, certain features may sometimes be used to advantage without a corresponding use of other features. Accordingly, Applicant intends to embrace all such alternatives, modifications, equivalents, and variations that are within the spirit and scope of the present disclosed subject matter.

The invention claimed is:

1. A method for measuring a conductivity in a fluid flowing in a fluid channel, comprising:
   contacting a flowing fluid with two electrodes spaced apart across a portion of the fluid channel; and
   contacting each of the two electrodes to a current source contact and a voltage measuring contact by creating a continuity between each of two respective portions of the each of the two electrodes and a respective one of the current source and voltage measuring contacts with multiple conductors located on a surface of a resilient insulating member,
   wherein the creating the continuity includes squeezing the resilient insulating member for each of the two electrodes between the each of the two electrodes and a respective combination of the current source and voltage measuring contacts.

2. The method of claim 1, wherein the resilient insulating member and the multiple conductors form a Zebra connector.

3. The method of claim 1, wherein the contacting includes attaching the resilient insulating member to the fluid channel.

4. The method of claim 1, wherein the contacting includes attaching the resilient insulating member to the fluid channel loosely such that the resilient insulating member can move in a limited range along an axis perpendicular to a surface of said each of the two electrodes.

5. The method of claim 1, wherein the contacting includes attaching the resilient insulating member to the fluid channel loosely by a housing such that the resilient insulating member can move in a limited range along an axis perpendicular to a surface of said each of the two electrodes.

6. The method of claim 1, wherein the contacting includes attaching the resilient insulating member to the fluid channel loosely by a housing partially surrounding the resilient insulating member such that the resilient insulating member can move in a limited range along an axis perpendicular to a surface of said each of the two electrodes.

7. The method of claim 6, further comprising measuring a resistance of electrical continuity between the voltage measuring contact and the current source contact to detect contact resistance.

8. The method of claim 6, further comprising performing Kelvin sensing by measuring an electrical impedance between the two electrodes by driving current between the two electrodes while measuring a voltage between them the two electrodes.

9. The method of claim 6 wherein the resilient insulating member and the multiple conductors constitute an elastomeric contact insert or a compliant multiconductor element.

10. A conductivity measurement system, comprising:
a replaceable fluid circuit with at least two electrodes forming a part of a wall of a fluid channel such that each of the at least two electrodes has a wetted side facing an interior of the fluid channel and a contact side opposite the wetted side;
flexible electrically-conducting elements attached to the fluid channel each with at least one conductor thereof facing the contact side of a respective one of said at least two electrodes;
a medicament proportioning module having a pair of electrical contacts connected to a current source and a voltage sensor for each of the at least two electrodes;
the medicament proportioning module being configured to receive the replaceable fluid circuit such that each of the flexible electrically-conducting elements is forced between the respective one of the at least two electrodes and a respective one of the pairs of electrical contacts.

11. A conductivity measurement system, comprising:
a fluid channel with a first wetted electrode and a second wetted electrode configured to directly contact a fluid flowing in the fluid channel;
a first contact device including a first electrically insulating block wrapped by a first array of parallel electrically conductive wires that span at least a first side of the first contact device and a second side of the first contact device, wherein conductors on the first side of the first contact device are in electrical contact with the first wetted electrode;
a second contact device including a second electrically insulating block wrapped by a second array of parallel electrically conductive wires that span at least a first side of the second contact device and a second side of the second contact device, wherein wires on the first side of the second contact device are in electrical contact with the second wetted electrode;
a conductivity measurement circuit in electrical contact with the first wetted electrode via wires on the second side of the first contact device and in electrical contact with the second wetted electrode via wires on the second side of the second contact device; and
a controller programmed to control the conductivity measurement circuit to pass a current through the fluid between the first wetted electrode and the second wetted electrode and measure a voltage difference between the first wetted electrode and the second wetted electrode as the current is passed, the controller being further programmed to determine a conductivity of the fluid based on the passed current and the measured voltage difference.

12. The system of claim 11, wherein each wire in the first array of parallel electrically conductive wires and in the second array of parallel electrically conductive wires is coated with gold.

13. The system of claim 11, wherein each adjacent pair of wires in the first array of parallel electrically conductive wires and in the second array of parallel electrically conductive wires are electrically isolated from each other by an electrically insulating material.

14. The system of claim 11, wherein the first electrically insulating block is made of an elastomeric material.

15. The system of claim 11, wherein the first electrically insulating block is made of silicon, rubber, or synthetic rubber.

16. The system of claim 15, wherein the first electrically insulating bock has a recess on a third side of the first contact device, wherein wires spanning the recess are not in contact, over the recess, with the first electrically insulating block.

17. The system of claim 16 wherein the first electrically insulating bock has at least one recess on a fourth side of the first contact device, wherein no wires span the fourth side of the first contact device over the at least one recess.

18. The system of claim 16 wherein the conductivity measurement circuit is in electrical contact with the wires on the second side of the first contact device and in electrical contact with the wires on the second side of the second contact device via a printed circuit board (PCB).

* * * * *